US008552199B2

(12) United States Patent
Schwink et al.

(10) Patent No.: US 8,552,199 B2
(45) Date of Patent: Oct. 8, 2013

(54) SUBSTITUTED INDANES, METHOD FOR THE PRODUCTION THEREOF, AND USE THEREOF AS DRUGS

(75) Inventors: Lothar Schwink, Frankfurt am Main (DE); Siegfried Stengelin, Frankfurt am Main (DE); Matthias Gossel, Frankfurt am Main (DE); Klaus Wirth, Frankfurt am Main (DE)

(73) Assignee: Sanofi, Paris (FR)

( * ) Notice: Subject to any disclaimer, the term of this patent is extended or adjusted under 35 U.S.C. 154(b) by 6 days.

(21) Appl. No.: 13/201,410

(22) PCT Filed: Feb. 12, 2010

(86) PCT No.: PCT/EP2010/051796
§ 371 (c)(1),
(2), (4) Date: Oct. 4, 2011

(87) PCT Pub. No.: WO2010/092154
PCT Pub. Date: Aug. 19, 2010

(65) Prior Publication Data
US 2012/0022039 A1 Jan. 26, 2012

(30) Foreign Application Priority Data

Feb. 13, 2009 (EP) ..................................... 09290109

(51) Int. Cl.
*A61K 31/44* (2006.01)
*C07D 211/72* (2006.01)

(52) U.S. Cl.
USPC .......................................... 546/290; 514/354

(58) Field of Classification Search
None
See application file for complete search history.

(56) References Cited

U.S. PATENT DOCUMENTS

| 5,639,778 | A * | 6/1997 | Andersson et al. ............ 514/411 |
| 6,878,721 | B1 * | 4/2005 | Cuenoud et al. ............... 514/312 |
| 8,097,759 | B2 * | 1/2012 | Muto et al. ..................... 564/179 |
| 2003/0216391 | A1 | 11/2003 | Lowe et al. |
| 2005/0075324 | A1 | 4/2005 | Hu |
| 2006/0247239 | A1 | 11/2006 | Hu |
| 2008/0058423 | A1 | 3/2008 | Hu |

FOREIGN PATENT DOCUMENTS

| WO | WO00/51970 A1 | 9/2000 |
| WO | WO01/21577 A2 | 3/2001 |
| WO | WO02/02744 A2 | 1/2002 |
| WO | WO02/05733 A1 | 1/2002 |
| WO | WO02/06245 A1 | 1/2002 |
| WO | WO02/10146 A1 | 2/2002 |
| WO | WO02/064565 A1 | 8/2002 |
| WO | WO02/089729 A2 | 11/2002 |
| WO | WO03/035624 A1 | 5/2003 |
| WO | WO03/045313 A2 | 6/2003 |
| WO | WO03/087044 A2 | 10/2003 |
| WO | WO03/087046 A1 | 10/2003 |
| WO | WO03/097047 A1 | 11/2003 |
| WO | WO2004/024702 A1 | 3/2004 |
| WO | WO2004/092181 A1 | 10/2004 |
| WO | WO2005/033063 A2 | 4/2005 |
| WO | WO2005/047293 A1 | 5/2005 |
| WO | WO2005/056540 A1 | 6/2005 |
| WO | WO2005/103039 A1 | 11/2005 |
| WO | WO2006/044293 A2 | 4/2006 |
| WO | WO2007/018248 A1 | 2/2007 |
| WO | WO2007/039174 A2 | 4/2007 |
| WO | WO2007/039462 A2 | 4/2007 |
| WO | WO2008/001160 A1 | 1/2008 |
| WO | WO2008/002575 A1 | 1/2008 |
| WO | WO2008/022979 A1 | 2/2008 |

OTHER PUBLICATIONS

Hu, X. Eric et al., "Small-Molecule Melanin-Concentrating Hormone-1 Receptor Antagonists Require Brain Penetration for Inhibition of Food Intake and Reduction in Body Weight," The Journal of Pharmacology and Experimental Therapeutics (2008), vol. 324, No. 1, pp. 206-213.
Borowsky, Beth et al., "Antidepressant, anxiolytic and anorectic effects of a melanin-concentrating hormone-1 receptor antagonist," Nature Medicine (2002), vol. 8, No. 8, pp. 825-830.
Chaki, Shigeyuki et al., "Melanin-Concentrating Hormone Receptor 1 Antagonists for the Treatment of Depression and Anxiety," Drug Development Research (2005), vol. 65, pp. 278-290.
Chen, Yanyun et al., "Targeted Disruption of the Melanin-Concentrating Hormone Receptor-1 Results in Hyperphagia and Resistance to Diet-Induced Obesity," Endocrinology (2002), vol. 143, pp. 2469-2477.
Rivera, Gildardo et al., "Melanin-Concentrating Hormone Receptor 1 Antagonists: A New Perspective for the Pharmacologic Treatment of Obesity," Current Medicinal Chemistry (2008), vol. 15, pp. 1025-1043.
Chaki, Shigeyuki et al., "Neuropeptide receptors: novel therapeutic targets for depression and anxiety disorders," Drugs of the Future (2007), vol. 32, No. 9, pp. 809-822.
Dyck, Brian, "Small Molecule Melanin-Concentrating Hormone Receptor 1 (MCH1R) Antagonists as Anxiolytic and Antidepressive Agents," Drug Development Research (2005), vol. 65, pp. 291-300.
Pereira, Marcio et al., "Hypothalamic Melanin-Concentrating Hormone is Induced by Cold Exposure and Participates in the Control of Energy Expenditure in Rats," Endocrinology (2003), vol. 144, No. 11, pp. 4831-4840.
Hervieu, Guillaume, "Melanin-concentrating hormone functions in the nervous system: food intake and stress," Expert Opinion on Therapeutic Targets (2003), vol. 7, No. 4, pp. 495-511.

(Continued)

*Primary Examiner* — Janet Andres
*Assistant Examiner* — Heidi Reese
(74) *Attorney, Agent, or Firm* — Scully, Scott, Murphy & Presser, P.C.

(57) ABSTRACT

The invention relates to substituted indanes and derivatives thereof, to physiologically acceptable salts and physiologically functional derivatives thereof, to the production thereof, to drugs containing at least one substituted indane according to the invention or derivative thereof, and to the use of the substituted indanes according to the invention and to derivatives thereof as MCH antagonists.

16 Claims, No Drawings

(56) References Cited

OTHER PUBLICATIONS

Benjahad, Abdellah et al., "4-Benzyl and 4-Benzoyl-3-dimethylaminopyridin-2(1H)-ones: In Vitro Evaluation of New C-3-Amino-Substituted and C-5,6-Alkyl-Substituted Analogues against Clinically Important HIV Mutant Strains," Journal of Medicinal Chemistry (2005), vol. 48, pp. 1948-1964.

Kelly, T. Ross et al., "A Rationally Designed Prototype of a Molecular Motor," Journal of the American Chemical Society (2000), vol. 122, pp. 6935-6949.

Klaus, Stefan et al., "A General and Efficient Method for the Formylation of Aryl and Heteroaryl Bromides," Angewandte Chemie International Edition (2006), vol. 45, pp. 154-158.

Luthin, David R., "Anti-obesity effects of small molecule melanin-concentrating hormone receptor 1 (MCHR1) antagonists," Life Sciences (2007), vol. 81, pp. 423-440.

Mendez-Andino, Jose L. et al., "The efficacy and cardiac evaluation of aminomethyl tetrahydronaphthalene ketopiperazines: A novel class of potent MCH-R1 antagonists," Bioorganic and Medicinal Chemistry (2007), vol. 15, pp. 2092-2105.

Meyers, Kenneth M. et al., "Aminomethyl tetrahydronaphthalene ketopiperazine MCH-R1 antagonists—Increasing selectivity over hERG," Bioorganic and Medicinal Chemistry Letters (2007), vol. 17, pp. 819-822.

Meyers, Kenneth M. et al., "Aminomethyl tetrahydronaphthalene biphenyl carboxamide MCH-R1 antagonists—Increasing selectivity over hERG," Bioorganic and Medicinal Chemistry Letters (2007), vol. 17, pp. 814-818.

Pissios, Pavlos et al., "Expanding the Scales: The Multiple Roles of MCH in Regulating Energy Balance and Other Biological Functions," Endocrine Reviews (2006), vol. 27, No. 6, pp. 606-620.

Audinot, Valerie et al., "[125I]-S36057: a new and highly potent radioligand for the melanin-concentrating hormone receptor," British Journal of Pharmacology (2001), vol. 133, pp. 371-378.

Qu, Daqing et al., "A role for melanin-concentrating hormone in the central regulation of feeding behaviour," Nature (1996), vol. 380, pp. 243-247.

Renaud, J. L. et al., "Ruthenium-Catalysed Enantioselective Hydrogenation of Trisubstituted Enamides Derived from 2-Tetralone and 3-Chromanone: Influence of Substitution on the Amide Arm and the Aromatic Ring," Advanced Synthesis and Catalysis (2003), vol. 345, pp. 230-238.

Rokosz, Laura L., "Discovery and development of melanin-concentrating hormone receptor 1 antagonists for the treatment of obesity," Expert Opinion on Drug Discovery (2007), vol. 2, No. 10, pp. 1301-1327.

Shi, Yuguang, "Beyond skin color: emerging roles of melanin-concentrating hormone in energy homeostasis and other physiological functions," Peptides (2004), vol. 25, pp. 1605-1611.

Shimada, Masako et al., "Mice lacking melanin-concentrating hormone are hypophagic and lean," Nature (1998), vol. 396, pp. 670-674.

Shimazaki, Toshiharu et al., "Melanin-Concentrating Hormone MCH1 Receptor Antagonists: A Potential New Approach to the Treatment of Depression and Anxiety Disorders," CNS Drugs (2006), vol. 20, No. 10, pp. 801-811.

Pave, Gregoire et al., "A New Efficient Synthesis of Spirocyclic Benzopyrans," Synthesis (2004), No. 1, pp. 0121-0127.

Holzapfel, Cedric W. et al., "Palladium-Catalysed Cyclisation of Chiral Carbohydrate-Derived Geminal Diacetates," Tetrahedron (1999), vol. 55, pp. 3467-3478.

Tschaen, David M. et al., "Asymmetric Synthesis of MK-0499," Journal of Organic Chemistry (1995), vol. 60, pp. 4324-4330.

Audinot, Valerie et al., "Structure-Activity Relationship Studies of Melanin-concentrating Hormone (MCH)-related Peptide Ligands at SLC-1, the Human MCH Receptor," The Journal of Biological Chemistry (2001), vol. 276, No. 17, pp. 13554-13562.

International Preliminary Report on Patentability dated Aug. 16, 2011 issued in PCT/EP2010/051796.

\* cited by examiner

SUBSTITUTED INDANES, METHOD FOR THE PRODUCTION THEREOF, AND USE THEREOF AS DRUGS

The invention relates to substituted indanes and derivatives thereof, and the physiologically compatible salts and physiologically functional derivatives thereof, to the preparation thereof, to medicaments comprising at least one substituted indane or derivative thereof, and to the use of the inventive substituted indanes and derivatives thereof as medicaments.

Compounds which have a different pharmacological action but whose overall structure is similar to that of the substituted indanes and derivatives thereof described in the present application have already been described in the prior art, for example stimulants of endothelial NO synthase for treatment of cardiovascular disorders in WO2002/064565, antagonists of the dopamine D2 receptor or of the serotonin 2A (5HT2A) receptor for treatment of schizophrenia in WO2005056540, and PPAR agonists in WO2007039174.

Further compounds with MCH-antagonistic action for treatment of obesity are described in the prior art (examples: WO2005047293, WO2004092181, WO2005103039, WO2004024702, WO2001021577, WO2003035624, WO2002089729, WO2002006245, WO2002002744, WO2002057233, WO2003045313, WO2003097047, WO2002010146, WO 2003087044, WO2003/087046, WO2001/021577, WO2007018248, WO2008022979, US2008058423, WO2008/002575, WO2008/001160, WO2006/044293, WO2005/033063, US2005/0075324, US 2006/0247239). Reviews are given in Rokosz, L. L., Expert Opin. Drug Discov, 2007, 2, 1301-1327 and Curr. Med. Chem. 2008, 15, 1025-1043.

It was an object of the invention to provide novel compounds which bring about a reduction in weight in mammals and which are suitable for prevention of obesity and diabetes, and the various sequelae thereof.

A series of compounds which modulate the activity of MCH receptors has been found. More particularly, the compounds are notable for antagonism of MCH R1. The invention therefore relates to compounds of the formula I

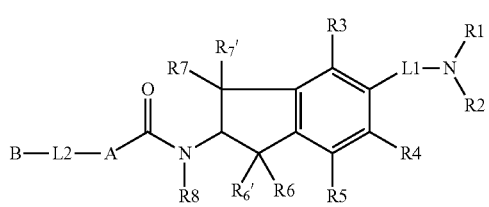

in which
R1
is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R9), (C(R10)(R11))$_q$-R12, CO(C(R13)(R14))$_r$-R15, CO—O($C_1-C_8$)-alkyl, CO(C(R13)(R14))$_r$-N(R16)(R17);
R2
is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R9), (C(R10)(R11))$_q$-R12, CO(C(R13)(R14))$_r$-R15, CO—O($C_1-C_8$)-alkyl, CO(C(R13)(R14))$_r$-N(R16)(R17);
or
R1 and R2 form, together with the nitrogen atom to which they are bonded, a 4- to 10-membered mono-, bi- or spirocyclic ring which, apart from the nitrogen atom, may include 0 to 3 additional heteroatoms selected from the group of oxygen, nitrogen and sulfur, where the heterocyclic ring system may additionally be substituted by F, Cl, Br, CF$_3$, CN, $(C_1-C_6)$-alkyl, $(C_3-C_8)$-cycloalkyl, O—$(C_1-C_8)$-alkyl, $(C_1-C_4)$-alkoxy-$(C_1-C_4)$-alkyl, hydroxy-$(C_1-C_6)$-alkyl, oxo, CO(R18), CON(R19)(R20), hydroxyl, COO(R21), N(R22)CO($C_1-C_6$)-alkyl, N(R23)(R24) or SO$_2$($C_1-C_6$)-alkyl;
R10, R11
are each independently H, $(C_1-C_6)$-alkyl, hydroxy-$(C_1-C_2)$-alkyl, F, OH;
R9, R13, R14, R16, R17, R18, R19, R20, R21, R22, R23, R24,
are each independently H, $(C_1-C_6)$-alkyl;
or
R16 and R17, R23 and R24
optionally form, together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;
q, r are each independently 0, 1, 2, 3, 4, 5, 6;
R12, R15
are each independently H, OH, F, O—$(C_1-C_6)$-alkyl, S—$(C_1-C_6)$-alkyl, CN, COO(R25), N(R26)CO($C_1-C_6$)-alkyl, N(R27)(R28), CON(R29)(R30), SO$_2$($C_1-C_6$)-alkyl, a 3-12-membered mono-, bi- or spirocyclic ring which may contain one to four heteroatoms from the group of N, O and S and the 3-12-membered ring may contain further substituents such as F, Cl, Br, OH, CF$_3$, NO$_2$, CN, OCF$_3$, oxo, O—$(C_1-C_6)$-alkyl, $(C_1-C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R31)(R32), COO(R33), SO$_2$($C_1-C_6$)-alkyl and COOH;
R25, R26, R27, R28, R29, R30, R31, R32, R33
are each independently H, $(C_1-C_6)$-alkyl;
or
R27 and R28, R29 and R30, R31 and R32
each independently optionally form, together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;
L1 is C(R34)(R35), C(R36)(R37)C(R38)(R39), $(C_3-C_6)$-cycloalkyl;
R2 may optionally be joined to one of the R34, R35, R36, R37, R38 or R39 radicals so as to form an optionally (C1-C6)-alkyl-substituted 5-6-membered ring;
R34, R35, R36, R37, R38, R39
are each independently H, $(C_1-C_6)$-alkyl,
R3, R4, R5
are each independently H, F, Cl, Br, I, OH, CF$_3$, NO$_2$, CN, OCF$_3$, O—$(C_1-C_6)$-alkyl, S—$(C_1-C_6)$-alkyl, O—$(C_1-C_4)$-alkoxy-$(C_1-C_4)$-alkyl, $(C_1-C_6)$-alkyl, CON(R40)(R41), CO(R42);
R40, R41, R42
are each independently H, $(C_1-C_6)$-alkyl;
or
R40 and R41
each independently optionally form, together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;

R6, R6', R7, R7'
  are each independently H, F, $(C_1-C_6)$-alkyl, OH, O—$(C_1-C_6)$-alkyl;

R8 is H, $(C_1-C_6)$-alkyl;

A is a 5-6-membered aromatic ring which may include up to 2 heteroatoms selected from the group of nitrogen, oxygen and sulfur, and may be substituted by one or more of the substituents H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, $(C_1-C_6)$-alkyl, N(R43)(R44), $SO_2$—$CH_3$, CON(R45)(R46), N(R47)CO(R48), CO(R49);

optionally, C(O)NR8 may be joined to an ortho substituent of A via a bridge comprising one or two elements from the group of carbon and nitrogen so as to form, overall, a 9- to 10-membered bicyclic ring;

R43, R44, R45, R46, R47, R48, R49
  are each independently H, $(C_1-C_6)$-alkyl;
or
R43 and R44, R45 and R46
  each independently optionally form, together with the nitrogen atom to which they are bonded, a 5-6-membered ring which, apart from the nitrogen atom, may also include 0-1 further heteroatom from the group of NH, N—$(C_1-C_6)$-alkyl, oxygen and sulfur;

L2 is a bond or a linker with 1 to 4 members, where the members are selected from the group consisting of O, S, $SO_2$, N(R50), CO, C(R51)(R52), C≡C to form a chemically viable radical, and the linker has no O—CO or COO groups;

B is $(C_1-C_6)$-alkyl, $(C_1-C_4)$-alkoxy-$(C_1-C_4)$-alkyl, hydroxy-$(C_1-C_6)$-alkyl, a 3- to 10-membered mono-, bi- or spirocyclic nonaromatic ring which may include 0 to 3 heteroatoms selected from the group of oxygen, nitrogen and sulfur, where the ring system may additionally be substituted by one or more of the following substituents: F, $CF_3$, $(C_1-C_6)$-alkyl, O—$(C_1-C_8)$-alkyl, $(C_1-C_4)$-alkoxy-$(C_1-C_4)$-alkyl, hydroxy-$(C_1-C_4)$-alkyl, oxo, CO(R53), hydroxyl;

R50, R51, R52, R53
  are each independently H, $(C_1-C_6)$-alkyl.

The compounds of the formula I are notable in that they have an improved solubility in aqueous media (especially in physiologically relevant buffer systems) as compared with structurally similar compounds with MCH-antagonistic action, coupled with simultaneously high activity. Moreover, preferred inventive compounds are notable for low blockage of the hERG channel, which is more preferably associated with sufficient brain penetration. Furthermore, preferred inventive compounds have an improved metabolic stability as compared with prior art compounds.

The alkyl, alkenyl and alkynyl radicals in the substituents R1, R2, R3, R4, R5, R6, R6', R7, R7', R8, R9, R10, R11, R12, R13, R14, R15, R16, R17, R18, R19, R20, R21, R22, R23, R24, R25, R26, R27, R28, R29, R30, R31, R32, R33, R34, R35, R36, R37, R38, R39, R40, R41, R42, R43, R44, R45, R46, R47, R48, R49, R50, R51, R52, R53 may be either straight-chain, branched and/or optionally substituted by substituents such as $(C_1-C_4)$-alkoxy or halogen. This also applies when the alkyl, alkenyl and alkynyl radicals are part of another group, for example part of an alkoxy group (such as $(C_1-C_4)$-alkoxy-$(C_1-C_4)$-alkyl)). Suitable halogens are fluorine, chlorine, bromine and iodine, preferably fluorine, chlorine and bromine, particularly preferably fluorine.

Examples of alkyl groups are: methyl, ethyl, propyl, butyl, pentyl, hexyl, heptyl and octyl. Included therein are both the n-isomers of these radicals and branched isomers such as isopropyl, isobutyl, isopentyl, sec-butyl, tert-butyl, neopentyl, 3,3-dimethylbutyl, etc. Unless stated otherwise, the term alkyl additionally also includes alkyl radicals which are unsubstituted or optionally substituted by one or more (e.g. 1, 2, 3 or 4) further radicals from the group consisting of $(C_1-C_4)$-alkoxy or halogen. Examples of alkyl groups substituted by halogen are fluorinated alkyl groups such as $CF_3$, $CHF_2$, $CH_2F$, 3-fluoroprop-1-yl, 2,2,1,1-tetrafluoroethyl. The additional substituents may appear in any desired position of the alkyl radical. Unless defined otherwise, the alkyl radicals are preferably unsubstituted.

Cycloalkyl means in the context of the present application cycloalkyl and cycloalkylalkyl (alkyl which is in turn substituted by cycloalkyl), where cycloalkyl has at least 3 carbon atoms. Examples of cycloalkyl radicals are: cyclopropyl, cyclobutyl, cyclopentyl, cyclohexyl, cycloheptyl, cyclooctyl, cyclononyl and cyclodecyl. Polycyclic ring systems are also possible where appropriate, such as decalinyl, norbornanyl, bornanyl or adamantanyl. The cycloalkyl radicals may be unsubstituted or optionally substituted by one or more further radicals as listed above for the alkyl radicals. Unless defined otherwise, the cycloalkyl radicals are preferably unsubstituted.

Examples of alkenyl and alkynyl groups are: vinyl, 1-propenyl, 2-propenyl (allyl), 2 butenyl, 2-methyl-2-propenyl, 3-methyl-2-butenyl, ethynyl, 2-propynyl (propargyl), 2 butynyl or 3-butynyl.

Cycloalkenyl means in the context of the present application cycloalkenyl radicals and cycloalkenylalkyl radicals (alkyl which is substituted by cycloalkenyl), which comprise at least three carbon atoms. Examples of cycloalkenyl are: cyclopentenyl, cyclohexenyl, cycloheptenyl and cyclooctenyl.

The alkenyl radicals and cycloalkenyl radicals may have one to three conjugated or non-conjugated double bonds (i.e. also alkadienyl and alkatrienyl radicals), preferably one double bond in a linear or branched chain. The same applies to the triple bonds for alkynyl radicals. The alkenyl and alkynyl radicals may be unsubstituted or optionally substituted by one or more further radicals as listed by way of example above for the alkyl radicals. Unless defined otherwise, the alkenyl and alkynyl radicals are preferably unsubstituted.

A polycyclic group (bi-, tri- or spirocyclic ring structure) means in the context of the present application a group which is derived from spirans, fused ring systems or bridged ring systems. The spirans are notable for two rings having only one carbon atom in common and the ring planes of the two rings being perpendicular to one another. In the fused ring systems, two rings are linked together in such a way that they have two atoms in common. This type of linkage involves an "ortho fusion". Bridged ring systems are ring systems having a bridge of carbon atoms and/or heteroatoms between two nonadjacent atoms of a ring.

A "chemically viable radical" means in the context of the present invention a radical which is stable at room temperature and atmospheric pressure. In the context of the present invention, a "chemically viable radical" in the definition of group L2 in compounds of the formula I preferably means groups which have no heteroatom-heteroatom bonds between the individual members of the groups.

The compounds of the formula I may have one or more centers of asymmetry. The compounds of the formula I may therefore exist in the form of their racemates, enantiomer-enriched mixtures, pure enantiomers, diastereomers and mixtures of diastereomers. The present invention encompasses all these isomeric forms of the compounds of the formula I. These isomeric forms may be obtained by known methods, even if not expressly described in some cases.

Pharmaceutically acceptable salts are generally, because their solubility in water is greater than that of the initial or basic compounds, particularly suitable for medical applications. These salts must have a pharmaceutically acceptable anion or cation. Suitable pharmaceutically acceptable acid addition salts of the compounds of the invention are salts of inorganic acids such as hydrochloric acid, hydrobromic acid, phosphoric acid, metaphosphoric acid, nitric acid and sulfuric acid, and of organic acids, for example acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p toluenesulfonic acid and tartaric acid. Suitable pharmaceutically acceptable basic salts are ammonium salts, alkali metal salts (such as sodium and potassium salts), alkaline earth metal salts (such as magnesium and calcium salts) and salts of trometamol (2 amino-2 hydroxymethyl-1,3 propanediol), diethanolamine, lysine or ethylenediamine.

Salts with a pharmaceutically unacceptable anion, for example trifluoroacetate, likewise belong within the framework of the invention as useful intermediates for the preparation or purification of pharmaceutically acceptable salts and/or for use in nontherapeutic, for example in vitro, applications.

The present invention also includes solvates of compounds of the formula I, for example hydrates or adducts with solvents, for example alcohols such as ($C_1$-$C_4$)-alkanols.

The term "physiologically functional derivative" used herein refers to any physiologically tolerated derivative of a compound of the formula I of the invention, for example an ester, which on administration to a mammal, for example a human, is able to form (directly or indirectly) a compound of the formula I or an active metabolite thereof.

Physiologically functional derivatives also include prodrugs of the compounds of the invention, as described, for example, in H. Okada et al., Chem. Pharm. Bull. 1994, 42, 57-61. Such prodrugs can be metabolized in vivo to a compound of the invention.

These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula I" hereinafter refer to compound(s) of the formula I as described above, and their salts, solvates and physiologically functional derivatives as described herein.

If radicals or substituents can occur more than once in the compounds of the formula I, they may each independently be defined as specified and be the same or different.

The symbols in the formula I are preferably each independently defined as follows:

R1
is H, ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO(R9), (C(R10)(R11))$_q$-R12, CO(C(R13)(R14))$_r$-R15, CO—O($C_1$-$C_8$)-alkyl, CO(C(R13)(R14))$_r$N(R16)(R17), R2
is ($C_1$-$C_8$)-alkyl, ($C_1$-$C_4$)-alkoxy-($C_1$-$C_4$)-alkyl, ($C_3$-$C_8$)-alkenyl, ($C_3$-$C_8$)-alkynyl, CO(R9), (C(R10)(R11))$_q$-R12, CO(C(R13)(R14))$_r$-R15, CO—O($C_1$-$C_8$)-alkyl, CO(C(R13)(R14))$_r$N(R16)(R17);

R1 is preferably:
H, ($C_1$-$C_8$)-alkyl, (C(R10)(R11))$_q$-R12, ($C_1$-$C_4$)-alkoxy-($C_1$-$C_4$)-alkyl, CO—($C_1$-$C_8$)-alkyl, CO—O($C_1$-$C_8$)-alkyl, CO(C(R13)(R14))$_r$N(R16)(R17), R2 is preferably:
($C_1$-$C_8$)-alkyl, (C(R10)(R11))$_q$-R12, ($C_1$-$C_4$)-alkoxy-($C_1$-$C_4$)-alkyl;

R1 is more preferably:
H, ($C_1$-$C_8$)-alkyl, (C(R10)(R11)$_q$-R12, ($C_1$-$C_4$)-alkoxy-($C_1$-$C_4$)-alkyl;

R2 is more preferably:
($C_1$-$C_8$)-alkyl, (C(R10)(R11))$_q$-R12, ($C_1$-$C_4$)-alkoxy-($C_1$-$C_4$)-alkyl;

or

R1 and R2 form, together with the nitrogen atom to which they are bonded, a 4- to 10-membered mono-, bi- or spirocyclic ring which, apart from the nitrogen atom, may include 0 to 3 additional heteroatoms selected from the group of oxygen, nitrogen and sulfur, where the heterocyclic ring system may additionally be substituted by F, Cl, Br, $CF_3$, CN, ($C_1$-$C_6$)-alkyl, ($C_3$-$C_8$)-cycloalkyl, O—($C_1$-$C_8$)-alkyl, ($C_1$-$C_4$)-alkoxy-($C_1$-$C_4$)-alkyl, hydroxy-($C_1$-$C_6$)-alkyl, oxo, CO(R18), CON(R19)(R20), hydroxyl, COO(R21), N(R22)CO($C_1$-$C_6$)-alkyl, N(R23)(R24) or $SO_2$($C_1$-$C_6$)-alkyl;

R1 and R2 preferably form, together with the nitrogen atom to which they are bonded, a 4- to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, Cl, Br, $CF_3$, ($C_1$-$C_6$)-alkyl, O—($C_1$-$C_8$)-alkyl, ($C_3$-$C_8$)-cycloalkyl, ($C_1$-$C_4$)-alkoxy-($C_1$-$C_4$)-alkyl, hydroxy-($C_1$-$C_6$)-alkyl, oxo, CO(R18), hydroxyl, N(R22)CO($C_1$-$C_6$)-alkyl, or $SO_2$($C_1$-$C_6$)-alkyl;

R1 and R2 more preferably form, together with the nitrogen atom to which they are bonded, a 4- to 10-membered mono-, bi- or spirocyclic ring which, apart from the nitrogen atom, may include 0 to 2 additional heteroatoms selected from the group of oxygen, nitrogen and sulfur, where the heterocyclic ring system may additionally be substituted by F, $CF_3$, ($C_1$-$C_6$)-alkyl, O—($C_1$-$C_8$)-alkyl, ($C_1$-$C_4$)-alkoxy-($C_1$-$C_4$)-alkyl, hydroxy-($C_1$-$C_6$)-alkyl, oxo, CO(R18) or hydroxyl;

R10, R11
are each independently H, ($C_1$-$C_6$)-alkyl, hydroxy-($C_1$-$C_2$)-alkyl, F, OH; preferably H, ($C_1$-$C_6$)-alkyl, OH; more preferably H, ($C_1$-$C_6$)-alkyl;

R9, R13, R14, R16, R17, R18, R19, R20, R21, R22, R23, R24,
are each independently H, ($C_1$-$C_6$)-alkyl;

or

R16 and R17, R23 and R24
optionally form, together with the nitrogen atom to which they are bonded, a 5-6-membered ring which, apart from the nitrogen atom, may also include 0-1 further heteroatom from the group of NH, N—($C_1$-$C_6$)-alkyl, oxygen and sulfur;

q, r are each independently 0, 1, 2, 5, 6; preferably 0, 1, 2, 3, 4;

R12, R15
are each independently H, OH, F, O—($C_1$-$C_6$)-alkyl, S—($C_1$-$C_6$)-alkyl, CN, COO(R25), N(R26)CO($C_1$-$C_6$)-alkyl, N(R27)(R28), CON(R29)(R30), $SO_2$($C_1$-$C_6$)-alkyl, a 3-12-membered mono-, bi- or spirocyclic ring which may contain one to four heteroatoms from the group of N, O and S and the 3-12-membered ring may contain further substituents such as F, Cl, Br, OH, CF$_3$, NO$_2$, CN, OCF$_3$, oxo, O—(C$_1$-C$_6$)-alkyl, (C$_1$-C$_4$)-alkoxy-(C$_1$-C$_4$)-alkyl, S—(C$_1$-C$_6$)-alkyl, (C$_1$-C$_6$)-alkyl, (C$_2$-C$_6$)-alkenyl, (C$_3$-C$_8$)-cycloalkyl, O—(C$_3$-C$_8$)-cycloalkyl, (C$_3$-C$_8$)-cycloalkenyl, O—(C$_3$-C$_8$)-cycloalkenyl, (C$_2$-C$_6$)-alkynyl, N(R31)(R32), COO(R33), SO$_2$(C$_1$-C$_6$)-alkyl and COOH;

preferably H, OH, F, O—(C$_1$-C$_6$)-alkyl, N(R26)CO(C$_1$-C$_6$)-alkyl, SO$_2$(C$_1$-C$_6$)-alkyl, a 3-12-membered mono-, bi- or spirocyclic nonaromatic ring which may contain one to three heteroatoms from the group of N, O and S and the 3-12-membered ring may contain further substituents such as F, Cl, Br, OH, CF$_3$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R31)(R32) and SO$_2$(C$_1$-C$_6$)-alkyl;

R25, R26, R27, R28, R29, R30, R31, R32, R33
are each independently H, (C$_1$-C$_6$)-alkyl;
or
R27 and R28, R29 and R30, R31 and R32
each independently optionally form, together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;

L1 is C(R34)(R35), C(R36)(R37)C(R38)(R39), (C$_3$-C$_6$)-cycloalkyl;
preferably C(R34)(R35);
R2 may optionally be joined to one of the R34, R35, R36, R37, R38 or R39 radicals so as to form an optionally (C1-C6)-alkyl-substituted 5-6-membered ring;
R34, R35, R36, R37, R38, R39
are each independently H, (C$_1$-C$_6$)-alkyl;
R3, R4, R5
are each independently H, F, Cl, Br, I, OH, CF$_3$, NO$_2$, CN, OCF$_3$, O—(C$_1$-C$_6$)-alkyl, S—(C$_1$-C$_6$)-alkyl, O—(C$_1$-C$_4$)-alkoxy-(C$_1$-C$_4$)-alkyl, (C$_1$-C$_6$)-alkyl, CON(R40)(R41), CO(R42);
preferably each independently H, F, Cl, Br, CF$_3$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl, CO(C$_1$-C$_6$)-alkyl;
more preferably each independently H, F, Cl, Br, CF$_3$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl;
even more preferably each independently H, F, Cl, O—(C$_1$-C$_6$)-alkyl, (C$_1$-C$_6$)-alkyl;
even more especially preferably H;
where preferably at least two, or all, R3, R4 and R5 radicals are H;
R40, R41, R42
are each independently H, (C$_1$-C$_6$)-alkyl;
or
R40 and R41
optionally form, together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;
R6, R6', R7, R7'
are each independently H, F, (C$_1$-C$_6$)-alkyl, OH, O—(C$_1$-C$_6$)-alkyl;
preferably H;
R8 is H, (C$_1$-C$_6$)-alkyl;
A is a 5-6-membered aromatic ring which may include up to 2 heteroatoms selected from the group of nitrogen, oxygen and sulfur, and may be substituted by one or more of the substituents H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl, N(R43)(R44), SO$_2$—CH$_3$, CON(R45)(R46), N(R47)CO(R48), CO(R49); preferably H, F, Cl, Br, I, OH, CF$_3$, NO$_2$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl; more preferably H, F, Cl, Br, CF$_3$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl; even more preferably H, F, Cl, O—(C$_1$-C$_6$)-alkyl, (C$_1$-C$_6$)-alkyl; even more especially preferably H;

the 5-6-membered aromatic ring is preferably selected from the group consisting of

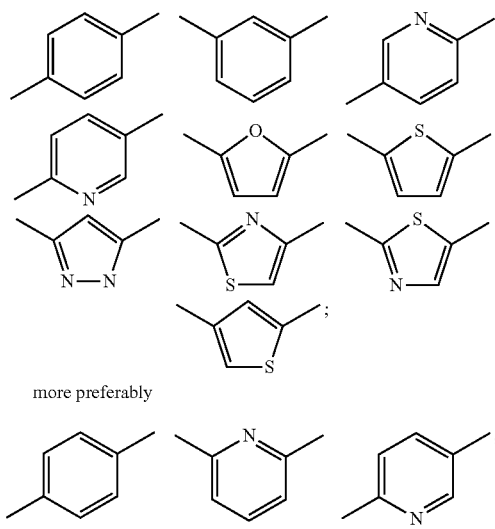

more preferably

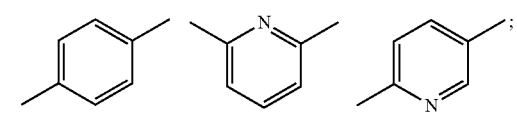

optionally, C(O)NR8 may be joined to an ortho substituent of A via a bridge comprising one or two elements from the group of carbon and nitrogen so as to form, overall, a 9- to 10-membered bicyclic ring;
the bridge preferably contains two carbon elements, so as to form, overall, an isoquinolinone or a dihydroisoquinolinone;
R43, R44, R45, R46, R47, R48, R49
are each independently H, (C$_1$-C$_6$)-alkyl;
or
R43 and R44, R45 and R46
each independently optionally form, together with the nitrogen atom to which they are bonded, a 5-6-membered ring which, apart from the nitrogen atom, may also include 0-1 further heteroatom from the group of NH, N—(C$_1$-C$_6$)-alkyl, oxygen and sulfur;
L2 is a bond or a linker with 1 to 4 members, where the members are selected from the group consisting of O, S, SO$_2$, N(R50), CO, C(R51)(R52), C≡C to form a chemically viable radical, and the linker has no O—CO or COO groups; preferably a bond or a linker with 1 to 4 members, where the members are
selected from the group consisting of O; N(R50), CO, C(R51)(R52) to form
a chemically viable radical, and the linker has no O—CO or COO groups; more preferably a bond, O, C(R51)(R52)O;
B (C$_1$-C$_6$)-alkyl, (C$_1$-C$_4$)-alkoxy-(C$_1$-C$_4$)-alkyl, hydroxy-(C$_1$-C$_6$)-alkyl, a 3- to 10-membered mono-, bi- or spirocyclic nonaromatic ring which may include 0 to 3 heteroatoms selected from the group of oxygen, nitrogen and sulfur, where the ring system may additionally be substituted by one or more of the following substituents: F, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R53), hydroxyl; preferably (C$_1$-C$_6$)-alkyl, (C$_1$-C$_4$)-alkoxy-(C$_1$-C$_4$)-alkyl, a 3- to 6-membered nonaromatic ring which may include 1 or 2 oxygen atoms, where the ring system may additionally be substituted by one or more of the following substituents: F, (C$_1$-C$_6$)-alkyl, (C$_1$-C$_4$)-alkoxy-(C$_1$-C$_4$)-alkyl, oxo, hydroxyl, preferably (C$_1$-C$_6$)-alkyl or hydroxyl;

more preferably a 3- to 6-membered nonaromatic ring which includes 1 or 2 oxygen atoms, where the ring system may additionally be substituted by one or more of the following substituents: F, (C$_1$-C$_6$)-alkyl, O—(C$_1$-C$_8$)-alkyl, (C$_1$-C$_4$)-alkoxy-(C$_1$-C$_4$)-alkyl, oxo, hydroxyl, preferably (C$_1$-C$_6$)-alkyl or hydroxyl;

more preferably the combined element B-L2
selected from the group of

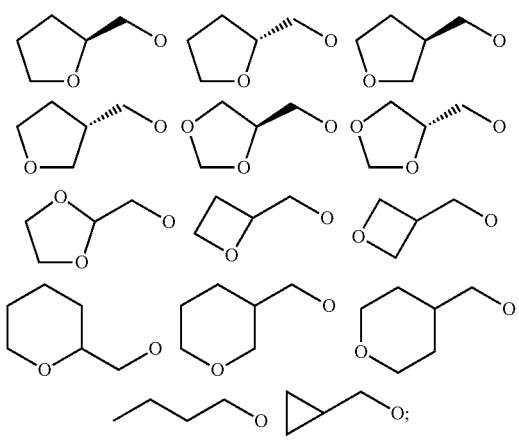

preferably

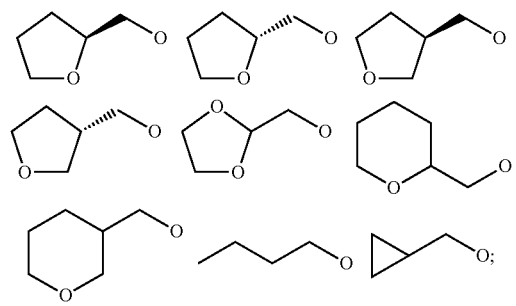

more preferably

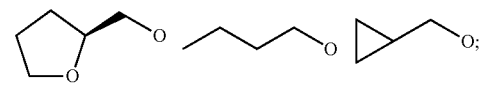

even more preferably

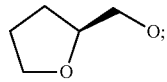

R50, R51, R52, R53
are each independently H, (C$_1$-C$_6$)-alkyl.

A particular aspect of the invention is that of the compounds of the formula II

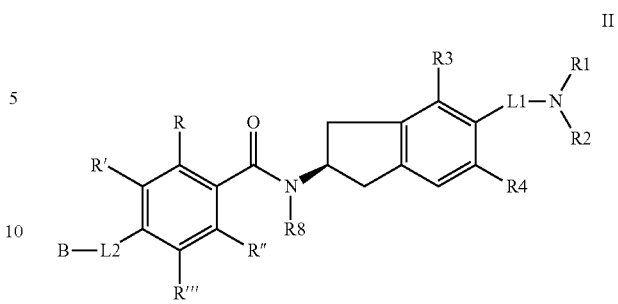

in which the variables R1, R2, L1, R3, R4 and R8 are each as defined for formula I
and R, R', R", R'"
are each independently H, F, Cl, Br, I, OH, CF$_3$, NO$_2$, CN, OCF$_3$, O—(C$_1$-C$_6$), alkyl, O—(C$_1$-C$_4$)-alkoxy-(C$_1$-C$_4$)-alkyl, (C$_1$-C$_6$)-alkyl, N(R43)(R44), SO$_2$—CH$_3$, CON(R45)(R46), N(R47)CO(R48), CO(R49);

preferably each independently H, F, Cl, Br, I, OH, CF$_3$, NO$_2$, CN, OCF$_3$, O—(C$_1$-C$_6$)-alkyl, (C$_1$-C$_4$)-alkoxy-(C$_1$-C$_4$)-alkyl, (C$_1$-C$_6$)-alkyl;

more preferably each independently H, F, Cl, Br, CF$_3$, ON, OCF$_3$, O—(C$_1$-C$_6$)-alkyl, (C$_1$-C$_4$)-alkoxy-(C$_1$-C$_4$)-alkyl, (C$_1$-C$_6$)-alkyl;

even more preferably each independently H, F, Cl, O—(C$_1$-C$_6$)-alkyl, (C$_1$-C$_6$)-alkyl;

even more especially preferably H;

L2 is CH$_2$O;

B is (C$_1$-C$_6$)-alkyl, (C$_1$-C$_4$)-alkoxy-(C$_1$-C$_4$)-alkyl, 3- to 6-membered nonaromatic ring which may include 1 or 2 oxygen atoms, where the ring system may additionally be substituted by one or more of the following substituents: F, (C$_1$-C$_6$)-alkyl, O—(C$_1$-C$_8$)-alkyl, (C$_1$-C$_4$)-alkoxy-(C$_1$-C$_4$)-alkyl, oxo, hydroxyl, preferably (C$_1$-C$_6$)-alkyl or hydroxyl;

more preferably the combined element B-L2
selected from the group of

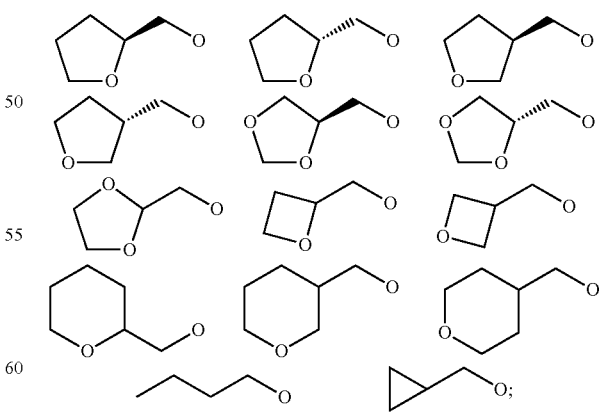

preferably

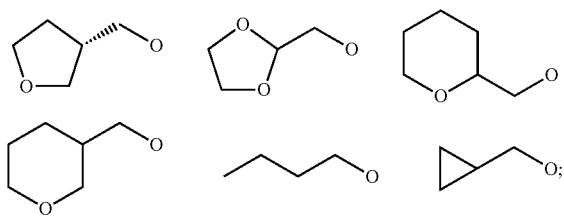

more preferably

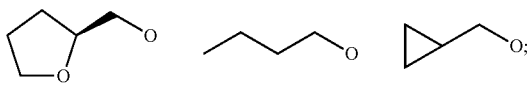

even more preferably

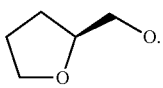

A further particular aspect of the present invention is that of compounds of the formula IIa

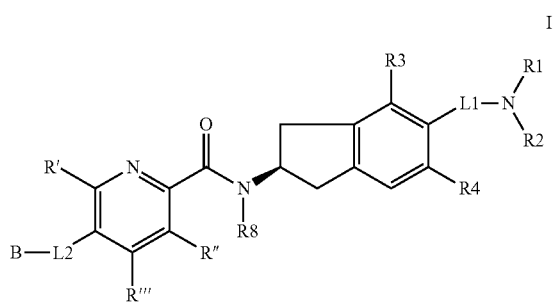

in which the variables R1, R2, L1, R3, R4, R8, R', R", L2 and B are each as defined for formula II.

In another particular aspect, the invention relates to compounds of the formula III

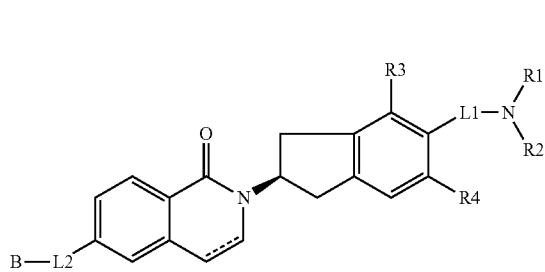

in which R1, R2, R3, R4, L1, L2 and B are each as defined for formula I. The broken line indicates an optional double bond, such that both dihydroisoquinolinones and isoquinolinones are embraced by the formula III.

In another particular aspect, the invention relates to co pounds of the formula IV

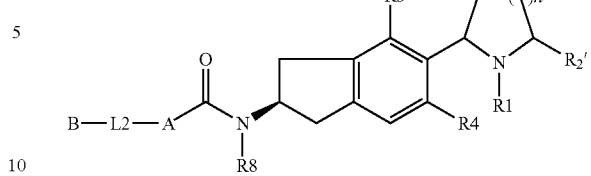

in which R1, R3, R4, R8, L2, A and B are each as defined for formula I.

n is 1 or 2; R2' is H, methyl or ethyl.

The inventive compounds of the formula I can be prepared analogously to processes known to those skilled in the art. Suitable processes for preparing the inventive compounds of the formula I are mentioned below by way of example (see especially methods A, B, C, D. E. F, G, H, I, J and schemes 1 to 3).

Preferred embodiments of the steps mentioned, just like the preparation of the starting substances used in the steps, are known to those skilled in the art and are mentioned by way of example in the schemes and methods mentioned, and also examples.

This invention further relates to the use of compounds of the formula I and pharmaceutical compositions thereof as MCH receptor ligands. The inventive MCH receptor ligands are suitable especially as modulators of the activity of MCH R1.

The role of MCH in regulating the energy balance has now been well documented (Qu. D. et al., Nature 1996, 380, 243-7; Shimada, M. et al. Nature 1998, 396, 670-4; Chen, Y et al. Endocrinology 2002, 143, 2469-77; Endocrinology 2003, 144, 4831-40; Reviews: G. Hervieu, Expert Opin. Ther. Targets 2003, 7, 495-511; Shi, Y., Peptides 2004, 25, 1605-11; Pissios, P. et al., Endocrine Rev. 2006, 27, 606-20); Luthin, D. R., Life Sci. 2007, 81, 423-440).

There are also indications that MCH antagonists can have a beneficial influence on centrally related disorders such as, for example, anxiety neuroses and depressions (Borowsky. B. et al. Nature Medicine 2002, 8, 825-30; Reviews: G. Hervieu, Expert Opin, Ther. Targets 2003, 7, 495-511; Chaki, S. et al., Drug Dev. Res. 2005, 65, 278-290; Dyck, B., Drug Dev. Res. 2005, 65, 291-300; Shimazaki, T., CNS Drugs 2006, 20, 801-11); Drugs Fut. 2007, 32, 809-822).

There are also indications of urological and inflammation applications of MCH antagonists: Hegde Laxminarayan G. Ping Xiao L1, Jochnowitz Nina, Craig Douglas A, The Journal of Pharmacology and Experimental Therapeutics (2009), 328(1), 165-73 and Kokkotou Efi, Moss Alan C., Torres Daniel, Karagiannides Iordanes, Cheifetz Adam, Liu Sumei, O'Brien Michael, Maratos-Flier Eleftheria, Pothoulakis Charalabos, Proceedings of the National Academy of Sciences of the United States of America (2008), 105(30), 10613-10618.

Compounds of this type are particularly suitable for the treatment and/or prevention of
1. Obesity
2. Diabetes mellitus, especially type 2 diabetes, including the prevention of the sequelae associated therewith,
  Particular aspects in this connection are
  improvement in hyperglycemia
  improvement in insulin resistance
  improvement in glucose tolerance
  protection of the pancreatic β cells prevention of macro- and microvascular disorders
3. Dyslipidemias and the sequelae thereof such as, for example, atherosclerosis, coronary heart disease, cerebrovascular disorders etc., especially (but not restricted to) those which are characterized by one or more of the following factors:
   high plasma triglyceride concentrations, high postprandial plasma triglyceride concentrations
   low HDL cholesterol concentration
4. Fatty liver, especially nonalcoholic fatty liver and variants thereof,
   steatosis
   steatohepatitis
   cirrhosis
5. Various other conditions which may be associated with the metabolic syndrome, such as:
   thromboses, hypercoagulable and prothrombotic stages (arterial and venous)
   high blood pressure
   heart failure, for example (but not restricted to) the state following myocardial infarction, hypertensive heart disease or cardiomyopathy
6. Psychiatric indications such as
   depressions
   anxiety states
   disturbances of the circadian rhythm
   affection disorders
   schizophrenia
   addictive disorders
7. Sleep disorders such as
   sleep apnea
   narcolepsy
   daytime sleepiness
   obesity hyperventilation syndrome
8. Inflammation disorders such as
   inflammatory bowel disease
   Crohn's disease
9. Urological disorders such as
   overactive bladder syndrome.

Compounds which have a favorable effect on more than one of the above-mentioned pathological states are preferred.

Formulations

The amount of a compound of formula I necessary to achieve the desired biological effect depends on a number of factors, for example the specific compound chosen, the intended use, the mode of administration and the clinical condition of the patient. The daily dose is generally in the range from 0.001 mg to 100 mg (typically from 0.01 mg to 50 mg) per day and per kilogram of body weight, for example 0.1-10 mg/kg/day. An intravenous dose may be, for example, in the range from 0.001 mg to 1.0 mg/kg, which can suitably be administered as infusion of 10 ng to 100 ng per kilogram and per minute. Suitable infusion solutions for these purposes may contain, for example, from 0.1 ng to 10 mg, typically from 1 ng to 10 mg, per milliliter. Single doses may contain, for example, from 1 mg to 10 g of the active ingredient. Thus, ampoules for injections may contain, for example, from 1 mg to 100 mg, and single-dose formulations which can be administered orally, such as, for example, tablets or capsules, may contain, for example, from 0.05 to 1000 mg, typically from 0.5 to 600 mg. For the therapy of the abovementioned conditions, the compounds of formula I may be used as the compound itself, but they are preferably in the form of a pharmaceutical composition with an acceptable carrier. The carrier must, of course, be acceptable in the sense that it is compatible with the other ingredients of the composition and is not harmful for the patient's health. The carrier may be a solid or a liquid or both and is preferably formulated with the compound as a single dose, for example as a tablet, which may contain from 0.05% to 95% by weight of the active ingredient. Other pharmaceutically active substances may likewise be present, including other compounds of formula I. The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case on the nature and severity of the condition to be treated and on the nature of the compound of formula I used in each case. Coated formulations and coated slow-release formulations also belong within the framework of the invention. Preference is given to acid- and gastric juice-resistant formulations. Suitable coatings resistant to gastric juice comprise cellulose acetate phthalate, polyvinyl acetate phthalate, hydroxypropylmethylcellulose phthalate and anionic polymers of methacrylic acid and methyl methacrylate.

Suitable pharmaceutical preparations for oral administration may be in the form of separate units such as, for example, capsules, cachets, suckable tablets or tablets, each of which contains a defined amount of at least one compound of formula I; as powders or granules; as solution or suspension in an aqueous or nonaqueous liquid; or as an oil-in-water or water-in-oil emulsion. These compositions may, as already mentioned, be prepared by any suitable pharmaceutical method which includes a step in which the active ingredient and the carrier (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, where appropriate with one or more additional ingredients. Compressed tablets can be produced by tableting the compound in free-flowing form such as, for example, a powder or granules, where appropriate mixed with a binder, glidant, inert diluent and/or one (or more) surface-active/dispersing agent(s) in a suitable machine. Molded tablets can be produced by molding the compound, which is in powder form and is moistened with an inert liquid diluent, in a suitable machine.

Pharmaceutical compositions which are suitable for peroral (sublingual) administration comprise suckable tablets which contain at least one compound of formula I with a flavoring, normally sucrose and gum arabic or tragacanth, and pastilles which comprise the compound in an inert base such as gelatin and glycerol or sucrose and gum arabic.

Pharmaceutical compositions suitable for parenteral administration comprise preferably sterile aqueous preparations of at least one compound of formula I, which are preferably isotonic with the blood of the intended recipient. These preparations are preferably administered intravenously, although administration may also take place by subcutaneous, intramuscular or intradermal injection. These preparations can preferably be produced by mixing the compound with water and making the resulting solution sterile and isotonic with blood. Injectable compositions of the invention generally contain from 0.1 to 5% by weight of the active compound.

Pharmaceutical compositions suitable for rectal administration are preferably in the form of single-dose suppositories.

These can be produced by mixing at least one compound of the formula I with one or more conventional solid carriers, for example cocoa butter, and shaping the resulting mixture.

Pharmaceutical compositions suitable for topical use on the skin are preferably in the form of ointment, cream, lotion, paste, spray, aerosol or oil. Carriers which can be used are petrolatum, lanolin, polyethylene glycols, alcohols and combinations of two or more of these substances. The active ingredient is generally present in a concentration of from 0.1 to 15% by weight of the composition, for example from 0.5 to 2%.

Transdermal administration is also possible. Pharmaceutical compositions suitable for transdermal uses can be in the form of single patches which are suitable for long-term close contact with the patient's epidermis. Such patches suitably contain the active ingredient in an aqueous solution which is buffered where appropriate, dissolved and/or dispersed in an adhesive or dispersed in a polymer. A suitable active ingredient concentration is about 1% to 35%, preferably about 3% to 15%. A particular possibility is for the active ingredient to be released by electrotransport or iontophoresis as described, for example, in Pharmaceutical Research, 2(6): 318 (1986).

The compounds of the formula I are distinguished by beneficial effects on lipid metabolism, and they are particularly suitable for weight reduction and for maintaining a reduced weight after weight reduction has taken place in mammals and as anorectic agents. The compounds are distinguished as selective MCH1R antagonists by their low toxicity, the small effect on metabolizing enzymes and their few side effects. In particular, preferred compounds of the invention are notable for low blockade of the hERG channel. In addition, preferred compounds of the formula I are noticeably soluble in aqueous systems and thus particularly suitable for pharmaceutical development. The pharmacological effect is moreover achieved in in vivo test models after oral administration from well-tolerated vehicles.

The compounds can be employed alone or in combination with other weight-reducing or anorectic active ingredients. Further anorectic active ingredients of this type are mentioned, for example, in the Rote Liste, chapter 01 under weight-reducing agents/appetite suppressants, and may also include active ingredients which increase the energy turnover of the organism and thus lead to weight reduction or else those which influence the general metabolism of the organism in such a way that an increased calorie intake does not lead to an enlargement of the fat depots and a normal calorie intake leads to a reduction of the fat depots of the organism. The compounds are suitable for the prophylaxis and, in particular, for the treatment of excessive weight or obesity. The compounds are further suitable for the prophylaxis and, in particular, for the treatment of type II diabetes, of arteriosclerosis and for normalizing lipid metabolism and for the treatment of high blood pressure.

Combinations with other Medicaments

The inventive compounds can be administered alone or in combination with one or more further pharmacologically active substances which have, for example, beneficial effects on metabolic disturbances or disorders frequently associated therewith. They can be combined with the inventive compounds of the formula I, in particular for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively.

Further suitable active ingredients for the combination preparations are:

All antidiabetics which are mentioned in the Rote Liste 2007, chapter 12; all weight-reducing agents/appetite suppressants which are mentioned in the Rote Liste 2007, chapter 1; all diuretics which are mentioned in the Rote Liste 2007, chapter 36; all lipid-lowering agents which are mentioned in the Rote Liste 2007, chapter 58. They can be combined with the inventive compound of the formula I, in particular for a synergistic improvement in action. The active ingredient combination can be administered either by separate administration of the active ingredients to the patient or in the form of combination products in which a plurality of active ingredients are present in one pharmaceutical preparation. When the active ingredients are administered by separate administration of the active ingredients, this can be done simultaneously or successively. Most of the active ingredients mentioned hereinafter are disclosed in the USP Dictionary of USAN and International Drug Names, US Pharmacopeia, Rockville 2006.

Antidiabetics include insulin and insulin derivatives, for example Lantus® (see www.lantus.com) or HMR 1964 or Levemir® (insulin detemir), Humalog® (Insulin Lispro), Humulin®, VIAject™, SuliXen®, VIAject™ or those as described in WO2005005477 (Novo Nordisk), fast-acting insulins (see U.S. Pat. No. 6,221,633), inhalable insulins, for example Exubera®, Nasulin™ or oral insulins, for example IN-105 (Nobex) or Oral-lyn™ (Generex Biotechnology), or Technosphere® insulin (MannKind) or Cobalamin™ oral insulin or ORMD-0801 or insulins or insulin precursors as described in WO2007128815, WO2007128817, WO2008034881, WO2008049711, WO2008145721, WO2009034117, WO2009060071, WO2009133099 or insulins which can be administered transdermally; additionally included are also those insulin derivatives which are bonded to albumin by a bifunctional linker, as described, for example, in WO2009121884;

GLP-1 derivatives and GLP-1 agonists, for example exenatide or specific formulations thereof, as described, for example, in WO2008061355, WO2009080024, WO2009080032, liraglutide, taspoglutide (R-1583), albiglutide, lixisenatide or those which have been disclosed in WO 98/08871, WO2005027978, WO2006037811, WO2006037810 by Novo Nordisk A/S. in WO 01/04156 by Zealand or in WO 00/34331 by Beaufour-Ipsen, pramlintide acetate (Symllin; Amylin Pharmaceuticals), inhalable GLP-1 (MKC-253 from MannKind) AVE-0010, BIM-51077 (R-1583, ITM-077), PC-DAC:exendin-4 (an exendin-4 analog which is bonded covalently to recombinant human albumin), biotinylated exendin (WO2009107900), a specific formulation of exendin-4 as described in US2009238879, CVX-73, CVX-98 and CVx-96 (GLP-1 analogs which are bonded covalently to a monoclonal antibody which has specific binding sites for the GLP-1 peptide), CNTO-736 (a GLP-1 analog which is bonded to a domain which includes the Fc portion of an antibody), PGC-GLP-1 (GLP-1 bonded to a nanocarrier), agonists or modulators, as described, for example, in D. Chen et al., Proc. Natl. Acad. Sci. USA 104 (2007) 943, those as described in WO2006124529, WO2007124461, WO2008062457, WO2008082274, WO2008101017, WO2008081418, WO2008112939, WO2008112941, WO2003113601, WO2008116294, WO2008116648, WO2008119238, WO2008148839, WO2008299096, WO2008152403, WO2009030738, WO2009030771, WO2009030774, WO2009035540, WO2009058734, WO2009111700, WO2009125424, WO2009129696, WO2009149148, peptides, for example obinepitide (TM- 30338), amylin receptor agonists, as described, for example, in WO2007104789, WO2009034119, analogs of the human GLP-1, as described in WO2007120899, WO2008022015, WO2008056726, chimeric pegylated peptides containing both GLP-1 and glucagon residues, as described, for example, in WO2008101017, and orally active hypoglycemic ingredients.

Antidiabetics additionally include poly- or monoclonal antibodies directed, for example, against interleukin 1 beta (IL-1β) for example XOMA-052.

Antidiabetics additionally include peptides which can bind to the human pro-islet peptide (HIP) receptor, as described, for example, in WO2009049222. Antidiabetics also include agonists of the glucose-dependent insulinotropic polypeptide (GIP) receptor, as described, for example, in WO2006121860.

Antidiabetics also include the glucose-dependent insulinotropic polypeptide (GIP), and also analogous compounds, as described, for example, in WO2008021560.

Additionally included are analogs and derivatives of human pancreatic polypeptide, as described, for example, in WO2009007714.

Antidiabetics additionally include encapsulated insulin-producing porcine cells, for example DiabeCell®.

Antidiabetics also include analogs and derivatives of fibroblast growth factor 21 (FGF-21), as described, for example, in WO2009149171.

The orally active hypoglycemic ingredients preferably include
sulfonylureas,
biguanidines,
meglitinides,
oxadiazolidinediones,
thiazolidinediones,
PPAR and RXR modulators,
glucosidase inhibitors,
inhibitors of glycogen phosphorylase,
glucagon receptor antagonists,
glucokinase activators,
inhibitors of fructose 1,6-bisphosphatase,
modulators of glucose transporter 4 (GLUT4),
inhibitors of glutamine-fructose-6-phosphate amidotransferase (GFAT).
GLP-1 agonists,
potassium channel openers, for example pinacidil, cromakalim, diazoxide, diazoxide choline salt, or those as described in R. D. Carr et al., Diabetes 52, 2003, 2513.2518, in J. B. Hansen et al., Current Medicinal Chemistry 11, 2004, 1595-1615, in T. M. Tagmose et al., J. Med. Chem. 47, 2004, 3202-3211 or in M. J. Coghlan et al., J. Med. Chem. 44, 2001, 1627-1653, or those which have been disclosed in WO 97/26265 and WO 99/03861 by Novo Nordisk A/S,
active ingredients which act on the ATP-dependent potassium channel of the beta cells, inhibitors of dipeptidyl peptidase-IV (DPP-IV),
insulin sensitizers,
inhibitors of liver enzymes involved in stimulating uconeogenesis and/or glycogenolysis,
modulators of glucose uptake, of glucose transport and of glucose reabsorption,
modulators of sodium-dependent glucose transporter 1 or 2 (SGLT1, SGLT2),
inhibitors of 11-beta-hydroxysteroid dehydrogenase-1 (11β-HSD1),
inhibitors of protein tyrosine phosphatase-1B (PTP-1B),
nicotinic acid receptor agonists,
inhibitors of hormone-sensitive or endothelial lipases,
inhibitors of acetyl-CoA carboxylase (ACC1 and/or ACC2) or
inhibitors of GSK-3 beta.

Also included are compounds which modify the lipid metabolism, such as active antihyperlipidemic ingredients and active antilipidemic ingredients,
HMGCoA reductase inhibitors,
farnesoid X receptor (FXR) modulators,
fibrates,
cholesterol reabsorption inhibitors,
CETP inhibitors,
bile acid reabsorption inhibitors,
MTP inhibitors,
agonists of estrogen receptor gamma (ERRγ agonists),
sigma-1 receptor antagonists,
antagonists of the somatostatin 5 receptor (SST5 receptor);
compounds which reduce food intake, and
compounds which increase thermogenesis.

In one embodiment of the invention, the compound of the formula I is administered in combination with insulin.

In another embodiment of the invention, the compound of the formula I is administered in combination with an insulin sensitizer, for example PN-2034 or ISIS-113715.

In one embodiment, the compound of the formula I is administered in combination with an active ingredient which acts on the ATP-dependent potassium channel of the beta cells, for example sulfonylureas, for example tolbutamide, glibenclamide, glipizide, gliclazide or glimepiride, or those preparations as described, for example, in EP2103302.

In one embodiment, the compound of the formula I is administered in combination with a tablet which comprises both glimepiride, which is released rapidly, and metformin, which is released over a longer period (as described, for example, in US2007264331, WO2008050987, WO2008062273).

In one embodiment, the compound of the formula I is administered in combination with a biguanide, for example metformin or one of its salts.

In a further embodiment, the compound of the formula I is administered in combination with a guanidine, for example benzylguanidine or one of its salts, or those guanidines as described in WO2009087395.

In another embodiment, the compound of the formula I is administered in combination with a meglitinide, for example repaglinide, nateglinide or mitiglinide.

In a further embodiment, the compound of the formula I is administered with a combination of mitiglinide with a glitazone, e.g. pioglitazone hydrochloride.

In a further embodiment, the compound of the formula I is administered with a combination of mitiglinide with an alpha-glucosidase inhibitor.

In a further embodiment, the compound of the formula I is administered in combination with antidiabetic compounds, as described in WO2007095462, WO2007101060, WO2007105650.

In a further embodiment, the compound of the formula I is administered in combination with antihypoglycemic compounds, as described in WO2007137008, WO2008020607.

In one embodiment, the compound of the formula I is administered in combination with a thiazolidinedione, for example troglitazone, ciglitazone, pioglitazone, rosiglitazone or the compounds disclosed in WO 97/41097 by Dr, Reddy's Research Foundation, especially 5-[[4-[(3,4-dihydro-3-methyl-4-oxo-2-quinazolinylmethoxy]phenyl]methyl]-2,4-thiazolidinedione.

In one embodiment of the invention, the compound of the formula I is administered in combination with a PPAR gamma agonist, for example rosiglitazone, pioglitazone, JTT-501, GI 262570, R-483, CS-011 (rivoglitazone), DRL-17564, DRF-2593 (balaglitazone), INT-131, T-2384, or those as described in WO2005086904, WO2007060992, WO2007100027, WO2007103252, WO2007122970, WO2007138485, WO2008006319, WO2008006969, WO2008010238, WO2008017398, WO2008028188, WO2008066356, WO2008084303, WO2008089461-WO2008089464, WO2008093639, WO2008096769, WO2008096820, WO2008096829, US2008194617, WO2008099944, WO2008108602, WO2008109334, WO2008110062, WO2008126731, WO2008126732, WO2008137105, WO2009005672, WO2009038681, WO2009046606, WO2009080821, WO2009083526, WO2009102226, WO2009128558, WO2009139340.

In one embodiment of the invention, the compound of the formula I is administered in combination with Competact™, a solid combination of pioglitazone hydrochloride with metformin hydrochloride.

In one embodiment of the invention, the compound of the formula I is administered in combination with Tandemact™, a solid combination of pioglitazone with glimepiride. In a further embodiment of the invention, the compound of the formula I is administered in combination with a solid combination of pioglitazone hydrochloride with an angiotensin II agonist, for example TAK-536.

In one embodiment of the invention, the compound of the formula I is administered in combination with a PPAR alpha agonist or mixed PPAR alpha/PPAR delta agonist, for example GW9578, GW-590735, K-111, LY-674, KRP-101, DRF-10945, LY-518674, CP-900691, BMS-687453, BMS-711939, or those as described in WO2001040207, WO2002096894, WO2005097076, WO2007056771, WO2007087448, WO2007089667, WO2007089557, WO2007102515, WO2007103252, JP2007246474, WO2007118963, WO2007118964, WO2007126043, WO2008006043, WO2008006044, WO2008012470, WO2008035359, WO2008087365, WO2008087366, WO2008087367, WO2008117982, JP2009023975, WO2009033561, WO2009047240, WO2009072581, WO2009080248, WO2009080242.

In one embodiment of the invention, the compound of the formula I is administered in combination with a mixed PPAR alpha/gamma agonist, for example naveglitazar, aleglitazar, LY-510929, ONO-5129, E-3030, AVE 8042, AVE 8134, AVE 0847, CKD-501 (lobeglitazone sulfate), MBX-213, KY-201, BMS-759509 or as described in WO 00/64888, WO 00/64876, WO03/020269, WO2004024726, WO2007099553, US2007276041, WO2007085135, WO2007085136, WO2007141423, WO2008016175, WO2008053331, WO2008109697, WO2008109700, WO2008108735, WO2009026657, WO2009026658 or in J. P. Berger et al., TRENDS in Pharmacological Sciences 28(5), 244-251, 2005.

In one embodiment of the invention, the compound of the formula I is administered in combination with a PPAR delta agonist, for example GW-501516, or as described in WO2006059744, WO2006084176, WO2006029699, WO2007039172-WO2007039178, WO2007071766, WO2007101864, US2007244094, WO2007119887, WO2007141423, US2008004281, WO2008016175, WO2008066356, WO2008071311, WO2008084962, US2008176861, WO2009012650, US2009137671, WO2009080223.

In one embodiment of the invention, the compound of the formula I is administered in combination with a pan-SPPARM (selective PPAR modulator alpha, gamma, delta), for example GFT-505, indeglitazar, or those as described in WO2008035359, WO2009072581.

In one embodiment, the compound of the formula I is administered in combination with metaglidasen or with MBX-2044 or other partial PPAR gamma agonists/antagonists.

In one embodiment, the compound of the formula I is administered in combination with an α-glucosidase inhibitor, for example miglitol or acarbose, or those as described, for example, in WO2007114532, WO2007140230, US2007287674, US2008103201, WO2008065796, WO2008082017, US2009076129.

In one embodiment, the compound of the formula I is administered in combination with an inhibitor of glycogen phosphorylase, for example PSN-357 or FR-258900, or those as described in WO2003084922, WO2004007455, WO2005073229-31, WO2005067932, WO2008062739, WO2008099000, WO2008113760, WO2009016118, WO2009016119, WO2009030715, WO2009045830, WO2009045831, WO2009127723.

In another embodiment, the compound of the formula I is administered in combination with an inhibitor of the interaction of liver glycogen phosphorylase with the protein PPP1R3 (GL subunit of glycogen-associated protein phosphatase 1 (PP1)), as described, for example, in WO2009030715.

In one embodiment, the compound of the formula I is administered in combination with glucagon receptor antagonists, for example A-770077 or NNC-25-2504 or as described in WO2004100875, WO2005065680, WO2006086488, WO2007047177, WO2007106181, WO2007111864, WO2007120270, WO2007120284, WO2007123581, WO2007136577, WO2008042223, WO2008098244, WO2009057784, WO2009058662, WO2009058734, WO2009110520, WO2009120530, WO2009140342.

In a further embodiment, the compound of the formula I is administered in combination with an antisense compound, e.g. ISIS-325568, which inhibits the production of the glucagon receptor.

In one embodiment, the compound of the formula I is administered in combination with activators of glucokinase, for example LY-2121260 (WO2004063179), PSN-105, PSN-110, GKA-50, or those as described, for example, in WO2004072031, WO2004072066, WO2005080360, WO2005044801, WO2006016194, WO2006058923, WO2006112549, WO2006125972, WO2007017549, WO2007017649, WO2007007910, WO2007007040-42, WO2007006760-61, WO2007006814, WO2007007886, WO2007028135, WO2007031739, WO2007041365, WO2007041366, WO2007037534, WO2007043638, WO2007053345, WO2007051846, WO2007051845, WO2007053765, WO2007051847, WO2007061923, WO2007075847, WO2007089512, WO2007104034, WO2007117381, WO2007122482, WO2007125103, WO2007125105, US2007281942, WO2008005914, WO2008005964, WO2008043701, WO2008044777, WO2008047821, US2008096877, WO2008050117, WO2008050101, WO2008059625, US2008146625, WO2008078674, WO2008079787, WO2008084043, WO2008084044, WO2008084872, WO2008089892, WO2008091770, WO2008075073, WO2008084043, WO2008084044, WO2008084872, WO2008084873, WO2008089892, WO2008091770, JP2008189659, WO2008104994, WO2008111473, WO2008116107, WO2008118718, WO2008120754, US2008280875, WO2008136428, WO2008136444, WO2008149382, WO2008154563, WO2008156174, WO2008156757, US2009030046, WO2009018065, WO2009023718, WO2009039944, WO2009042435, WO2009046784, WO2009046802, WO2009047798, WO2009063821, WO2009081782, WO2009082152, WO2009083553, WO2009091014, US2009181981, WO2009092432, WO2009099080, WO2009106203, WO2009106209, WO2009109270, WO2009125873, WO2009127544, WO2009127546, WO2009128481, WO2009133687, WO2009140624

In one embodiment, the compound of the formula I is administered in combination with an inhibitor of gluconeogenesis, as described, for example, in FR-225654, WO2008053446.

In one embodiment, the compound of the formula I is administered in combination with inhibitors of fructose 1,6-bisphosphatase (FBPase), for example MB-07729, CS-917 (MB-06322) or MB-07803, or those as described in WO2006023515, WO2006104030, WO2007014619, WO2007137962, WO2008019309, WO2008037628, WO2009012039, EP2058308, WO2009068467, WO2009068468.

In one embodiment, the compound of the formula I is administered in combination with modulators of glucose transporter 4 (GLUT4), for example KST-48 (D.-O. Lee et al.: Arzneim.-Forsch, Drug Res. 54 (12), 835 (2004)).

In one embodiment, the compound of the formula I is administered in combination with inhibitors of glutamine: fructose-6-phosphate amidotransferase (GFAT), as described, for example, in WO2004101528.

In one embodiment, the compound of the formula I is administered in combination with inhibitors of dipeptidyl peptidase-IV (DPP-IV), for example vildagliptin (LAF-237), sitagliptin (MK-0431), sitagliptin phosphate, saxagliptin (BMS-477118), GSK-823093, PSN-9301, SYR-322, SYR-619, TA-6666, TS-021, GRC-8200 (melogliptin), GW-825964X, KRP-104, DP-893, ABT-341, ABT-279 or another salt thereof, S-40010, S-40755, PF-00734200, B1-1356, PHX-1149, alogliptin benzoate, linagliptin, melogliptin, carmegliptin, or those compounds as described in WO2003074500, WO2003106456, WO2004037169, WO200450658, WO2005037828, WO2005058901, WO2005012312, WO2005/012308, WO2006039325, WO2006058064, WO2006015691, WO2006015701, WO2006015699, WO2006015700, WO2006018117, WO2006099943, WO2006099941, JP2006160733, WO2006071752, WO2006065826, WO2006078676, WO2006073167, WO2006068163, WO2006085685, WO2006090915, WO2006104356, WO2006127530, WO2006111261, US2006890898, US2006803357, US2006303661, WO2007015767 (LY-2463665), WO2007024993, WO2007029086, WO2007063928, WO2007070434, WO2007071738, WO2007071576, WO2007077508, WO2007087231, WO2007097931, WO2007099385, WO2007100374, WO2007112347, WO2007112669, WO2007113226, WO2007113634, WO2007115821, WO2007116092, US2007259900, EP1852108, US2007270492, WO2007126745, WO2007136603, WO2007142253, WO2007148185, WO2008017670, US2008051452, WO2008027273, WO2008028662, WO2008029217, JP2008031064, JP2008063256, WO2008033851, WO2008040974, WO2008040995, WO2008060488, WO2008064107, WO2008066070, WO2008077597, JP2008156318, WO2008087560, WO2008089636, WO2008093960, WO2008096841, WO2008101953, WO2008118848, WO2008119005, WO2008119208, WO2008120813, WO2008121506, WO2008130151, WO2008131149, WO2009003681, WO2009014676, WO2009025784, WO2009027276, WO2009037719, WO2009068531, WO2009070314, WO2009065298, WO2009082134, WO2009082881, WO2009084497, WO2009093269, WO2009099171, WO2009099172, WO2009111239, WO2009113423, WO2009116067, US2009247532.

In one embodiment, the compound of the formula I is administered in combination with Janumet™, a solid combination of sitagliptin phosphate with metformin hydrochloride.

In one embodiment, the compound of the formula I is administered in combination with Eucreas®, a solid combination of vildagliptin with metformin hydrochloride.

In a further embodiment, the compound of the formula I is administered in combination with a solid combination of alogliptin benzoate with pioglitazone.

In one embodiment, the compound of the formula I is administered in combination with a solid combination of a salt of sitagliptin with metformin hydrochloride.

In one embodiment, the compound of the formula I is administered in combination with a combination of a DPP-IV inhibitor with omega-3 fatty acids or omega-3 fatty acid esters, as described, for example, in WO2007128801.

In one embodiment, the compound of the formula I is administered in combination with a combination of a DPP-IV inhibitor with metformin hydrochloride, as described, for example, in WO2009121945.

In one embodiment, the compound of the formula I is administered in combination with a combination of a DPP-IV inhibitor with a GPR-119 agonist, as described, for example, in WO2009123992.

In one embodiment, the compound of the formula I is administered in combination with a combination of a DPP-1V inhibitor with miglitol, as described, for example, in WO2009139362.

In one embodiment, the compound of the formula I is administered in combination with a solid combination of a salt of sitagliptin with metformin hydrochloride.

In one embodiment, the compound of the formula I is administered in combination with a solid combination of aloplliptin benzoate with pioglitazone hydrochloride.

In one embodiment, the compound of the formula I is administered in combination with a substance which enhances insulin secretion, for example KCP-265 (WO2003097064), or those as described in WO2007026761, WO2008045484, US2008194617, WO2009109259, WO2009109341.

In one embodiment, the compound of the formula I is administered in combination with agonists of the glucose-dependent insulinotropic receptor (GDIR), for example APD-668.

In one embodiment of the invention, the compound of the formula I is administered in combination with an ATP citrate lyase inhibitor, for example SB-204990.

In one embodiment, the compound of the formula I is administered in combination with modulators of the sodium-dependent glucose transporter 1 and/or 2 (SGLT1, SGLT2), for example KGA-2727, T-1095, SGL-0010, AVE 2268, SAR 7226, SGL-5083, SGL-5085, SGL-5094, ISIS-388626, sergliflozin, dapagliflozin or remogliflozin etabonate, canagliflozin, or as described, for example, in WO2004007517, WO200452903, WO200452902, PCT/EP2005/005959, WO2005085237, JP2004359630, WO2005121161, WO2006018150, WO2006035796, WO2006062224, WO2006058597, WO2006073197, WO2006080577, WO2006087997, WO2006108842, WO2007000445, WO2007014895, WO2007080170, WO2007093610, WO2007126117, WO2007128480, WO2007129668, US2007275907, WO2007136116, WO2007143316, WO2007147478, WO2008001864, WO2008002824, WO2008013277, WO2008013280, WO2008013321, WO2008013322, WO2008016132, WO2008020011, JP2008031161, WO2008034859, WO2008042688, WO2008044762, WO2008046497, WO2008049923, WO2008055870, WO2008055940, WO2008069327, WO2008070609, WO2008071288, WO2008072726, WO2008083200, WO2008090209, WO2008090210, WO2008101586, WO2008101939, WO2008116179, WO2008116195, US2008242596, US2008287529, WO2009026537, WO2009049731, WO2009076550, WO2009084531, WO2009096503, WO2009100936, WO2009121939, WO2009124638, WO2009128421, WO2009135673 or by A. L. Handlon in Expert Opin. Ther. Patents (2005) 15(11), 1531-1540.

In a further embodiment of the invention, the compound of the formula I is administered in combination with a solid combination of an SGLT inhibitor with a DPP-IV inhibitor, as described in WO2009091082.

In one embodiment, the compound of the formula I is administered in combination with a stimulator of glucose transport, as described, for example, in WO2008136392, WO2008136393.

In one embodiment, the compound of the formula I is administered in combination with inhibitors of 11-beta-hydroxysteroid dehydrogenase-1 (11β-HSD1), for example BVT-2733, JNJ-25918646, INCB-13739, INCB-20817, D10-92 ((−)-ketoconazole) or those as described, for example, in WO200190090-94, WO200343999, WO2004112782, WO200344000, WO200344009, WO2004112779, WO2004113310, WO2004103980, WO2004112784, WO2003065983, WO2003104207, WO2003104208, WO2004106294, WO2004011410, WO2004033427, WO2004041264, WO2004037251, WO2004056744, WO2004058730, WO2004065351, WO2004089367, WO2004089380, WO2004089470-71, WO2004089896, WO2005016877, WO2005063247, WO2005097759, WO2006010546, WO2006012227, WO2006012173, WO2006017542, WO2006034804, WO2006040329, WO2006051662, WO2006048750, WO2006049952, WO2006048331, WO2006050908, WO2006024627, WO2006040329, WO2006066109, WO2006074244, WO2006078006, WO2006106423, WO2006132436, WO2006134481, WO2006134467, WO2006135795, WO2006136502, WO2006138508, WO2006138695, WO2006133926, WO2007003521, WO2007007688, US2007066584, WO2007029021, WO2007047625, WO2007051811, WO2007051810, WO2007057768, WO2007058346, WO2007061661, WO2007068330, WO2007070506, WO2007087150, WO2007092435, WO2007089683, WO2007101270, WO2007105753, WO2007107470, WO2007107550, WO2007111921, US2007207985, US2007208001, WO2007115935, WO2007118185, WO2007122411, WO2007124329, WO2007124337, WO2007124254, WO2007127688, WO2007127693, WO2007127704, WO2007127726, WO2007127763, WO2007127765, WO2007127901, US2007270424, JP2007291075, WO2007130898, WO2007135427, WO2007139992, WO2007144394, WO2007145834, WO2007145835, WO2007146761, WO2008000950, WO2008000951, WO2008003611, WO2008005910, WO2008006702, WO2008006703, WO2008011453, WO2008012532, WO2008024497, WO2008024892, WO2008032164, WO2008034032, WO2008043544, WO2008044656, WO2008046758, WO2008052638, WO2008053194, WO2008071169, WO2008074384, WO2008076336, WO2008076862, WO2008078725, WO2008087654, WO2008088540, WO2008099145, WO2008101885, WO2008101886, WO2008101907, WO2008101914, WO2008106128, WO2008110196, WO2008119017, WO2008120655, WO2008127924, WO2008130951, WO2008134221, WO2008142859, WO2008142986, WO2008157752, WO2009001817, WO2009010416, WO2009017664, WO2009020140, WO2009023180, WO2009023181, WO2009023664, WO2009026422, WO2009038064, WO2009045753, WO2009056881, WO2009059666, WO2009061498, WO2009063061, WO2009070497, WO2009074789, WO2009075835, WO2009088997, WO2009090239, WO2009094169, WO2009098501, WO2009100872, WO2009102428, WO2009102460, WO2009102761, WO2009106817, WO2009108332, WO2009112691, WO2009112845, WO2009114173, WO2009117109, US2009264401, WO2009118473, WO2009131669, WO2009132986, WO2009134384, WO2009134387, WO2009134392, WO2009134400, WO2009135581, WO2009138386.

In one embodiment, the compound of the formula I is administered in combination with inhibitors of protein tyrosine phosphatase-1B (PTP-1B), as described, for example, in WO200119830-31, WO200117516, WO2004506446, WO2005012295, WO2005116003, WO2005116003, WO2006007959, DE 10 2004 0605424 WO2007009911, WO2007028145, WO2007067612-615, WO2007081755, WO2007115058, US2008004325, WO2008033455, WO2008033931, WO2008033932, WO2008033934, WO2008089581, WO2008148744, WO2009032321, WO2009109999, WO2009109998.

In one embodiment of the invention, the compound of the formula I is administered in combination with an agonist of GPR109A (HM74A receptor agonists; NAR agonists (nicotinic acid receptor agonists)), for example nicotinic acid or "extended release niacin" in conjunction with MK-0524A (laropiprant) or MK-0524, or those compounds as described in WO2004041274, WO2006045565, WO2006045564, WO2006069242, WO2006085108, WO2006085112, WO2006085113, WO2006124490, WO2006113150, WO2007017261, WO2007017262, WO2007017265, WO2007015744, WO2007027532, WO2007092364, WO2007120575, WO2007134986, WO2007150025, WO2007150026, WO2008016968, WO2008051403, WO2008086949, WO2008091338, WO2008097535, WO2008099448, US2008234277, WO2008127591.

In another embodiment of the invention, the compound of the formula I is administered in combination with a solid combination of niacin with simvastatin.

In another embodiment of the invention, the compound of the formula I is administered in combination with nicotinic acid or "extended release niacin" in conjunction with MK-0524A (laropiprant).

In a further embodiment of the invention, the compound of the formula I is administered in combination with nicotinic acid or "extended release niacin" in conjunction with MK-0524A (laropiprant) and with simvastatin.

In one embodiment of the invention, the compound of the formula I is administered in combination with nicotinic acid or another nicotinic acid receptor agonist and a prostaglandin DP receptor antagonist, for example those as described in WO2008039882.

In another embodiment of the invention, the compound of the formula I is administered in combination with an agonist of GPR116, as described, for example, in WO2006067531, WO2006067532.

In one embodiment, the compound of the formula I is administered in combination with modulators of GPR40, as described, for example, in WO2007013689, WO2007033002, WO2007106469, US2007265332, WO2007123225, WO2007131619, WO2007131620, WO2007131621, US2007265332, WO2007131622, WO2007136572, WO2008001931, WO2008030520, WO2008030618, WO2008054674, WO2008054675, WO2008066097, US2008176912, WO2008130514, WO2009038204, WO2009039942, WO2009039943, WO2009048527, WO2009054479, WO2009058237, WO2009111056.

In one embodiment, the compound of the formula I is administered in combination with modulators of GPR119 (G-protein-coupled glucose-dependent insulinotropic receptor), for example PSN-119-1, PSN-821, PSN-119-2, MSX-2982 or those as described, for example, in WO2004065380, WO2005061489 (PSN-632408), WO2006083491, WO2007003960-62 and WO2007003964, WO2007035355, WO2007116229, WO2007116230, WO2008005569, WO2008005576, WO2008008887, WO2008008895, WO2008025798, WO2008025799, WO2008025800, WO2008070692, WO2008076243, WO200807692, WO2008081204, WO2008081205, WO2008081206, WO2008081207, WO2008081208, WO2008083238, WO2008085316, WO2008109702, WO2008130581, WO2008130584, WO2008130615, WO2008137435, WO2008137436, WO2009012275, WO2009012277, WO2009014910, WO2009034388, WO2009038974, WO2009050522, WO2009050523, WO2009055331, WO2009105715, WO2009105717, WO2009105722, WO2009106561, WO2009106565, WO2009117421, WO2009125434, WO2009126535, WO2009129036, US2009286812, WO2009143049.

In a further embodiment, the compound of the formula I is administered in combination with modulators of GPR120, as described, for example, in EP1688138, WO2008066131, WO2008066131, WO2008103500, WO2008103501, WO2008139879, WO2009038204.

In another embodiment, the compound of the formula I is administered in combination with antagonists of GPR105, as described, for example, in WO2009000087, WO2009070873.

In a further embodiment, the compound of the formula I is administered in combination with agonists of GPR43, for example ESN-282.

In one embodiment, the compound of the formula I is administered in combination with inhibitors of hormone-sensitive lipase (HSL) and/or phospholipases, as described, for example, in WO2005073199, WO2006074957, WO2006087309, WO2006111321, WO2007042178, WO2007119837, WO2008122352, WO2008122357, WO2009009287.

In one embodiment, the compound of the formula I is administered in combination with inhibitors of endothelial lipase, as described, for example, in WO2007110216.

In one embodiment, the compound of the formula I is administered in combination with a phospholipase A2 inhibitor, for example darapladib or A-002, or those as described in WO2008048866, WO20080488867, US2009062369.

In one embodiment, the compound of the formula I is administered in combination with myricitrin, a lipase inhibitor (WO2007119827).

In one embodiment, the compound of the formula I is administered in combination with an inhibitor of glycogen synthase kinase-3 beta (GSK-3 beta), as described, for example, in US2005222220, WO2005085230, WO2005111018, WO2003078403, WO2004022544, WO2003106410, WO2005058908, US2005038023, WO2005009997, US2005026984, WO2005000836, WO2004106343, EP1460075, WO2004014910, WO2003076442, WO2005087727, WO2004046117, WO2007073117, WO2007083978, WO2007120102, WO2007122634, WO2007125109, WO2007125110, US2007281949, WO2008002244, WO2008002245, WO2008016123, WO2008023239, WO2008044700, WO2008056266, WO2008057940, WO2008077138, EP1939191, EP1939192, WO2008078196, WO2008094992, WO2008112642, WO2008112651, WO2008113469, WO2008121063, WO2008121064, EP-1992620, EP-1992621, EP1992624, EP-1992625, WO2008130312, WO2009007029, EP2020232, WO2009017452, WO2009035634, WO2009035684, WO2009038385, WO2009095787, WO2009095788, WO2009095789, WO2009095792, WO2009145814, US2009291982.

In one embodiment, the compound of the formula I is administered in combination with an inhibitor of phosphoenolpyruvate carboxykinase (PEPCK), for example those as described in WO2004074288.

In one embodiment, the compound of the formula is administered in combination with an inhibitor of phosphoinositide kinase-3 (PI3K), for example those as described in WO2008027584, WO2008070150, WO2008125833, WO2008125835, WO2008125839, WO2009010530, WO2009026345, WO2009071888, WO2009071890, WO2009071895.

In one embodiment, the compound of the formula I is administered in combination with an inhibitor of serum/glucocorticoid-regulated kinase (SGK), as described, for example, in WO2006072354, WO2007093264, WO2008009335, WO2008086854, WO2008138448.

In one embodiment, the compound of the formula I is administered in combination with a modulator of the glucocorticoid receptor, as described, for example, in WO2008057855, WO2008057856, WO2008057857, WO2008057859, WO2008057862, WO2008059867, WO2008059866, WO2008059865, WO2008070507, WO2008124665, WO2008124745, WO2008146871, WO2009015067, WO2009040288, WO2009069736, WO2009149139.

In one embodiment, the compound of the formula I is administered in combination with a modulator of the mineralocorticoid receptor (MR), for example drospirenone, or those as described in WO2008104306, WO2008119918.

In one embodiment, the compound of the formula I is administered in combination with an inhibitor of protein kinase C beta (PKC beta), for example ruboxistaurin, or those as described in WO2008096260, WO2008125945.

In one embodiment, the compound of the formula I is administered in combination with an inhibitor of protein kinase D, for example doxazosin (WO2008088006).

In a further embodiment, the compound of the formula I is administered in combination with an activator/modulator of the AMP-activated protein kinase (AMPK), as described, for example, in WO2007062568, WO2008006432, WO2008016278, WO2008016730, WO2008020607, WO2008083124, WO2008136642, WO2009019445, WO2009019446, WO2009019600, WO2009028891, WO2009065131, WO2009076631, WO2009079921, WO2009100130, WO2009124636, WO2009135580

In one embodiment, the compound of the formula I is administered in combination with an inhibitor of ceramide kinase, as described, for example, in WO2007112914, WO2007149865.

In a further embodiment, the compound of the formula I is administered in combination with an inhibitor of MAPK-interacting kinase 1 or 2 (MNK1 or 2), as described, for example, in WO2007104053, WO2007115822, WO2008008547, WO2008075741.

In one embodiment, the compound of the formula I is administered in combination with inhibitors of "I-kappaB kinase" (IKK inhibitors), as described, for example, in WO2001000610, WO2001030774, WO2004022057, WO2004022553, WO2005097129, WO2005113544, US2007244140, WO2008099072, WO2008099073, WO2008099073, WO2008099074, WO2008099075, WO2009056693, WO2009075277, WO2009089042, WO2009120801.

In another embodiment, the compound of the formula I is administered in combination with inhibitors of NF-kappaB (NFKB) activation, for example salsalate. In a further embodiment, the compound of the formula I is administered in combination with inhibitors of ASK-1 (apoptosis signal-regulating kinase 1), as described, for example, in WO2008016131, WO2009123986.

In one embodiment of the invention, the compound of the formula I is administered in combination with an HMG-CoA reductase inhibitor such as simvastatin, fluvastatin, pravastatin, lovastatin, atorvastatin, cerivastatin, rosuvastatin, pitavastatin, L-659699, BMS-644950, NCX-6560, or those as described in US2007249583, WO2008083551, WO2009054682.

In a further embodiment of the invention, the compound of the formula I is administered in combination with a farnesoid X receptor (FXR) modulator, for example WAY-362450 or those as described in WO2003099821, WO2005056554, WO2007052843, WO2007070796, WO2007092751, JP2007230909, WO2007095174, WO2007140174, WO2007140183, WO2008000643, WO2008002573, WO2008025539, WO2008025540, JP2008214222, JP2008273847, WO2008157270, US2008299119, US2008300235, WO2009005998, WO2009012125, WO2009027264, WO2009062874, US2009131409, US2009137554, US2009163552, WO2009127321, EP2128158.

In another embodiment of the invention, the compound of the formula I is administered in combination with a ligand of the liver X receptor (LXR), as described, for example, in WO2007092965, WO2008041003, WO2008049047, WO2008065754, WO2008073825, US2008242677, WO2009020683, US2009030082, WO2009021868, US2009069373, WO2009024550, WO2009040289, WO2009086123, WO2009086129, WO2009086130, WO2009086138, WO2009107387, US2009247587, WO2009133692, WO2008138438.

In one embodiment of the invention, the compound of the formula I is administered in combination with a fibrate, for example fenofibrate, clofibrate, bezafibrate, or those as described in WO2008093655.

In one embodiment of the invention, the compound of the formula I is administered in combination with fibrates, for example the choline salt of fenofibrate (SLV-348; Trilipix™).

In one embodiment of the invention, the compound of the formula I is administered in combination with fibrates, for example the choline salt of fenofibrate (Trilipix™) and an HMG-CoA reductase inhibitor, for example rosuvastatin.

In a further embodiment of the invention, the compound of the formula I is administered in combination with bezafibrate and diflunisal.

In a further embodiment of the invention, the compound of the formula I is administered in combination with a solid combination of fenofibrate or a salt thereof with simvastatin, rosuvastatin, fluvastatin, lovastatin, cerivastatin, pravastatin, pitavastatin or atorvastatin.

In a further embodiment of the invention, the compound of the formula I is administered in combination with Synordia (R), a solid combination of fenofibrate with metformin.

In another embodiment of the invention, the compound of the formula I is administered in combination with a solid combination of metformin with an MTP inhibitor, as described in WO2009090210.

In one embodiment of the invention, the compound of the formula I is administered in combination with a cholesterol reabsorption inhibitor, for example ezetimibe, tiqueside, pamaqueside, FM-VP4 (sitostanol/campesterol ascorbyl phosphate; Forbes Medi-Tech, WO2005042692, WO2005005453), MD-0727 (Microbia Inc., WO2005021497, WO2005021495) or with compounds as described in WO2002066464, WO2005000353 (Kotobuki Pharmaceutical Co. Ltd.) or WO2005044256 or WO2005062824 (Merck & Co.) or WO2005061451 and WO2005061452 (AstraZeneca AB) and WO2006017257 (Phenomix) or WO2005033100 (Lipideon Biotechnology AG), or as described in WO2002050060, WO2002050068, WO2004000803, WO2004000804, WO2004000805, WO2004087655, WO2004097655, WO2005047248, WO2006086562, WO2006102674, WO2006116499, WO2006121861, WO2006122186, WO2006122216, WO2006127893, WO2006137794, WO2006137796, WO2006137782, WO2006137793, WO2006137797, WO2006137795, WO2006137792, WO2006138163, WO2007059871, US2007232688, WO2007126358, WO2008033431, WO2008033465, WO2008052658, WO2008057336, WO2008085300, WO2008104875, US2008280836, WO2008108486.

In one embodiment of the invention, the compound of the formula I is administered in combination with an NPC1L1 antagonist, for example those as described in WO2008033464, WO2008033465.

In one embodiment of the invention, the compound of the formula I is administered in combination with Vytorin™, a solid combination of ezetimibe with simvastatin.

In one embodiment of the invention, the compound of the formula I is administered in combination with a solid combination of ezetimibe with atorvastatin.

In one embodiment of the invention, the compound of the formula I is administered in combination with a solid combination of ezetimibe with fenofibrate.

In one embodiment of the invention, the further active ingredient is a diphenylazetidinone derivative, as described, for example, in U.S. Pat. Nos. 6,992,067 or 7,205,290.

In a further embodiment of the invention, the further active ingredient is a diphenylazetidinone derivative, as described, for example, in U.S. Pat. Nos. 6,992,067 or 7,205,290, combined with a statin, for example simvastatin, fluvastatin, pravastatin, lovastatin, cerivastatin, atorvastatin, pitavastatin or rosuvastatin.

In one embodiment of the invention, the compound of the formula I is administered in combination with a solid combination of lapaquistat, a squalene synthase inhibitor, with atorvastatin.

In a further embodiment of the invention, the compound of the formula I is administered in combination with a conjugate consisting of the HMGCoA reductase inhibitor atorvastatin with the renin inhibitor aliskiren (WO2009090158).

In one embodiment of the invention, the compound of the formula I is administered in combination with a CETP inhibitor, for example torcetrapib, anacetrapib or JTT-705 (dalcetrapib), or those as described in WO2006002342, WO2006010422, WO2006012093, WO2006073973, WO2006072362, WO2007088996, WO2007088999, US2007185058, US2007185113, US2007185154, US2007185182, WO2006097169, WO2007041494, WO2007090752, WO2007107243, WO2007120621, US2007265252, US2007265304, WO2007128568, WO2007132906, WO2008006257, WO2008009435, WO2008018529, WO2008058961, WO2008058967, WO2008059513, WO2008070496, WO2008115442, WO2008111604, WO2008129951, WO2008141077, US2009118287, WO2009062371, WO2009071509.

In one embodiment of the invention, the compound of the formula I is administered in combination with bile acid reabsorption inhibitors (inhibitors of the intestinal bile acid transporter (IBAT)) (see, for example, U.S. Pat. Nos. 6,245,744, 6,221,897 or WO00/61568), for example HMR 1741, or those as described in DE 10 2005 033099.1 and DE 10 2005 033100.9, DE 10 2006 053635, DE 10 2006 053637, WO2007009655-56, WO2008058628, WO2008058629, WO2008058630, WO2008058631.

In one embodiment, the compound of the formula I is administered in combination with agonists of GPBAR1 (G-protein-coupled bile acid receptor-1; TGR5), as described, for example, in US20060199795, WO2007110237, WO2007127505, WO2008009407, WO2008067219, WO2008067222, FR2908310, WO2008091540, WO2008097976, US2009054304, WO2009026241, WO2009146772.

In one embodiment, the compound of the formula I is administered in combination with modulators of histone deacetylase, for example ursodeoxycholic acid, as described in WO2009011420.

In one embodiment, the compound of the formula I is administered in combination with inhibitors/modulators of the TRPM5 channel (TRP cation channel M5), as described, for example, in WO2008097504, WO2009038722.

In one embodiment, the compound of the formula I is administered in combination with inhibitors/modulators of the TRPA1 channel (TRP cation channel A1), as described, for example, in US2009176883, WO2009089083, WO2009144548.

In one embodiment, the compound of the formula I is administered in combination with inhibitors/modulators of the TRPV3 channel (TRP cation channel V3), as described, for example, in WO2009084034, WO2009130560.

In one embodiment of the invention, the compound of the formula I is administered in combination with a polymeric bile acid adsorber, for example cholestyramine, colesevelam hydrochloride.

In one embodiment of the invention, the compound of the formula I is administered in combination with colesevelam hydrochloride and metformin or a sulfonylurea or insulin.

In one embodiment of the invention, the compound of the formula I is administered in combination with tocotrienol and insulin or an insulin derivative.

In one embodiment of the invention, the compound of the formula I is administered in combination with a chewing gum comprising phytosterols (Reductol™).

In one embodiment of the invention, the compound of the formula I is administered in combination with an inhibitor of the microsomal triglyceride transfer protein (MTP inhibitor), for example implitapide, BMS-201038, R-103757, AS-1552133, SLx-4090, AEGR-733, JTT-130, or those as described in WO2005085226, WO2005121091, WO2006010423, WO2006113910, WO2007143164, WO2008049806, WO2008049808, WO2008090198, WO2008100423, WO2009014674.

In a further embodiment of the invention, the compound of the formula I is administered in combination with a combination of a cholesterol absorption inhibitor, for example ezetimibe, and an inhibitor of the triglyceride transfer protein (MTP inhibitor), for example implitapide, as described in WO2008030382 or in WO2008079398.

In one embodiment of the invention, the compound of the formula I is administered in combination with an active antihypertriglyceridemic ingredient, for example those as described in WO2008032980.

In another embodiment of the invention, the compound of the formula I is administered in combination with an antagonist of the somatostatin 5 receptor (SST5 receptor), for example those as described in WO2006094682.

In one embodiment of the invention, the compound of the formula I is administered in combination with an ACAT inhibitor, for example avasimibe, SMP-797 or KY-382, or those as described in WO2008087029, WO2008087030, WO2008095189, WO2009030746, WO2009030747, WO2009030750, WO2009030752, WO2009070130, WO2009081957, WO2009081957.

In a further embodiment of the invention, the compound of the formula I is administered in combination with an inhibitor of liver carnitine palmitoyltransferase-1 (L-CPT1), as described, for example, in WO2007063012, WO2007096251 (ST-3473), WO2008015081, US2008103182, WO2008074692, WO2008145596, WO2009019199.

In another embodiment of the invention, the compound of the formula I is administered in combination with an inhibitor of carnitin O-palmitoyltransferase II (CPT2), as described, for example, in US2009270500, US2009270505, WO2009132978, WO2009132979.

In a further embodiment of the invention, the compound of the formula is administered in combination with a modulator of serine palmitoyltransferase (SPT), as described, for example, in WO2008031032, WO2008046071, WO2008083280, WO2008084300.

In one embodiment of the invention, the compound of the formula I is administered in combination with a squalene synthetase inhibitor, for example BMS-188494, TAK-475 (lapaquistat acetate), or as described in WO2005077907, JP2007022943, WO2008003424, WO2008132846, WO2008133288, WO2009136396.

In one embodiment of the invention, the compound of the formula I is administered in combination with ISIS-301012 (mipomersen), an antisense oligonucleotide which is capable of regulating the apolipoprotein B gene.

In one embodiment of the invention, the compound of the formula I is administered in combination with apolipoprotein (ApoB) SNALP, a therapeutic product which comprises an siRNA (directed against the ApoB gene).

In one embodiment of the invention, the compound of the formula I is administered in combination with a stimulator of the ApoA-1 gene, as described, for example, in WO2008092231.

In one embodiment of the invention, the compound of the formula I is administered in combination with an LDL receptor inducer (see U.S. Pat. No. 6,342,512), for example HMR1171, HMR1586, or those as described in WO2005097738, WO2008020607.

In another embodiment of the invention, the compound of the formula I is administered in combination with an HDL cholesterol-elevating agent, for example those as described in WO2008040651, WO2008099278, WO2009071099, WO2009086096, US2009247550.

In one embodiment of the invention, the compound of the formula I is administered in combination with an ABCA1 expression enhancer, as described, for example, in WO2006072393, WO2008062830, WO2009100326.

In one embodiment of the invention, the compound of the formula I is administered in combination with a lipoprotein lipase modulator, for example ibrolipim (NO-1886).

In one embodiment of the invention, the compound of the formula I is administered in combination with a lipoprotein (a) antagonist, for example gemcabene (CI-1027).

In one embodiment of the invention, the compound of the formula I is administered in combination with a lipase inhibitor, for example orlistat or cetilistat (ATL-962).

In one embodiment of the invention, the compound of the formula I is administered in combination with an adenosine A1 receptor agonist (adenosine A1 R), for example CVT-3619 or those as described, for example, in EP1258247, EP1375508, WO2008028590, WO2008077050, WO2009050199, WO2009080197, WO2009100827, WO2009112155

In one embodiment of the invention, the compound of the formula I is administered in combination with an adenosine A2B receptor agonist (adenosine A2B R), for example ATL-801.

In another embodiment of the invention, the compound of the formula I is administered in combination with a modulator of adenosine A2A and/or adenosine A3 receptors, as described, for example, in WO2007111954, WO2007121918, WO2007121921, WO2007121923, WO2008070661, WO2009010871.

In a further embodiment of the invention, the compound of the formula I is administered in combination with a ligand of the adenosine A1/A2B receptors, as described, for example, in WO2008064788, WO2008064789, WO2009080198, WO2009100827, WO2009143992.

In one embodiment of the invention, the compound of the formula I is administered in combination with an adenosine A2B receptor antagonist (adenosine A2B R), as described in US2007270433, WO2008027585, WO2008080461, WO2009037463, WO2009037467, WO2009037468, WO2009118759.

In one embodiment, the compound of the formula I is administered in combination with inhibitors of acetyl-CoA carboxylase (ACC1 and/or ACC2), for example those as described in WO199946262, WO200372197, WO2003072197, WO2005044814, WO2005108370, JP2006131559, WO2007011809, WO2007011811, WO2007013691, WO2007095601-603, WO2007119833, WO2008065508, WO2008069500, WO2008070609, WO2008072850, WO2008079610, WO2008088688, WO2008088689, WO2008088692, US2008171761, WO2008090944, JP2008179621, US2008200461, WO2008102749, WO2008103382, WO2008121592, WO2009082346, US2009253725, JP2009196966, WO2009144554, WO2009144555.

In another embodiment, the compound of the formula I is administered in combination with modulators of microsomal acyl-CoA:glycerol-3-phosphate acyltransferase 3 (GPAT3, described in WO2007100789) or with modulators of microsomal acyl-CoA:glycerol-3-phosphate acyltransferase 4 (GPAT4, described in WO2007100833).

In a further embodiment, the compound of the formula I is administered in combination with modulators of xanthine oxidoreductase (XOR).

In another embodiment, the compound of the formula I is administered in combination with inhibitors of soluble epoxide hydrolase (sEH), as described, for example, in WO2008051873, WO2008051875, WO2008073623, WO2008094869, WO2008112022, WO2009011872, WO2009049154, WO2009049157, WO2009049165, WO2009073772, WO2009097476, WO2009111207, WO2009129508.

In a further embodiment, the compound of the formula I is administered in combination with CART modulators (see "Cocaine-amphetamine-regulated transcript influences energy metabolism, anxiety and gastric emptying in mice" Asakawa, A. et al.: Hormone and Metabolic Research (2001), 33(9), 554-558);

NPY antagonists, for example {4-[(4-aminoquinazolin-2-ylamino)methyl]-cyclohexylmethyl}naphthalene-1-sulfonamide hydrochloride (CGP 71683A) or velneperit or those as described in WO2009110510;

NPY-5 receptor antagonists/receptor modulators, such as L-152804 or the compound "NPY-5-BY" from Banyu, or as described, for example, in WO2006001318, WO2007103295, WO2007125952, WO2008026563, WO2008026564, WO2008052769, WO2008092887, WO2008092888, WO2008092891 WO2008129007, WO2008134228, WO2009054434, WO2009095377, WO2009131096;

NPY-4 receptor antagonists, as described, for example, in WO2007038942;

NPY-2 receptor antagonists/modulators, as described, for example, in WO2007038943, WO2009006185, US2009099199, US2009099243, US2009099244, WO2009079593, WO2009079597;

peptide YY 3-36 (PYY3-36) or analogous compounds, for example CJC-1682 (PYY3-36 conjugated with human serum albumin via Cys34) or CJC-1643 (derivative of PYY3-36, which is conjugated in vivo to serum albumin), or those as described in WO2005080424, WO2006095166, WO2008003947, WO2009080608;

NPY-2 receptor agonists, as described, for example, in WO2009080608;

derivatives of the peptide obestatin, as described by WO2006096847;

CB1R (cannabinoid receptor 1) antagonists/inverse agonists, for example rimonabant, surinabant (SR147778), SLV-319 (ibipinabant), AVE-1625, taranabant (MK-0364) or salts thereof, otenabant (CP-945,598), rosonabant, V-24343 or those compounds as described in, for example, EP 0656354, WO 00/15609, WO2001/64632-64634, WO 02/076949, WO2005080345, WO2005080328, WO2005080343, WO2005075450, WO2005080357, WO200170700, WO2003026647-48, WO200302776, WO2003040107, WO2003007887, WO2003027069, U.S. Pat. No. 6,509,367, WO200132663, WO2003086288, WO2003087037, WO2004048317, WO2004058145, WO2003084930, WO2003084943, WO2004058744, WO2004013120, WO2004029204, WO2004035566, WO2004058249, WO2004058255, WO2004058727, WO2004069838, US20040214837, US20040214855, US20040214856, WO2004096209, WO2004096763, WO2004096794, WO2005000809, WO2004099157, US20040266845, WO2004110453, WO2004108728, WO2004000817, WO2005000820, US20050009870, WO200500974, WO2004111033-34, WO200411038-39, WO2005016286, WO2005007111, WO2005007628, US20050054679, WO2005027837, WO2005028456, WO20050063761-62, WO2005061509, WO2005077897, WO2006018662, WO2006047516, WO2006060461, WO2006067428, WO2006067443, WO2006087480, WO2006087476, WO2006100208, WO2006106054, WO2006111849, WO2006113704, WO2007009705, WO2007017124, WO2007017126, WO2007018459, WO2007018460, WO2007016460, WO2007020502, WO2007026215, WO2007028849, WO2007031720, WO2007031721, WO2007036945, WO2007038045, WO2007039740, US20070015810, WO2007046548, WO2007047737, WO2007057687, WO2007062193 WO2007064272, WO2007079681, WO2007084319, WO2007084450, WO2007086080, EP1816125, US2007213302, WO2007095513, WO2007096764, US2007254863, WO2007119001, WO2007120454, WO2007121687, WO2007123949, US2007259934, WO2007131219, WO2007133820, WO2007136571, WO2007136607, WO2007136571, U.S. Pat. No. 7,297, 710, WO2007138050, WO2007139464, WO2007140385, WO2007140439, WO2007146761, WO2007148061, WO2007148062, US2007293509, WO2008004698, WO2008017381, US2008021031, WO2008024284, WO2008031734, WO2008032164, WO2008034032, WO2008035356, WO2008036021, WO2008036022, WO2008039023, WO2998043544, WO2008044111, WO2008048648, EP1921072-A1, WO2008053341, WO2008056377, WO2008059207, WO2008059335, WO2008062424, WO2008068423, WO2008068424, WO2008070305, WO2008070306, WO2008074816, WO2008074982, WO2008075012, WO2008075013, WO2008075019, WO2008075118, WO2008076754, WO2008081009, WO2008084057, EP1944295, US2008090809, US2008090810, WO2008092816, WO2008094473, WO2008094476, WO2008099076, WO2008099139, WO2008101995, US2008207704, WO2008107179, WO2008109027, WO2008112674, WO2008115705, WO2008118414, WO2008119999, WO200812000, WO2008121257, WO2008127585, WO2008129157, WO2008130616, WO2008134300, US2008262066, US2008287505, WO2009005645, WO2009005646, WO2009005671, WO2009023292, WO2009023653, WO2009024819, WO2009033125, EP2042175, WO2009053548-WO2009053553, WO2009054923, WO2009054929, WO2009059264, WO2009073138, WO2009074782, WO2009075691, WO2009078498, WO2009087285, WO2009074782, WO2009097590, WO2009097995, WO2009097996, WO2009097998, WO2009097999, WO2009098000, WO2009106708, US2009239909, WO2009118473, US2009264436, US2009264476, WO2009130234, WO2009131814, WO2009131815, US2009286758, WO2009141532, WO2009141533.

cannabinoid receptor 1/cannabinoid receptor 2 (CB1, /CB2) modulating compounds, for example delta-9-tetrahydrocannabivarin, or those as described, for example, in WO2007001939, WO2007044215, WO2007047737, WO2007095513, WO2007096764, WO2007112399, WO2007112402, WO2008122618, WO2009007697, WO2009012227, WO2009087564, WO2009093018, WO2009095752, WO2009120660;

cannabinoid receptor 2 (CB2) modulating compounds, for example those as described, for example, in WO2008063625, WO2008157500, WO2009004171, WO2009032754, WO2009055357, WO2009061652, WO2009063495, WO2009067613, WO2009114566;

modulators of FAAH (fatty acid amide hydrolase), as described, for example, in WO2007140005, WO2008019357, WO2008021625, WO2008023720, WO2008030532, WO2008129129, WO2008145839, WO2008145843, WO2008147553, WO2008153752, WO2009011904, WO2009048101, WO2009084970, WO2009109504, WO2009109743, WO2009117444, WO2009127944, WO2009138416;

inhibitors of fatty acid synthase (FAS), as described, for example, in WO2008057585, WO2008059214, WO2008075064, WO2008075070, WO2008075077, WO2009079860;

inhibitors of LCE (long chain fatty acid elongase)/long chain fatty acid CoA ligase, as described, for example, in WO2008120653, WO2009038021, WO2009044788, WO2009081789, WO2009099086;

vanilloid-1 receptor modulators (modulators of TRPV1), as described, for example, in WO2007091948, WO2007129188, WO2007133637, WO2008007780, WO2008010061, WO2008007211, WO2008010061, WO2008015335, WO2008018827, WO2008024433, WO2008024438, WO2008032204, WO2008050199, WO2008059339, WO2008059370, WO2008066664, WO2008075150, WO2008090382, WO2008090434, WO2008093024, WO2008107543, WO2008107544, WO2008110863, WO2008125295, WO2008125296, WO2008125337, WO2008125342, WO2008132600, WO2008133973, WO2009010529, WO2009010824, WO2009016241, WO2009023539, WO2009038812, WO2009050348, WO2009055629, WO2009055749, WO2009064449, WO2009081222, WO2009089057, WO2009109710WO2009112677, WO2009112678, WO2009112679, WO2009121036, WO2009124551, WO2009136625;

modulators, ligands, antagonists or inverse agonists of the opioid receptors, for example GSK-982 or those as described, for example, in WO2007047397, WO2008021849, WO2008021851, WO2008032156, WO2008059335, WO2008125348, WO2008125349, WO2008142454, WO2009030962, WO2009103552, WO2009115257;

modulators of the "orphan opioid (ORL-1) receptor", as described, for example, in US2008249122, WO2008089201;

agonists of the prostaglandin receptor, for example bimatoprost or those compounds as described in WO2007111806;

MC4 receptor agonists (melanocortin-4 receptor agonists, MC4R agonists, for example N-[2-(3a-benzyl-2-methyl-3-oxo-2,3,3a,4,6,7-hexahydro-pyrazolo[4,3-c]pyridin-5-yl)-1-(4-chlorophenyl)-2-oxoethyl]-1-amino-1,2,3,4-tetrahydronaphthalene-2-carboxamide; (WO 01/91752)) or LB53280, LB53279, LB53278 or THIQ, MB243, RY764, CHIR-785, PT-141, MK-0493, or those as described in WO2005060985, WO2005009950, WO2004087159, WO2004078717, WO2004078716, WO2004024720, US20050124652, WO2005051391, WO2004112793, WOUS20050222014, US20050176728, US20050164914, US20050124636, US20050130988, US20040167201, WO2004005324, WO2004037797, WO2004089307, WO2005042516, WO2005040109, WO2005030797, US20040224901, WO200501921, WO200509184, WO2005000339, EP1460069, WO2005047253, WO2005047251, WO2005118573, EP1538159, WO2004072076, WO2004072077, WO2006021655-57, WO2007009894, WO2007015162, WO2007041061, WO2007041052, JP2007131570, EP-1842846, WO2007096186, WO2007096763, WO2007141343, WO2008007930, WO2008017852, WO2008039418, WO2008087186, WO2008087187, WO2008087189, WO2008087186-WO2008087190, WO2008090357, WO2008142319, WO2009015867, WO2009061411, US2009076029, US2009131465, WO2009071101, US2009305960, WO2009144432;

MC4 receptor modulators (melanocortin-4 receptor modulators), as described, for example, in WO2009010299, WO2009074157;

orexin receptor 1 antagonists (OX1R antagonists), orexin receptor 2 antagonists (OX2R antagonists) or mixed OX1R/OX2R antagonists (e.g. 1-(2-methylbenzoxazol-6-yl)-3-[1,5]naphthyridin-4-ylurea hydrochloride (SB-334867-A), or those as described, for example, in WO200196302, WO200185693, WO2004085403, WO2005075458, WO2006067224, WO2007085718, WO2007088276, WO2007116374, WO2007122591, WO2007126934, WO2007126935, WO2008008517, WO2008008518, WO2008008551, WO2008020405, WO2008026149, WO2008038251, US2008132490, WO2008065626, WO2008078291, WO2008087611, WO2008081399, WO2008108991, WO2008107335, US2008249125, WO2008147518, WO2008150364, WO2009003993, WO2009003997, WO2009011775, WO2009016087, WO2009020642, WO2009058238, US2009186920, US2009203736, WO2009092642, WO2009100994, WO2009104155, WO2009124956, WO2009133522);

histamine H3 receptor antagonists/inverse agonists (e.g. 3-cyclohexyl-1-(4,4-dimethyl-1,4,6,7-tetrahydroimidazo[4,5-c]pyridin-5-yl)propan-1-one oxalic acid salt (WO 00/63208), or those as described in WO200064884, WO2005082893, WO2005123716, US2005171181 (e.g. PF-00389027), WO2006107661, WO2007003804, WO2007016496, WO2007020213, WO2007049798, WO2007055418, WO2007057329, WO2007062999, WO2007065820, WO2007068620, WO2007068641, WO2007075629, WO2007080140, WO2007082840, WO2007088450, WO2007088462, WO2007094962, WO2007099423, WO2007100990, WO2007105053, WO2007106349, WO2007110364, WO2007115938, WO2007131907, WO2007133561, US2007270440, WO2007135111, WO2007137955, US2007281923, WO2007137968, WO2007138431, WO2007146122, WO2008005338, WO2008012010, WO2008015125, WO2008045371, EP1757594, WO2008068173, WO2008068174, US20080171753, WO2008072703, WO2008072724, US2008188484, US2008188486, US2008188487, WO2008109333, WO2008109336, WO2008126886, WO2008154126, WO2008151957, US2008318952, WO2009003003, WO2009013195, WO2009036132, WO2009039431, WO2009045313, WO2009058300, WO2009063953, WO2009067401, WO2009067405, WO2009067406, US2009163464, WO2009100120, WO2009105206, WO2009121812, WO2009126782);

histamine H1/histamine H3 modulators, for example betahistine or its dihydrochloride;

modulators of the histamine H3 transporter or of the histamine H3/serotonin transporter, as described, for example, in WO2008002816, WO2008002817, WO2008002818, WO2008002820;

modulators of vesicular monoamine transporter 2 (VMAT2), as described, for example, in WO2009126305;

histamine H4 modulators, as described, for example, in WO2007117399, US2009156613;

CRF antagonists (e.g. [2-methyl-9-(2,4,6-trimethylphenyl)-9H-1,3,9-triazafluoren-4-yl]dipropylamine (WO 00/66585) or those CRF1 antagonists as described in WO2007105113, WO2007133756, WO2008036541, WO2008036579, WO2008083070);

CRF BP antagonists (e.g. urocortin);

urocortin agonists;

modulators of the beta-3 adrenoceptor, for example 1-(4-chloro-3-methanesulfonylmethylphenyl)-2-[2-(2,3-dimethyl-1H-indol-6-yloxy)ethylamino]ethanol hydrochloride (WO 01/83451) or solabegron (GW-427353) or N-5984 (KRP-204), or those as described in JP2006111553, WO2002038543, WO2002038544, WO2007048840-843, WO2008015558, EP1947103, WO2008132162;

MSH (melanocyte-stimulating hormone) agonists;

MCH (melanine-concentrating hormone) receptor antagonists (for example NBI-845, A-761, A-665798, A-798, ATC-0175, T-226296, T-71 (AMG-071, AMG-076), GW-856464, NGD-4715, ATC-0453, ATC-0759, GW-803430, or those compounds as described in WO2005085200, WO2005019240, WO2004011438, WO2004012648, WO2003015769, WO2004072025, WO2005070898, WO2005070925, WO2004039780, WO2004092181, WO2003033476, WO2002006245, WO2002089729, WO2002002744, WO2003004027, FR2868780, WO2006010446, WO2006038680, WO2006044293, WO2006044174, JP2006176443, WO2006018280, WO2006018279, WO2006118320, WO2006130075, WO2007018248, WO2007012661, WO2007029847, WO2007024004, WO2007039462, WO2007042660, WO2007042668, WO2007042669, US2007093508, US2007093509, WO2007048802, JP2007091649, WO2007092416; WO2007093363-366, WO2007114902, WO2007114916, WO2007141200, WO2007142217, US2007299062, WO2007146758, WO2007146759, WO2008001160, WO2008016811, WO2008020799, WO2008022979, WO2008038692, WO2008041090, WO2008044632, WO2008047544, WO2008061109, WO2008065021, WO2008068265, WO2008071646, WO2008076562, JP2008088120, WO2008086404, WO2008086409, US2008269110, WO2008140239, WO2009021740, US2009011994, US2009082359, WO2009041567, WO2009076387, WO2009089482, WO2009103478, WO2009119726, WO2009120655, WO2009123194, WO2009137270, WO2009146365);

CCK-A (CCK-1) agonists/modulators (for example {2-[4-(4-chloro-2,5-dimethoxy-phenyl)-5-(2-cyclohexylethyl)thiazol-2-ylcarbamoyl]-5,7-dimethylindol-1-yl}acetic acid trifluoroacetic acid salt (WO 99/15525) or SR-146131 (WO 0244150) or SSR-125180), or those as described in WO2005116034, WO2007120655, WO2007120688, WO2007120718, WO2008091631;

serotonin reuptake inhibitors (e.g. dexfenfluramine), or those as described in WO2007148341, WO2008034142, WO2008081477, WO2008120761, WO2008141081, WO2008141082, WO2008145135, WO2008150848, WO2009043834, WO2009077858;

mixed serotonin/dopamine reuptake inhibitors (e.g. bupropion), or those as described in WO2008063673, or solid combinations of bupropion with naltrexone or bupropion with zonisamide;

mixed reuptake inhibitors, for example DOV-21947 or those as described in WO2009016214, WO2009016215, WO2009077584, WO2009098208, WO2009098209, WO2009106769, WO2009109517, WO2009109518, WO2009109519, WO2009109608, WO2009145357, WO2009149258;

mixed serotoninergic and noradrenergic compounds (e.g. WO 00/71549);

5-HT receptor agonists, for example 1-(3-ethylbenzofuran-7-yl)piperazine oxalic acid salt (WO 01/09111);

mixed dopamine/norepinephrine/acetylcholine reuptake inhibitors (e.g. tesofensine), or those as described, for example, in WO2006085118, WO2008150480;

dopamine antagonists, as described, for example, in WO2008079838, WO2008079839, WO2008079847, WO2008079848;

norepinephrine reuptake inhibitors, as described, for example, in US2008076724, WO2009062318;

5-HT1A receptor modulators, as described, for example, in WO2009006227, WO2009137679, WO2009137732;

5-HT2A receptor antagonists, as described, for example, in WO2007138343;

5-HT2C receptor agonists (for example lorcaserine hydrochloride (APD-356) or BVT-933, or those as described in WO200077010, WO200077001-02, WO2005019180, WO2003064423, WO200242304, WO2005035533, WO2005082859, WO2006004937, US2006025601, WO2006028961. WO2006077025, WO2006103511, WO2007028132, WO2007084622, US2007249709; WO2007132841, WO2007140213, WO2008007661, WO2008007664, WO2008009125, WO2008010073, WO2008108445, WO2009063991, WO2009063992, WO2009063993, WO2009079765);

5-HT6 receptor modulators, for example E-6837, BVT-74316 or PRX-07034, or those as described, for example, in WO2005058858, WO2007054257, WO2007107373, WO2007108569, WO2007108742-744, WO2008003703, WO2008027073, WO2008034815, WO2008054288, EP1947085, WO2008084491, WO2008084492, WO2008092665, WO2008092666, WO2008101247, WO2008110598, WO2008116831, WO2008116833, WO2008136017, WO2008147812, EP2036888, WO2009013010, WO2009034581, WO2009053997, WO2009056632, WO2009073118, WO2009115515, WO2009135925, WO2009135927;

agonists of estrogen receptor gamma (ERRγ agonists), as described, for example, in WO2007131005, WO2008052709;

agonists of estrogen receptor alpha (ERRγ/ERR1 agonists), as described, for example, in WO2008109727;

agonists of estrogen receptor beta (ERRβ agonists), as described, for example, in WO2009055734, WO2009100335, WO2009127686;

sigma-1 receptor antagonists, as described, for example, in WO2007098953, WO2007098961, WO2008015266, WO2008055932, WO2008055933, WO2009071657;

muscarin 3 receptor (M3R) antagonists, as described, for example, in WO2007110782, WO2008041184;

bombesin receptor agonists (BRS-3 agonists), as described, for example, in WO2008051404, WO2008051405, WO2008051406, WO2008073311;

galanin receptor antagonists;

growth hormone (e.g. human growth hormone or AOD-9604);

growth hormone releasing compounds (tert-butyl 6-benzyloxy-1-(2-diisopropylaminoethylcarbamoyl)-3,4-dihydro-1H-isoquinoline-2-carboxylate (WO 01/85695));

growth hormone secretagogue receptor antagonists (ghrelin antagonists), for example A-778193, or those as described in WO2005030734, WO2007127457, WO2008008286, WO2009056707;

growth hormone secretagogue receptor modulators (ghrelin modulators), for example JMV-2959, JMV-3002, JMV-2810, JMV-2951, or those as described in WO2006012577 (e.g. YIL-781 or YIL-870), WO2007079239, WO2008092681, WO2008145749, WO2008148853, WO2008148854, WO2008148856, WO2009047558, WO2009071283, WO2009115503;

TRH agonists (see, for example, EP 0 462 884);

decoupling protein 2 or 3 modulators (as described, for example, in WO2009128583); chemical decouplers (e.g. WO2008059023, WO2008059024, WO2008059025, WO2008059026);

leptin receptor agonists (see, for example, Lee, Daniel W.; Leinung, Matthew C.; Rozhayskaya-Arena, Marina; Grasso, Patricia. Leptin agonists as a potential approach to the treatment of obesity. Drugs of the Future (2001), 26(9), 873-881);

leptin receptor modulators, as described, for example, in WO2009019427, WO2009071658, WO2009071668, WO2009071677, WO2009071678, WO2009147211, WO2009147216, WO2009147219, WO2009147221;

DA agonists (bromocriptin, bromocriptin mesylate, doprexin) or those as described in US2009143390;

lipase/amylase inhibitors (e.g. WO 00/40569, WO2008107184, WO2009049428, WO2009125819);

inhibitors of diacylglycerol O-acyltransferases (DGATs), for example BAY-74-4113, or as described, for example, in US2004/0224997, WO2004094618, WO200058491, WO2005044250, WO2005072740, JP2005206492, WO2005013907, WO2006004200, WO2006019020, WO2006064189, WO2006082952, WO2006120125, WO2006113919, WO2006134317, WO2007016538, WO2007060140, JP2007131584, WO2007071966, WO2007126957, WO2007137103, WO2007137107, WO2007138304, WO2007138311, WO2007141502, WO2007141517, WO2007141538, WO2007141545, WO2007144571, WO2008011130, WO2008011131, WO2008039007, WO2008048991, WO2008067257, WO2008099221, WO2008129319, WO2008141976, WO2008148840, WO2008148849, WO2008148851, WO2008148868, WO2009011285, WO2009016462, WO2009024821, US2009076275, WO2009040410, WO2009071483, WO2009081195, WO2009119534, WO2009126624, WO2009126861;

inhibitors of monoacylglycerol acyltransferase (2-acylglycerol O-acyltransferase; MGAT), as described, for example, in WO2008038768;

inhibitors of fatty acid synthase (FAS), for example 075, or those as described in WO2004005277, WO2008006113;

inhibitors of stearoyl-CoA delta9 desaturase (SCD1), as described, for example, in WO2007009236, WO2007044085, WO2007046867, WO2007046868, WO20070501124, WO2007056846, WO2007071023, WO2007130075, WO2007134457, WO2007136746, WO2007143597, WO2007143823, WO2007143824, WO2008003753, WO2008017161, WO2008024390, WO2008029266, WO2008036715, WO2008043087, WO2008044767, WO2008046226, WO2008056687, WO2008062276, WO2008064474, WO2008074824, WO2008074832, WO2008074833, WO2008074834, WO2008074835, WO2008089580, WO2008096746, WO2008104524, WO2008116898, US2008249100, WO2008120744, WO2008120759, WO2008123469, WO2008127349, WO2008128335, WO2008135141 WO2008139845, WO2008141455, US20080255130, US2008255161, WO2008141455, WO2009010560, WO2009016216, WO2009012573, WO2009024287, JP2009019013, WO2009037542, WO2009056556, WO2009060053, WO2009060054, WO2009070533, WO2009073973, WO2009103739, WO2009117659, WO2009117676, US2009253693, US2009253738, WO2009124259, WO2009126123, WO2009126527, WO2009129625, WO2009137201;

inhibitors of fatty acid desaturase 1 (delta5 desaturase), as described, for example, in WO2008089310;

inhibitors of monoglyceride lipase (MGL), as described in WO2008145842;

hypoglycemic/hypertriglyceridemic indoline compounds, as described in WO2008039087, WO2009051119;

inhibitors of "adipocyte fatty acid-binding protein aP2", for example BMS-309403 or those as described in WO2009028248;

activators of adiponectin secretion, as described, for example, in WO2006082978, WO2008105533, WO2008136173;

promoters of adiponectin production, as described, for example, in WO2007125946, WO2008038712;

modified adiponectins, as described, for example, in WO2008121009;

oxyntomodulin or analogs thereof (for example, TKS-1225);

oleoyl-estrone or agonists or partial agonists of the thyroid hormone receptor (thyroid hormone receptor agonists), for example: KB-2115 (eprotirome), QRX-431 (sobetirome) or DITPA, or those as described in WO20058279, WO200172692, WO200194293, WO2003084915, WO2004018421, WO2005092316, WO2007003419, WO2007009913, WO2007039125, WO2007110225, WO2007110226, WO2007128492, WO2007132475, WO2007134864, WO2008001959, WO2008106213, JP2009155261;

or agonists of the thyroid hormone receptor beta (TR-beta), for example MB-07811 or MB-07344, or those as described in WO2008062469.

In one embodiment of the invention, the compound of the formula I is administered in combination with a combination of eprotirome with ezetimibe.

In one embodiment of the invention, the compound of the formula I is administered in combination with an inhibitor of site-1 protease (S1P), for example PF-429242.

In a further embodiment of the invention, the compound of the formula I is administered in combination with a modulator of the "trace amine associated receptor 1" (TAAR1), as described, for example, in US2008146523, WO2008092785.

In one embodiment of the invention, the compound of the formula I is administered in combination with an inhibitor of growth factor receptor bound protein 2 (GRB2), as described, for example, in WO2008067270.

In a further embodiment of the invention, the compound of the formula I is administered in combination with an RNAi (siRNA) therapeutic agent directed against PCSK9 (proprotein convertase subtilisin/kexin type 9).

In one embodiment, the compound of the formula I is administered in combination with Omacor® or Lovaza™ (omega-3 fatty acid ester; highly concentrated ethyl ester of eicosapentaenoic acid and of docosahexaenoic acid).

In one embodiment, the compound of the formula I is administered in combination with lycopene.

In one embodiment of the invention, the compound of the formula I is administered in combination with an antioxidant, for example OPC-14117, AGI-1067 (succinobucol), probu- col, tocopherol, ascorbic acid, β-carotene or selenium, or those as described in WO2009135918.

In one embodiment of the invention, the compound of the formula I is administered in combination with a vitamin, for example vitamin B6 or vitamin 812.

In one embodiment, the compound of the formula I is administered in combination with more than one of the aforementioned compounds, for example in combination with a sulfonylurea and metformin, a sulfonylurea and acarbose, repaglinide and metformin (PrandiMet™), insulin and a sulfonylurea, insulin and metformin, insulin and troglitazone, insulin and lovastatin, etc.

In a further embodiment, the compound of the formula I is administered in combination with an activator of soluble guanylate cyclase (sGC), as described, for example, in WO2009032249.

In another embodiment, the compound of the formula I is administered in combination with an inhibitor of carboanhydrase type 2 (carbonic anhydrase type 2), for example those as described in WO2007065948, WO2009050252.

In another embodiment, the compound of the formula I is administered in combination with topiramat or a derivative thereof, as described in WO2008027557.

In a further embodiment, the compound of the formula I is administered in combination with a solid combination of topiramat with phentermin (Qnexa™).

In a further embodiment, the compound of the formula I is administered in combination with an antisense compound, e.g. ISIS-377131, which inhibits the production of the glucocorticoid receptor.

In another embodiment, the compound of the formula I is administered in combination with an aldosterone synthase inhibitor and an antagonist of the glucocorticoid receptor, a cortisol synthesis inhibitor and/or an antagonist of the corticotropin releasing factor, as described, for example, in EP1886695, WO2008119744.

In one embodiment, the compound of the formula I is administered in combination with an agonist of the RUP3 receptor, as described, for example, in WO2007035355, WO2008005576.

In another embodiment, the compound of the formula I is administered in combination with an activator of the gene which codes for ataxia telangiectasia mutated (ATM) protein kinase, for example chloroquine.

In one embodiment, the compound of the formula I is administered in combination with a tau protein kinase 1 inhibitor (TPK1 inhibitor), as described, for example, in WO2007119463, WO2009035159, WO2009035162.

In one embodiment, the compound of the formula I is administered in combination with a "c-Jun N-terminal kinase" inhibitor (JNK inhibitor), for example B1-78D3 or those as described, for example, in WO2007125405, WO2008028860, WO2008118626.

In one embodiment, the compound of the formula I is administered in combination with an endothelin A receptor antagonist, for example avosentan (SPP-301).

In one embodiment, the compound of the formula I is administered in combination with inhibitors of neutral endopeptidase (NEP inhibitors), as described, for example, in WO2009138122, WO2009135526.

In one embodiment, the compound of the formula I is administered in combination with modulators of the glucocorticoid receptor (GR), for example KB-3305 or those compounds as described, for example, in WO2005090336, WO2006071609, WO2006135826, WO2007105766, WO2008120661, WO2009040288, WO2009058944, WO2009108525, WO2009111214

In one embodiment, the further active ingredient is varenicline tartrate, a partial agonist of the alpha 4-beta 2 nicotinic acetylcholine receptor.

In one embodiment, the further active ingredient is an agonist of the alpha 7-nicotonic acetylcholine receptor, as described, for example, in WO2009018551, WO2009071519, WO2009071576, WO2009071577.

In one embodiment, the further active ingredient is trodusquemine.

In one embodiment, the further active ingredient is a modulator of the enzyme SIRT1 and/or SIRT3 (an NAD$^+$-dependent protein deacetylase); this active ingredient may, for example, be resveratrol in suitable formulations, or those compounds as specified in WO2007019416 (e.g. SRT-1720), WO2008073451, WO2008156866, WO2008156869, WO2009026701, WO2009049018, WO2009058348, WO2009061453, WO2009134973, WO2009146358.

In one embodiment of the invention, the further active ingredient is DM-71 (N-acetyl-L-cysteine with bethanechol).

In one embodiment, the compound of the formula I is administered in combination with antihypercholesterolemic compounds, as described, for example, in WO2007107587, WO2007111994, WO2008106600, WO2008113796, US2008280836, WO2009113952.

In a further embodiment, the compound of the formula I is administered in combination with inhibitors of SREBP (sterol regulatory element-binding protein), for example fatostatin, or those as described, for example, in WO2008097835.

In another embodiment, the compound of the formula I is administered in combination with a cyclic peptide agonist of the VPAC2 receptor, as described, for example, in WO2007101146, WO2007133828.

In a further embodiment, the compound of the formula I is administered in combination with an agonist of the endothelin receptor, as described, for example, in WO2007112069.

In a further embodiment, the compound of the formula I is administered in combination with AKP-020 (bis(ethylmaltolato)oxovanadium(IV)).

In another embodiment, the compound of the formula I is administered in combination with tissue-selective androgen receptor modulators (SARM), as described, for example, in WO2007099200, WO2007137874.

In a further embodiment, the compound of the formula I is administered in combination with an AGE (advanced glycation endproduct) inhibitor, as described, for example, in JP2008024673.

In one embodiment of the invention, the further active ingredient is leptin; see, for example, "Perspectives in the therapeutic use of leptin", Salvador, Javier; Gomez-Ambrosi, Javier; Fruhbeck, Gema, Expert Opinion on Pharmacotherapy (2001), 2(10), 1615-1622.

In another embodiment of the invention, the further active ingredient is metreleptin (recombinant methionyl-leptin) combined with pramlintide.

In a further embodiment of the invention, the further active ingredient is the tetrapeptide ISF-402.

In one embodiment, the further active ingredient is dexamphetamine or amphetamine.

In one embodiment, the further active ingredient is fenfluramine or dexfenfluramine.

In another embodiment, the further active ingredient is sibutramine or those derivatives as described in WO2008034142.

In one embodiment, the further active ingredient is mazindol or phentermin.

In a further embodiment, the further active ingredient is geniposidic acid (WO2007100104) or derivatives thereof (JP2008106008).

In another embodiment, the further active ingredient is a neuropeptide FF2 agonist, as described, for example, in WO2009038012.

In one embodiment, the further active ingredient is a nasal calcium channel blocker, for example diltiazem, or those as described in U.S. Pat. No. 7,138,107.

In one embodiment, the further active ingredient is an inhibitor of sodium-calcium ion exchange, for example those as described in WO2008028958, WO2008085711.

In a further embodiment, the further active ingredient is a blocker of calcium channels, for example of CaV3.2 or CaV2.2, as described in WO2008033431, WO2008033447, WO2008033356, WO2008033460, WO2008033464, WO2008033465, WO2008033468, WO2008073461.

In one embodiment, the further active ingredient is a modulator of a calcium channel, for example those as described in WO2008073934, WO2008073936, WO2009107660.

In one embodiment, the further active ingredient is an inhibitor of the calcium metabolism, for example those as described in US2009124680.

In one embodiment, the further active ingredient is a blocker of the "T-type calcium channel", as described, for example, in WO2008033431, WO2008110008, US2008280900, WO2008141446, US2009270338, WO2009146540.

In one embodiment, the further active ingredient is an inhibitor of KCNQ potassium channel 2 or 3, for example those as described in US2008027049, US2008027090.

In one embodiment, the further active ingredient is a modulator of KCNN potassium channel 1, 2 or 3 (modulators of the SK1, SK2 and/or SK3 channel), for example those as described in US2009036475.

In one embodiment, the further active ingredient is an inhibitor of the potassium Kv1.3 ion channel, for example those as described in WO2008040057, WO2008040058, WO2008046065, WO2009043117.

In one embodiment, the further active ingredient is a potassium channel modulater, for example those as described in WO2008135447, WO2008135448, WO2008135591, WO2009099820.

In a further embodiment, the further active ingredient is a hyperpolarization-activated cyclic nucleotide-gated (HCN) potassium-sodium channel inhibitor, for example those as described in US2009069296.

In another embodiment, the further active ingredient is an inhibitor of the sodium-potassium-2 chloride (NKCCl) cotransporter, for example those as described in WO2009130735.

In another embodiment, the further active ingredient is a voltage-gated sodium channel inhibitor, for example those as described in WO2009049180, WO2009049181.

In another embodiment, the further active ingredient is a modulator of the MCP-1 receptor (monocyte chemoattractant protein-1 (MCP-1)), for example those as described in WO2008014360, WO2008014381.

In one embodiment, the further active ingredient is a modulator of somatostatin receptor 3 (SSTR3), for example those as described in WO2009011836.

In one embodiment, the further active ingredient is a modulator of somatostatin receptor 5 (SSTR5), for example those as described in WO2008019967, US2008064697, US2008249101, WO2008000692, US2008293756, WO2008148710.

In one embodiment, the further active ingredient is a modulator of somatostatin receptor 2 (SSTR2), for example those as described in WO2008051272.

In one embodiment, the further active ingredient is a compound which is capable of reducing the amount of retinol-binding protein 4 (RBP4), for example those as described in WO2009051244.

In one embodiment, the further active ingredient is an erythropoietin-mimetic peptide which acts as an erythropoietin (EPO) receptor agonist. Such molecules are described, for example, in WO2008042800.

In a further embodiment, the further active ingredient is an anorectic/a hypoglycemic compound, for example those as described in WO2008035305, WO2008035306, WO2008035686.

In one embodiment, the further active ingredient is an inductor of lipoic acid synthetase, for example those as described in WO2008036966, WO2008036967.

In one embodiment, the further active ingredient is a stimulator of endothelial nitric oxide synthase (eNOS), for example those as described in WO2008058641, WO2008074413.

In one embodiment, the further active ingredient is a modulator of carbohydrate and/or lipid metabolism, for example those as described in WO2008059023, WO2008059024, WO2008059025, WO2008059026.

In a further embodiment, the further active ingredient is an angiotensin II receptor antagonist, for example those as described in WO2008062905, WO2008067378, WO2008062905.

In one embodiment, the further active ingredient is an agonist of the sphingosine-1-phosphate receptor (S1P), for example those as described in WO2008064315, WO2008074820, WO2008074821, WO2008135522, WO2009019167, WO2009043013, WO2009080663, WO2009085847

In one embodiment, the further active ingredient is an agent which retards gastric emptying, for example 4-hydroxyisoleucine (WO2008044770).

In one embodiment, the further active ingredient is a trytophan-5-hydroxylase inhibitor-1 (TPH1 inhibitor), which modulates gastrointestinal motility, as described, for example, in WO2009014972.

In one embodiment, the further active ingredient is a muscle-relaxing substance, as described, for example, in WO2008090200.

In a further embodiment, the further active ingredient is an inhibitor of monoamine oxidase B (MAO-B), for example those as described in WO2008092091, WO2009066152.

In a further embodiment, the further active ingredient is an inhibitor of monoamine oxidase A (MAO-A), for example those as described in WO2009030968.

In another embodiment, the further active ingredient is an inhibitor of the binding of cholesterol and/or triglycerides to the SCP-2 protein (sterol carrier protein-2), for example those as described in US2008194658.

In a further embodiment, the further active ingredient is a compound which binds to the β-subunit of the trimeric GTP-binding protein, for example those as described in WO2008126920.

In one embodiment, the further active ingredient is a urate anion exchanger inhibitor 1, as described, for example, in WO2009070740.

In one embodiment, the further active ingredient is a modulator of the ATP transporter, as described, for example, in WO2009108657.

In another embodiment, the further active ingredient is lisofylline, which prevents autoimmune damage to insulin-producing cells.

In yet another embodiment, the further active ingredient is an extract from *Bidens pilosa* with the ingredient cytopiloyne as described in EP1955701.

In one embodiment, the further active ingredient is an inhibitor of glucosylceramide synthase, as described, for example, in WO2008150486.

In a further embodiment of the invention, the further active ingredient is a glycosidase inhibitor, as described, for example, in WO2009117829.

In another embodiment, the further active ingredient is an ingredient from the plant *Hoodia Gordonii*, as described in US2009042813, EP2044852.

In one embodiment, the further active ingredient is an antidiabetic, for example D-tagatose.

In one embodiment, the further active ingredient is a zinc complex of curcumin, as described in WO2009079902.

In one embodiment, the further active ingredient is an inhibitor of the "cAMP response element binding protein" (CREB), as described in WO2009143391.

In another embodiment, the further active ingredient is an antagonist of the bradykinin B1 receptor, as described in WO2009124746.

In a further embodiment, the further active ingredient is a compound which is capable of modulating diabetic peripheral neuropathy (DPN). Such modulators are, for example, FK-1706 or SB-509, or those as described in WO1989005304, WO2009092129.

In one embodiment, the further active ingredient is a compound which is capable of modulating diabetic nephropathy. Such compounds are described, for example, in WO2009089545.

In one embodiment, the further active ingredient is an inhibitor (e.g. an anti-0038 antibody) of 0038, as described in US2009196825.

In one embodiment, the further active ingredient is an inhibitor of human fibroblast growth factor receptor 4 (FGFR4), as described, for example, in WO2009046141.

In a further embodiment of the invention, the further active ingredient is a compound which protects the beta cell, for example 14-alpha-lipolyl-andrographolide (AL-1).

In yet another embodiment of the invention, the further active ingredient is the INGAP (islet neogenesis associated protein) peptide, a peptide which reestablishes insulin production in patients with diabetes mellitus.

In one embodiment of the invention, the further active ingredient is a modulator of the CFTR (cystic fibrosis transmembrane conductance regulator), as described, for example, in US2009246137, US2009264433, US2009264441, US2009264471, US2009264481, US2009264486.

In one embodiment of the invention, the further active ingredient is a compound which stimulates/modulates insulin release, for example those as described in WO2009109258, WO2009132739, US2009281057.

In one embodiment of the invention, the further active ingredient is an extract from *Hippophae rhamnoides*, as described, for example, in WO2009125071.

In one embodiment of the invention, the further active ingredient is an extract from *Huanglian* and *Ku Ding Cha*, as described, for example, in WO2009133458.

In one embodiment, the compound of the formula I is administered in combination with bulking agents, preferably insoluble bulking agents (see, for example, Carob/Caromax®

(Zunft H J; et al., Carob pulp preparation for treatment of hypercholesterolemia, ADVANCES IN THERAPY (2001 September-October), 18(5), 230-6). Caromax is a carob-containing product from Nutrinova, Nutrition Specialties & Food Ingredients GmbH, lndustriepark Höchst, 65926 Frankfurt/ Main)). Combination with Caromax® is possible in one preparation or by separate administration of compounds of the formula I and Caromax®. Caromax® can in this connection also be administered in the form of food products such as, for example, in bakery products or muesli bars.

It will be appreciated that every suitable combination of the compounds of the invention with one or more of the aforementioned compounds and optionally one or more other pharmacologically active substances is considered to be covered within the scope of protection conferred by the present invention.

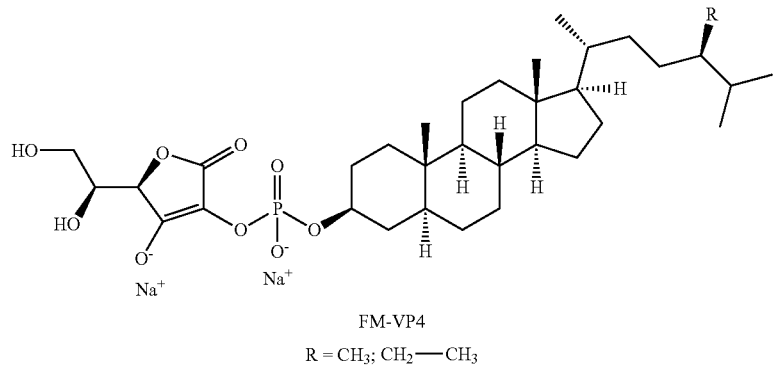

FM-VP4
R = CH₃; CH₂—CH₃

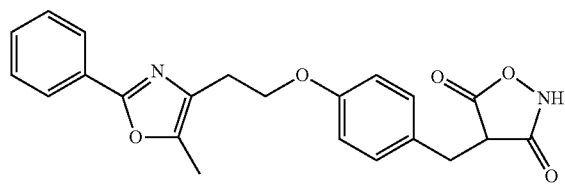

JTT-501

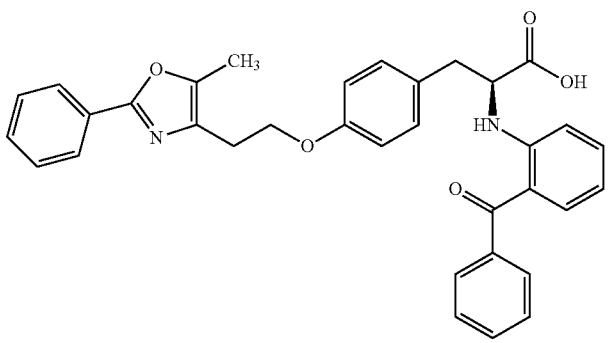

GI 262570

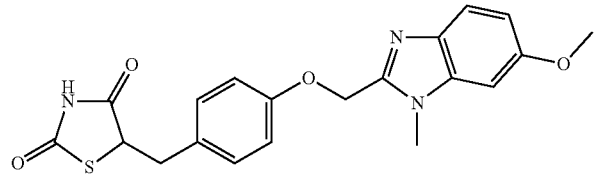

CS-011
rivoglitazone

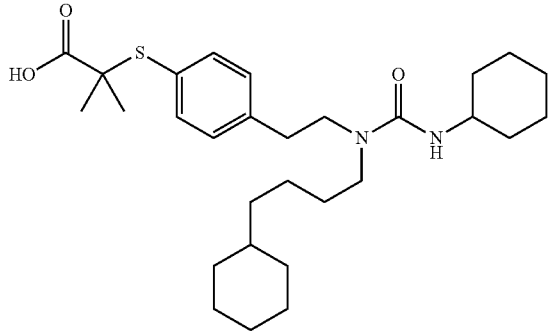

GW-9578

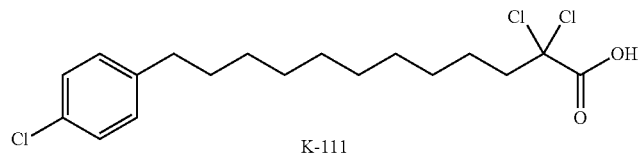

K-111

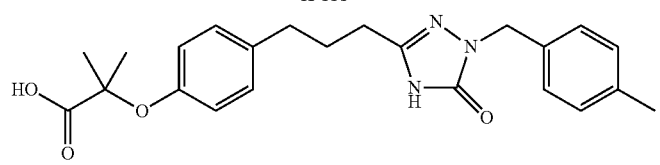

LY-518674

-continued
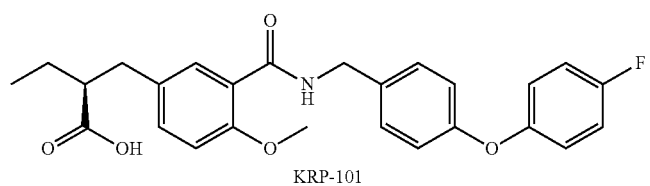
KRP-101
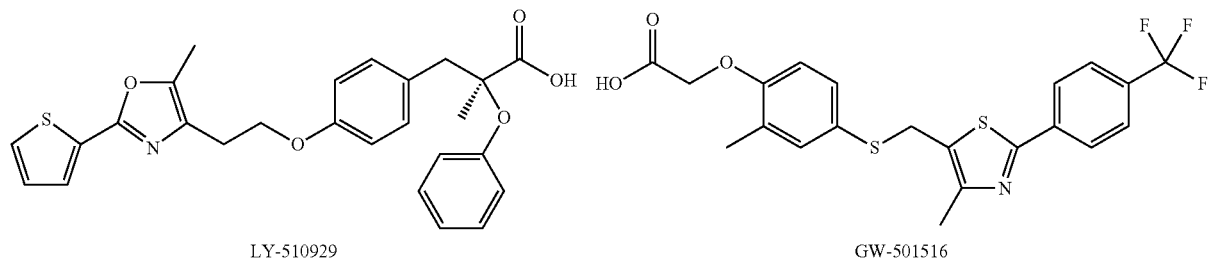
LY-510929
GW-501516
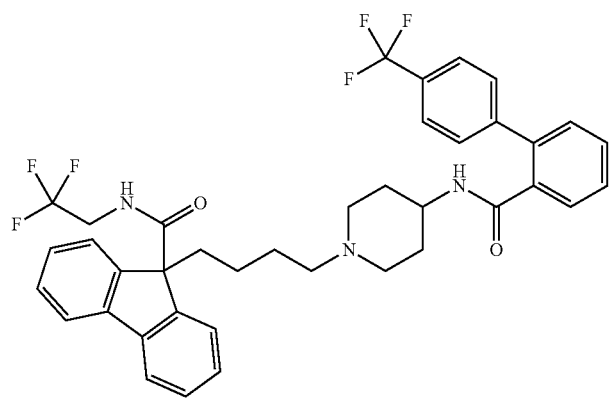
BMS-201038
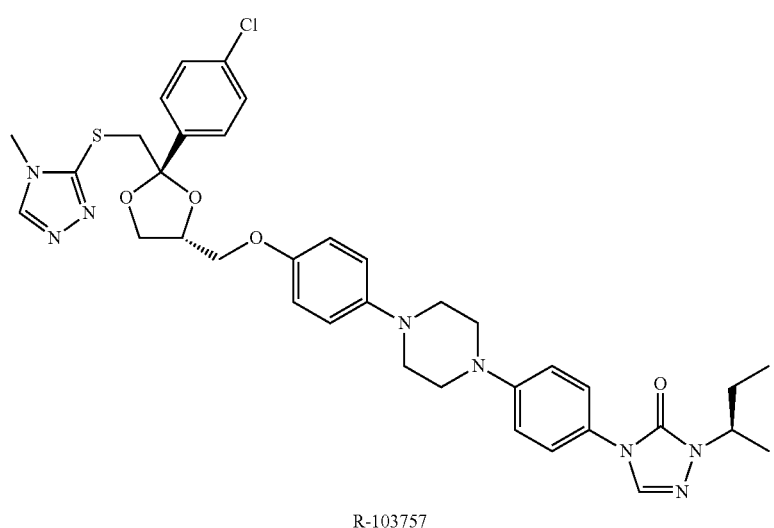
R-103757

-continued
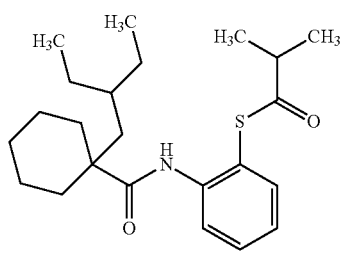
JTT-705
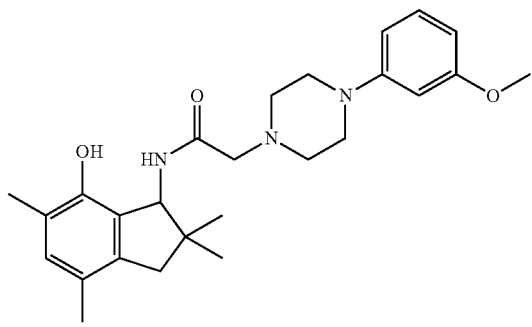
OPC-14117
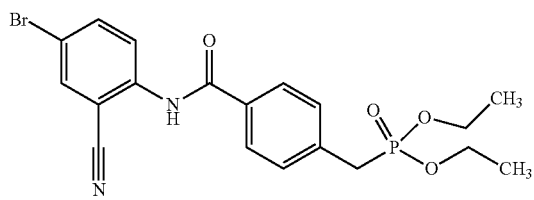
NO-1886
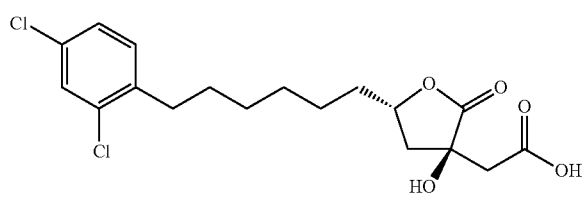
SB-204990
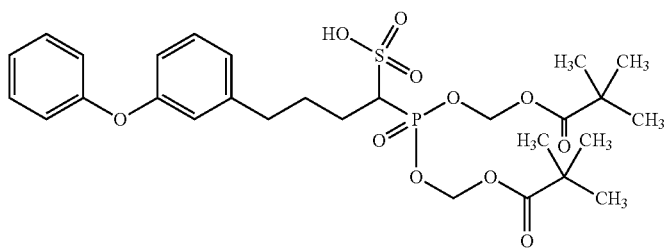
BMS-188494
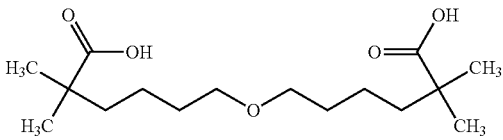
CI-1027
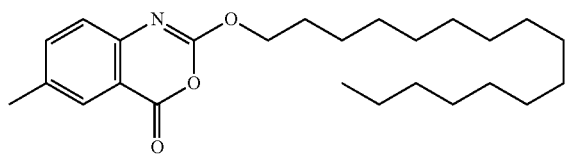
ATL-962
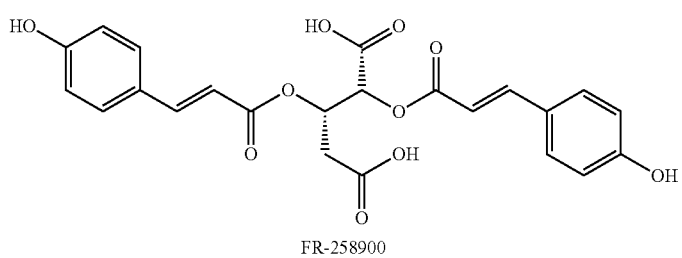
FR-258900

-continued
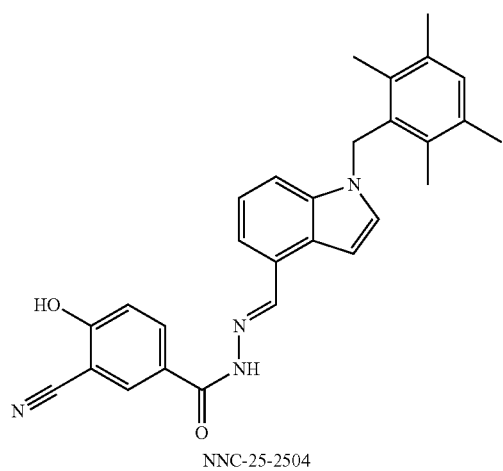
NNC-25-2504
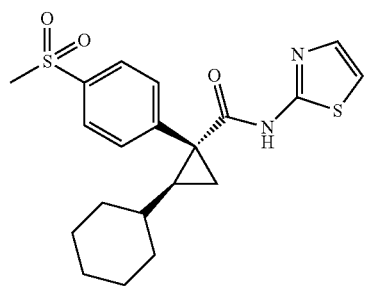
LY-2121260
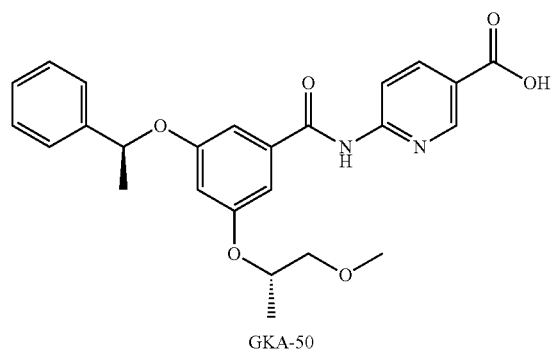
GKA-50
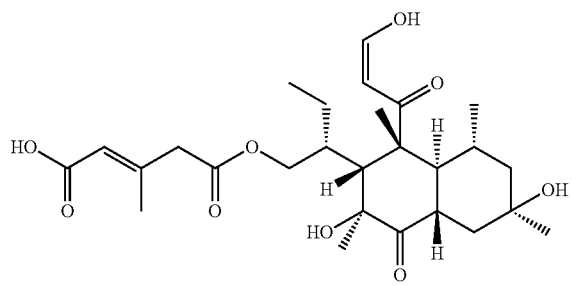
FR-225654
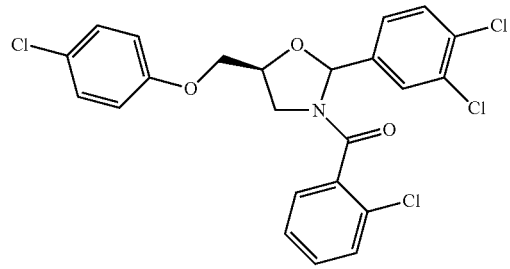
KST-48
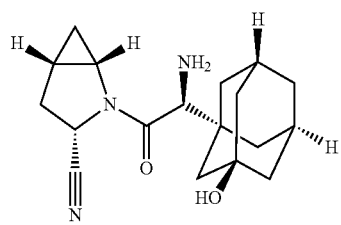
BMS-477118
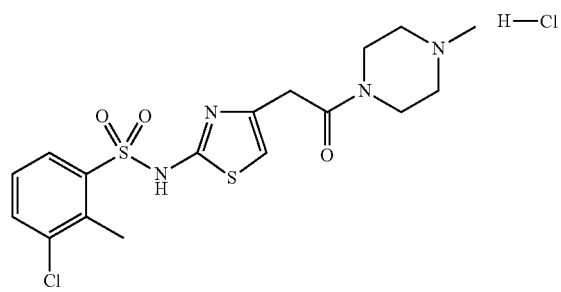
BVT-2733
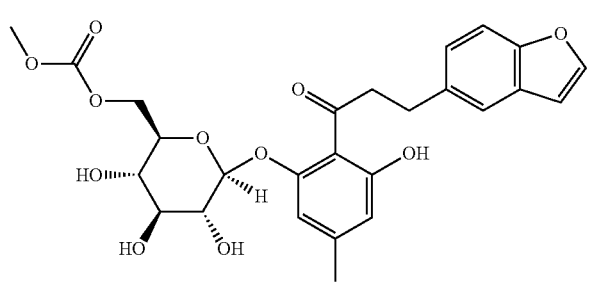
T-1095

-continued
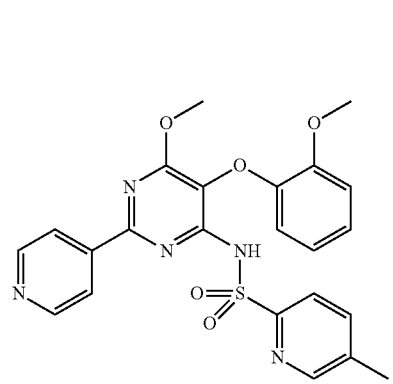
SPP-301
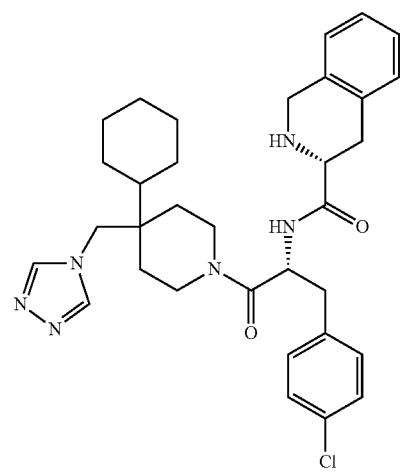
THIQ
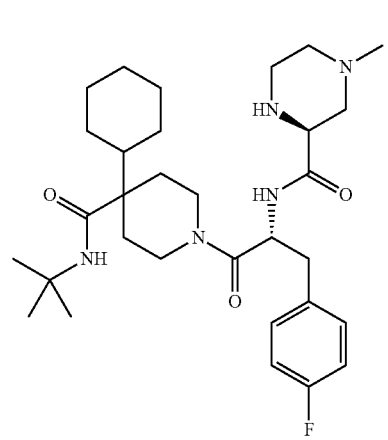
MB243
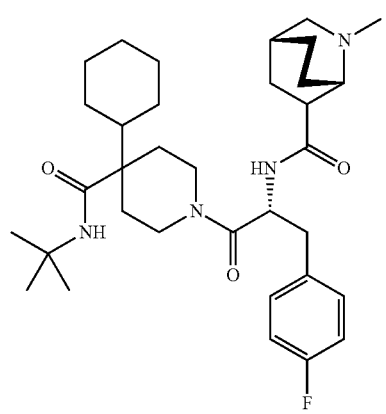
RY764
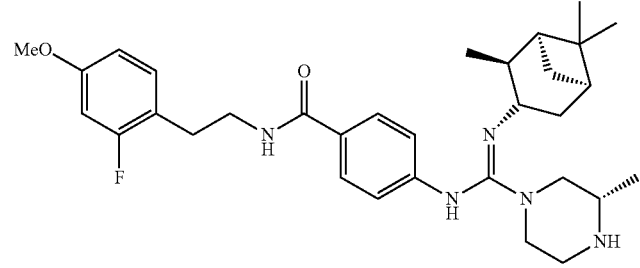
CHIR-785
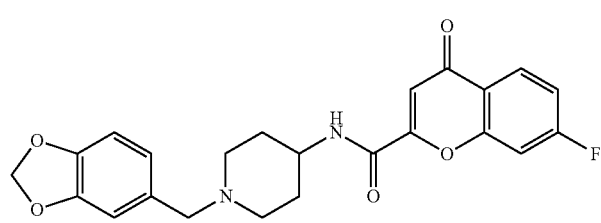
A-761
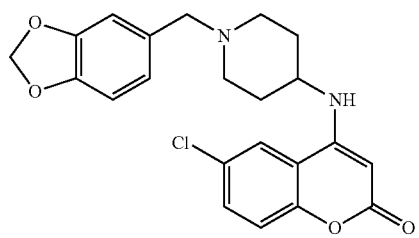
A-665798
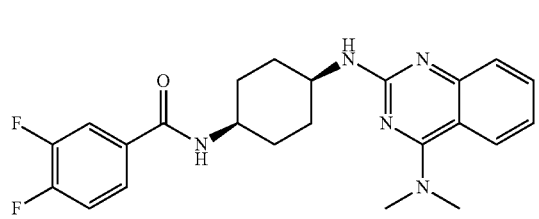
ATC-0175
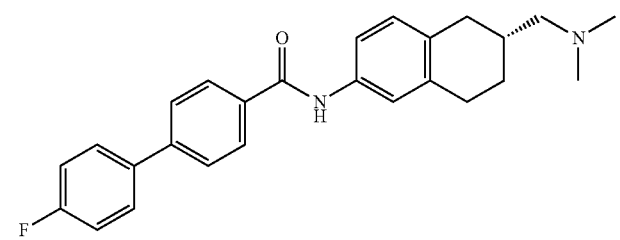
T-226296
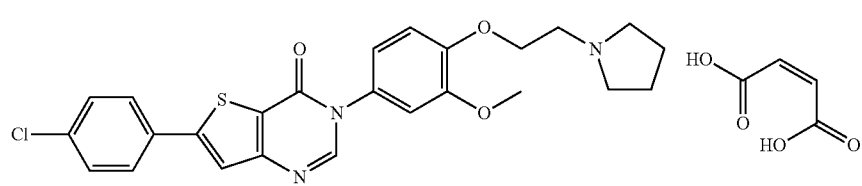
GW-803430

-continued
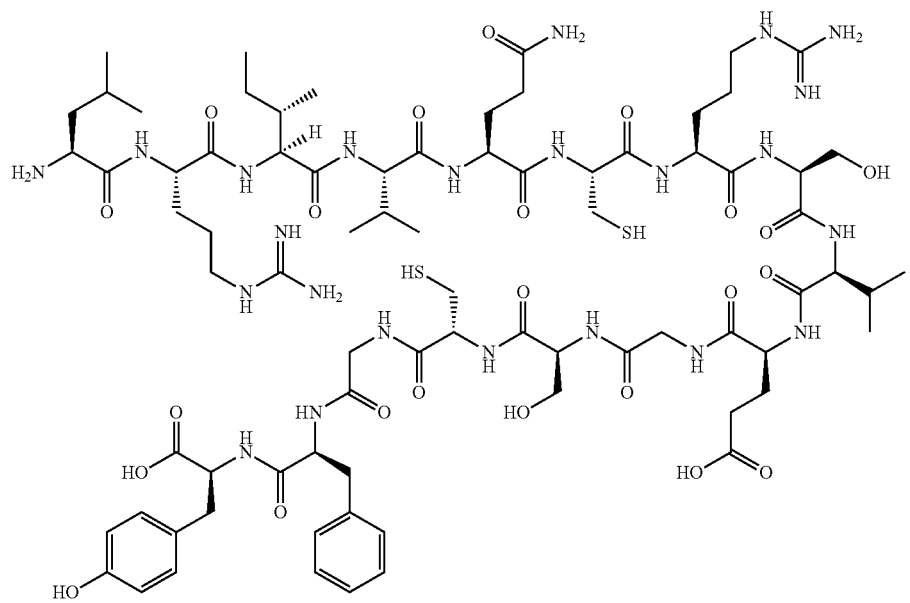
AOD-9604
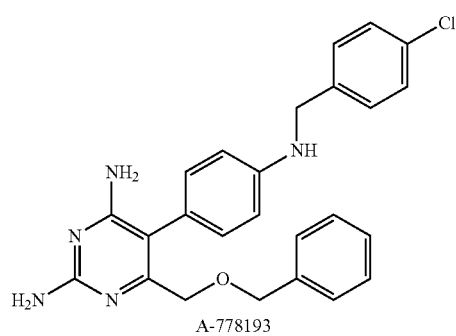
A-778193
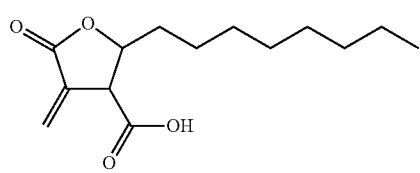
C75
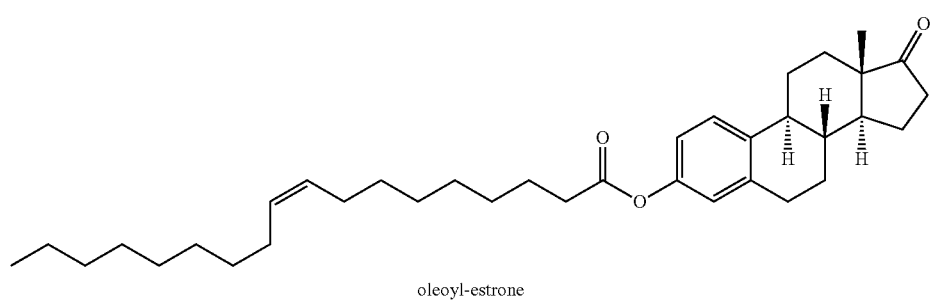
oleoyl-estrone
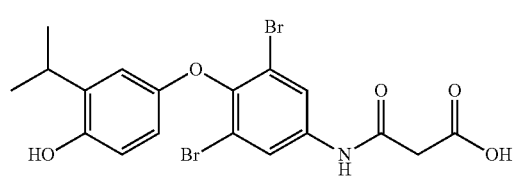
KB-2115
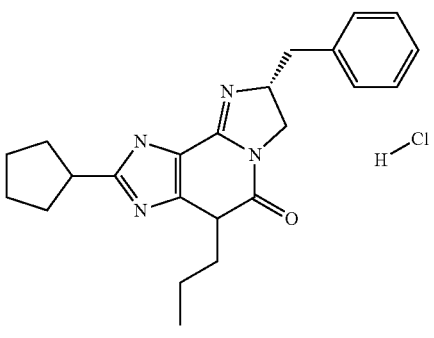
KCP-265

-continued
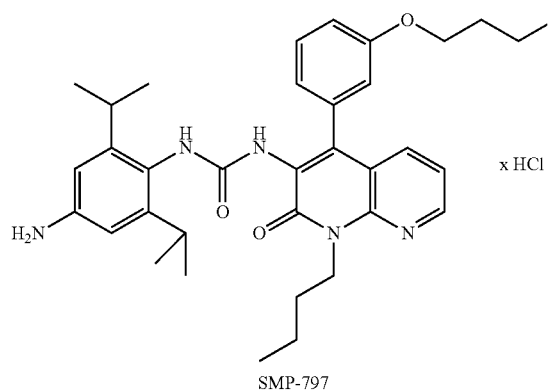
SMP-797 x HCl
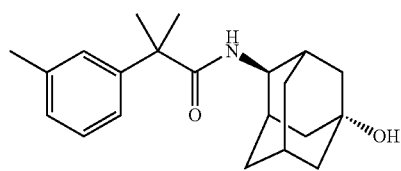
JNJ-25918646
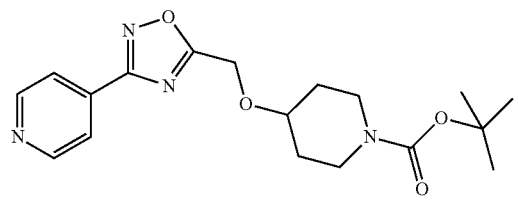
PSN-632408
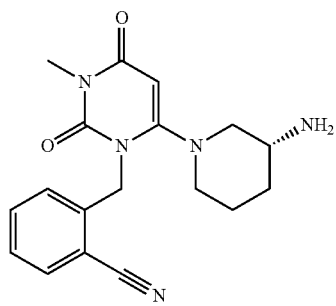
SYR-322
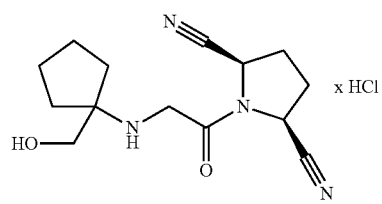
DP-893 x HCl
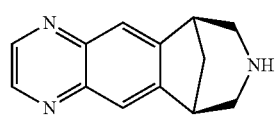
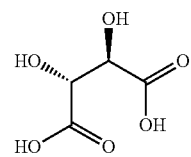
varenicline tartrate
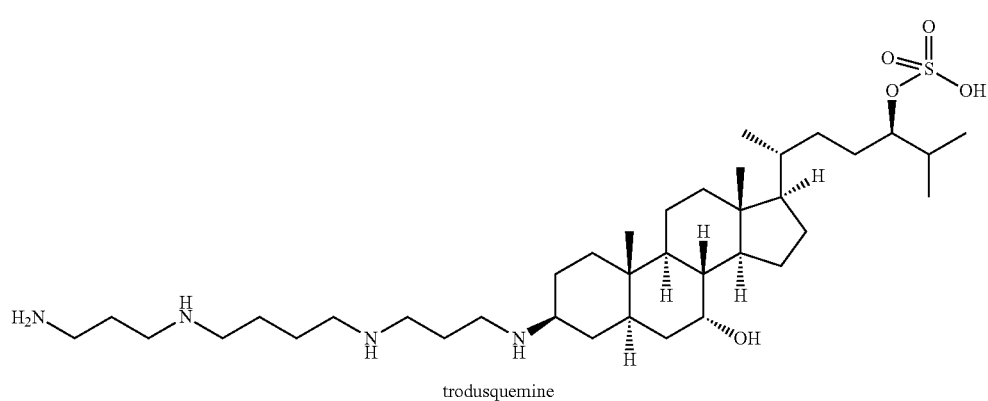
trodusquemine
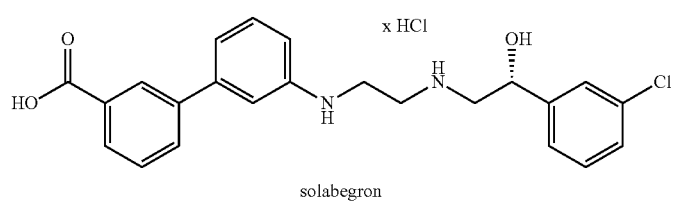
solabegron
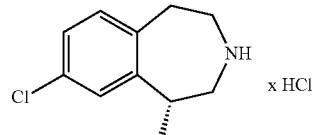
loraserine hydrochloride -continued
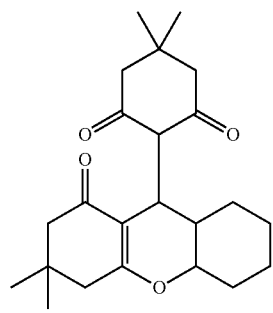
L-152804
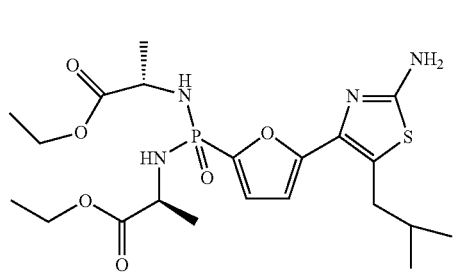
MB-06322
CS-917
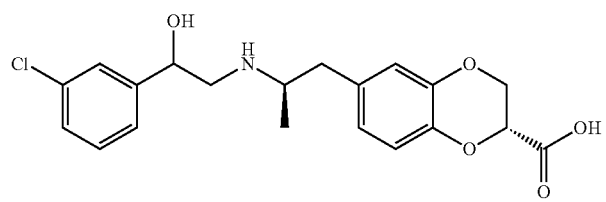
N-5984
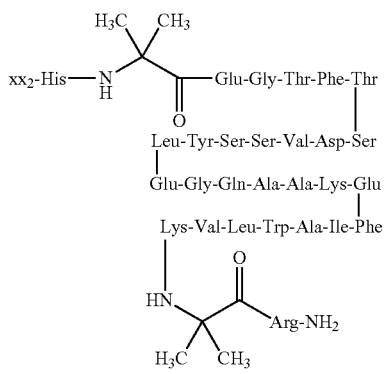
BIM-51077
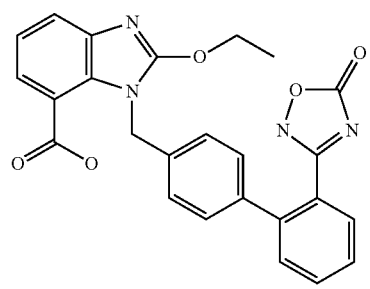
TAK-536
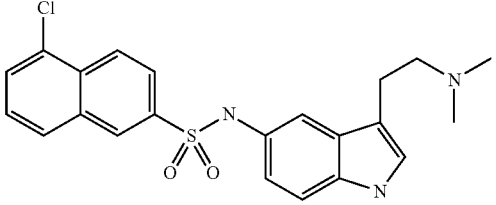
E-6837
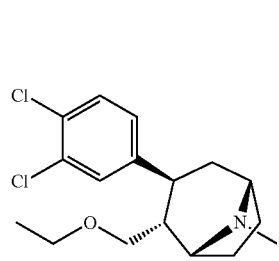
tesofensine
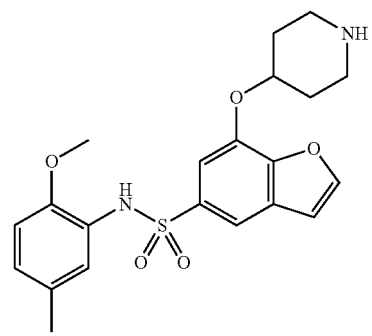
BVT-74316
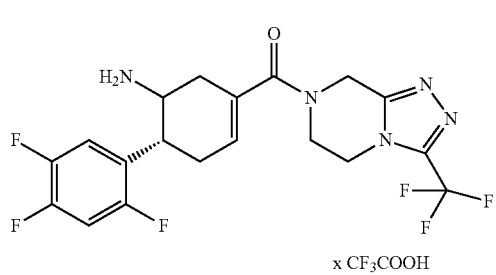
ABT-341

-continued
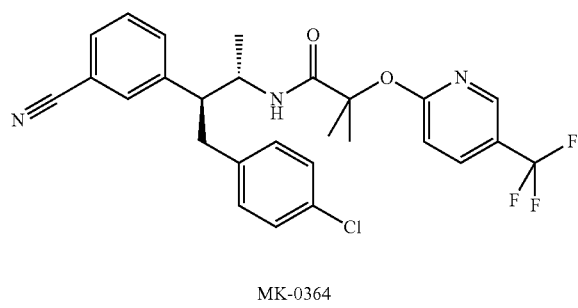
MK-0364
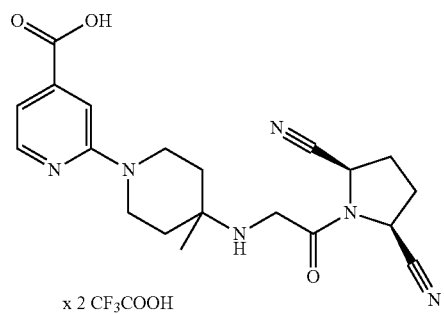
x 2 CF₃COOH
ABT-279
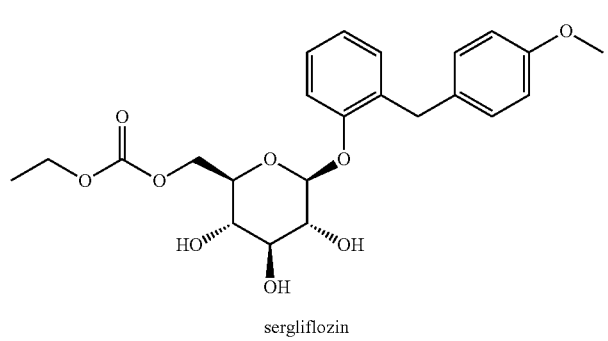
sergliflozin
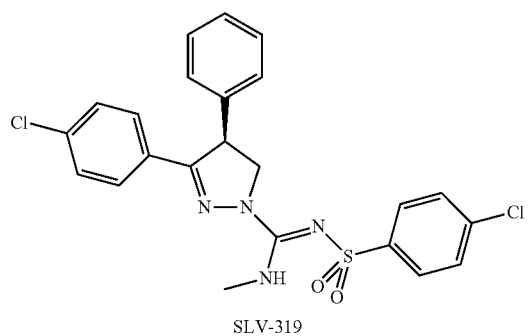
SLV-319
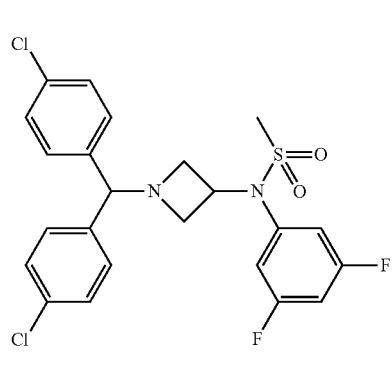
AVE 1625
(proposed INN: drinabant)
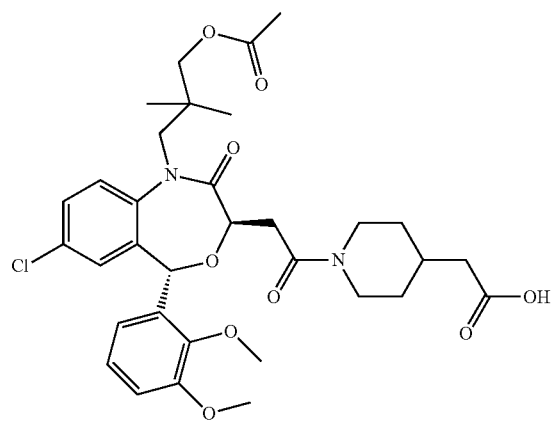
TAK-475
(lapaquistat acetate)
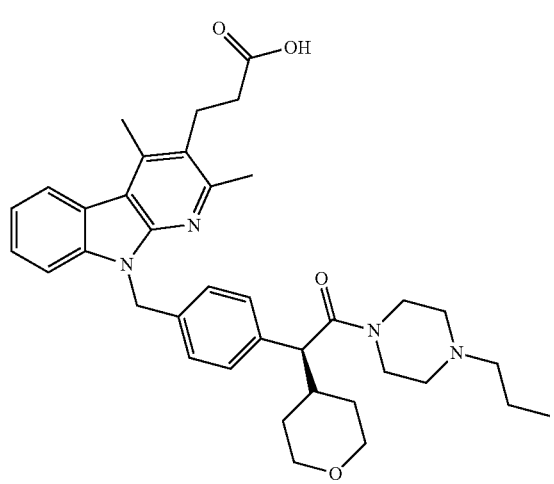
AS-1552133
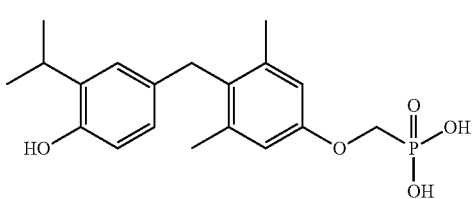
MB-07344

-continued
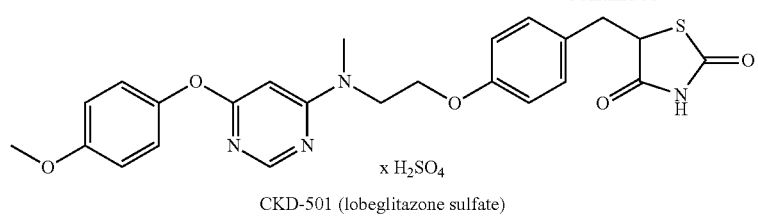
CKD-501 (lobeglitazone sulfate)
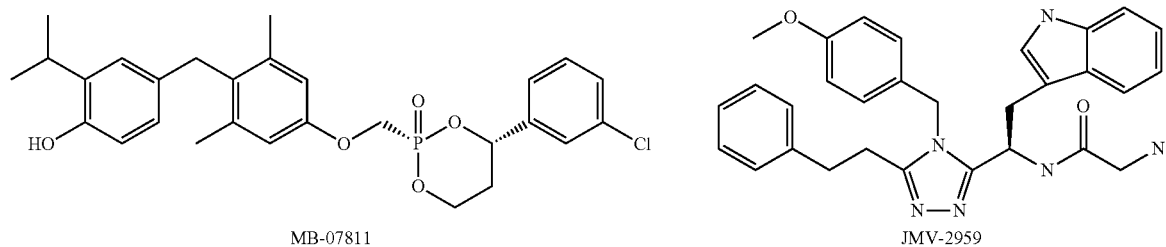
MB-07811
JMV-2959
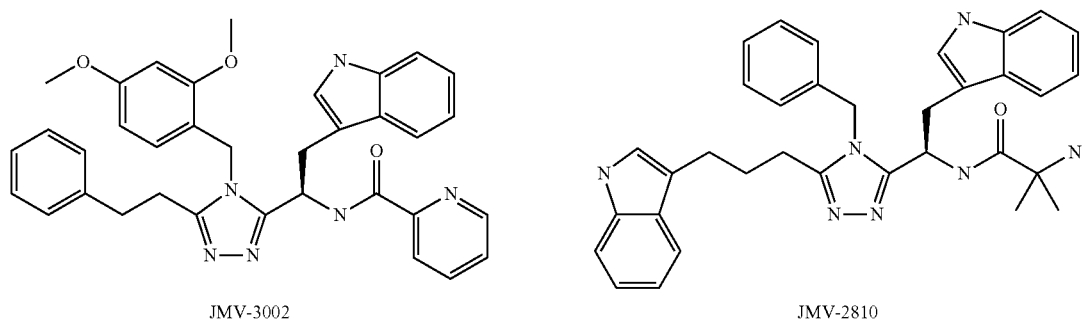
JMV-3002
JMV-2810
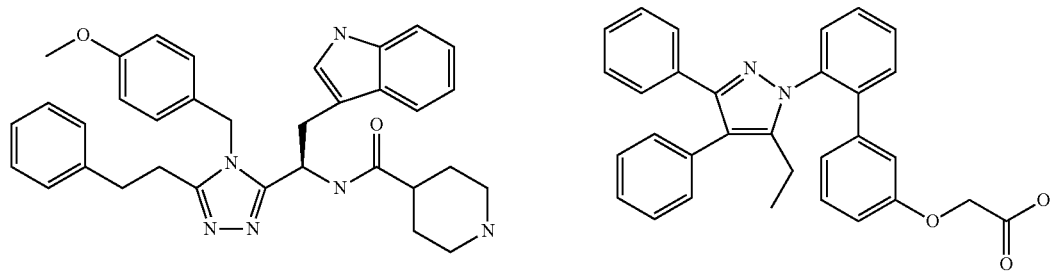
JMV-2951
BMS-309403
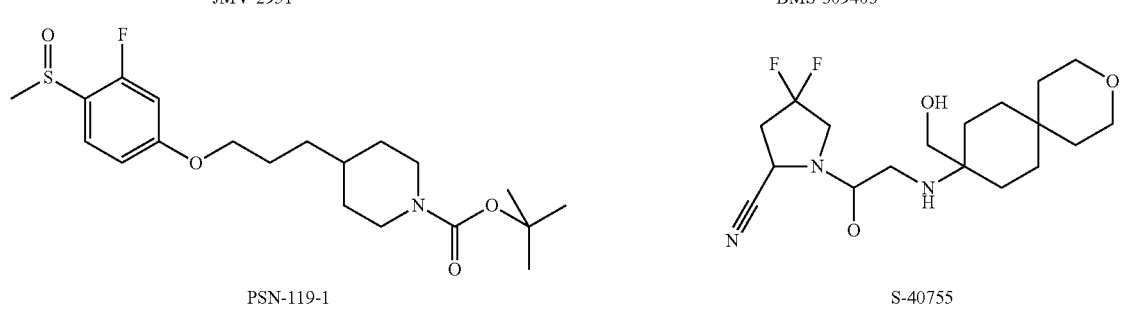
PSN-119-1
S-40755

-continued
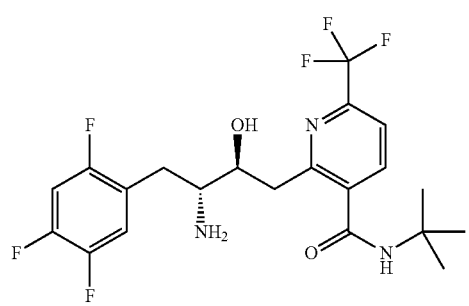
LY-2463665
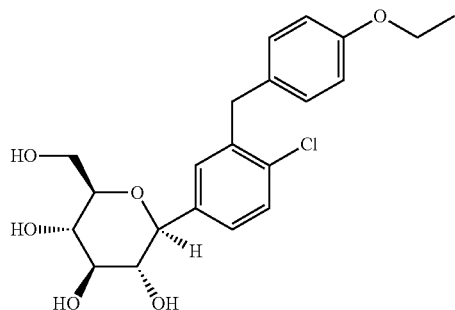
dapagliflozin, BMS-512148
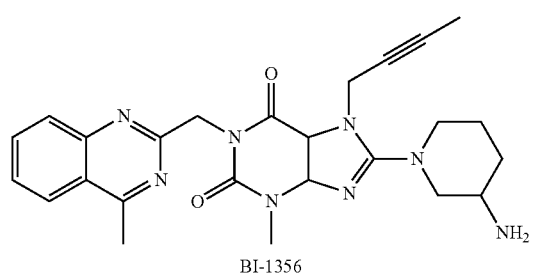
BI-1356
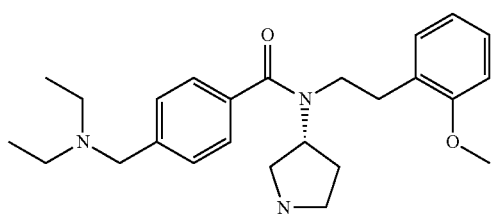
PF-429242
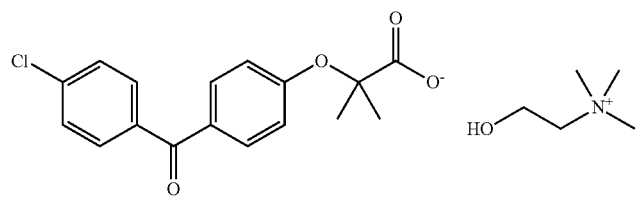
SLV-348
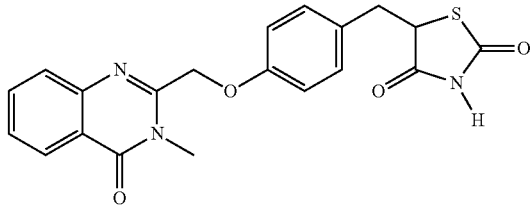
balaglitazone
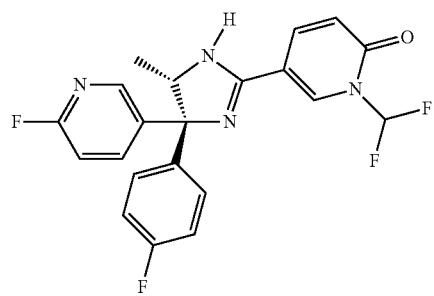
"NPY-5-BY"
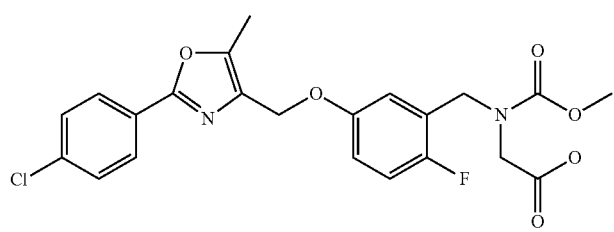
BMS-711939
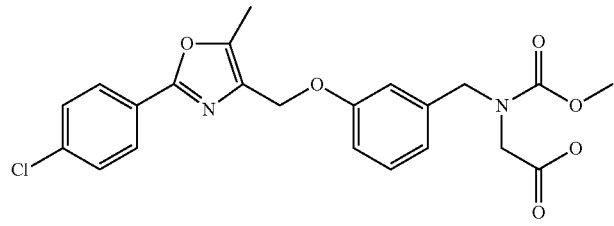
BMS-687453
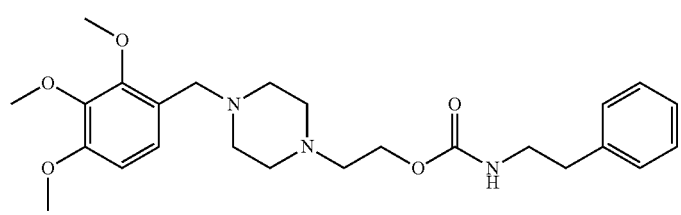
ST-3473
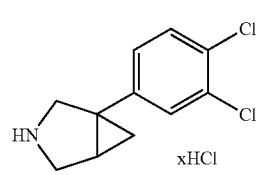
DOV-21947

-continued
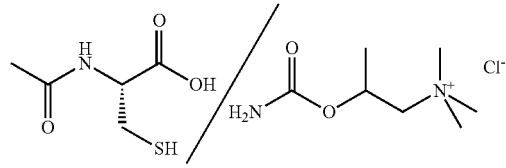
DM-71
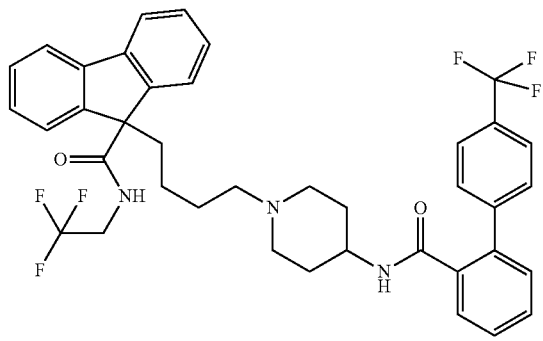
AEGR-733
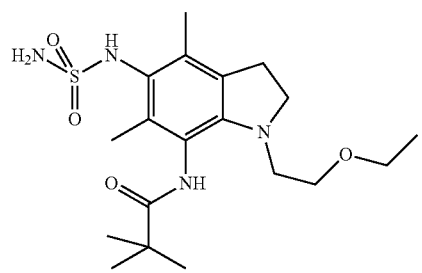
KY-382
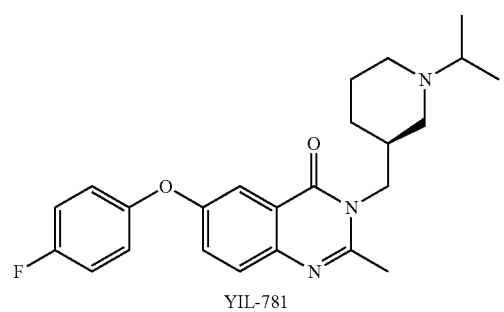
YIL-781
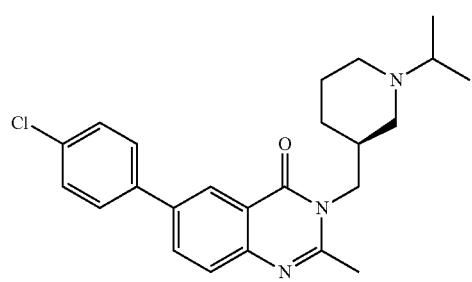
YIL-870
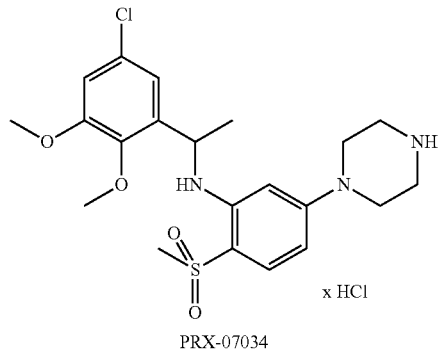
PRX-07034
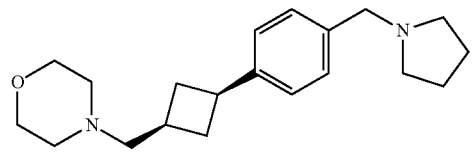
PF-00389027
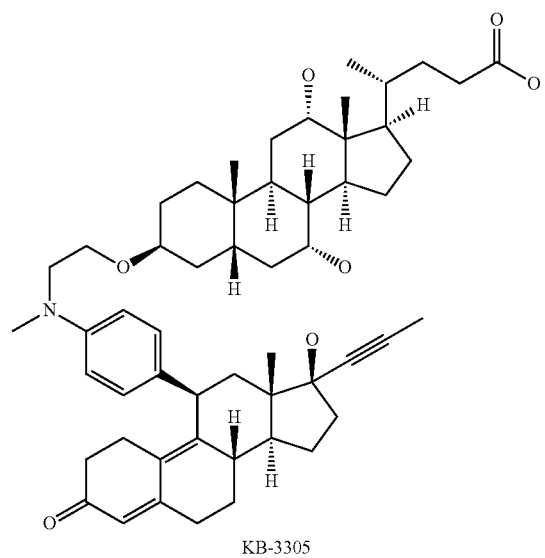
KB-3305

69
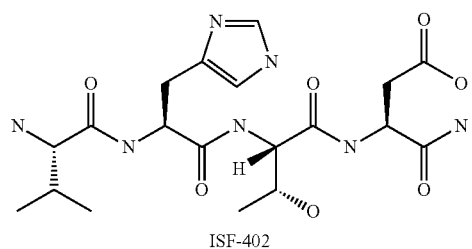
ISF-402
70
-continued
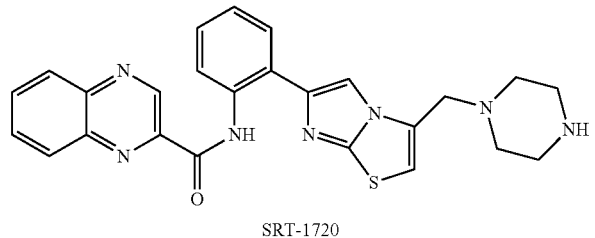
SRT-1720
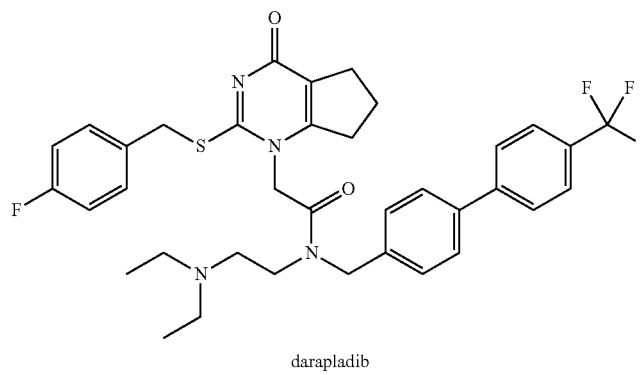
darapladib
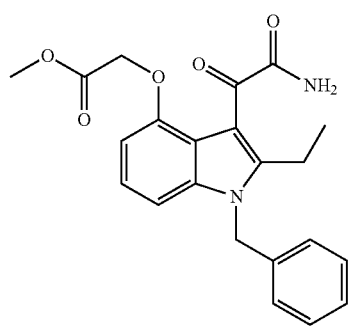
A-002
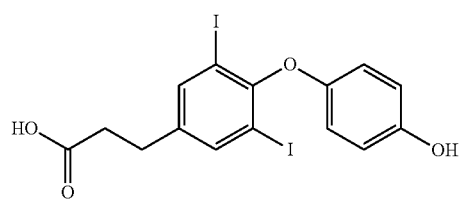
DITPA
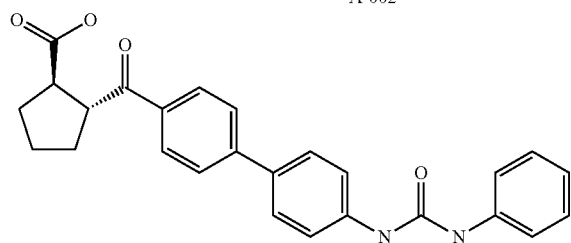
DGAT-1 inhibitor from
WO2007137103
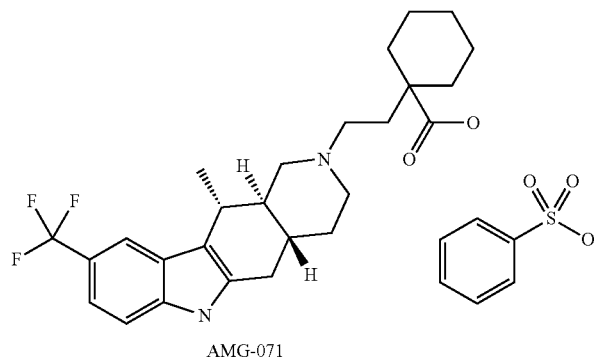
AMG-071
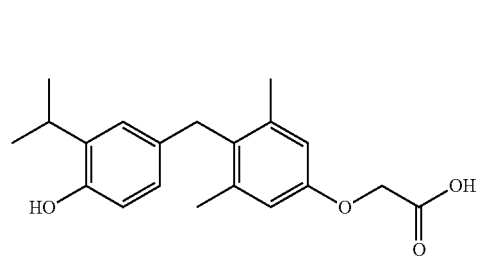
sobetirome
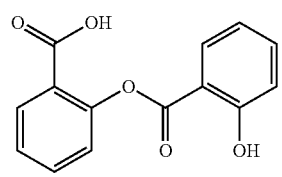
salsalate
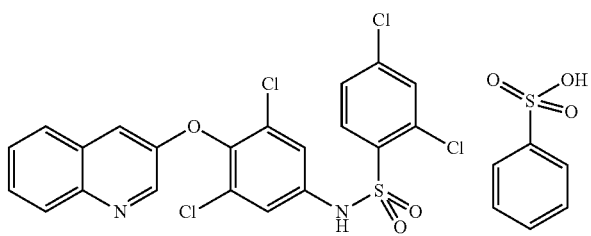
INT-131

-continued
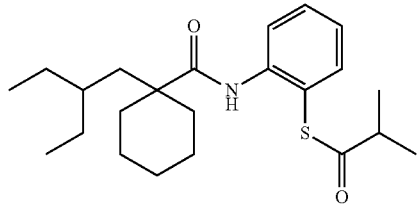
dalcetrapib
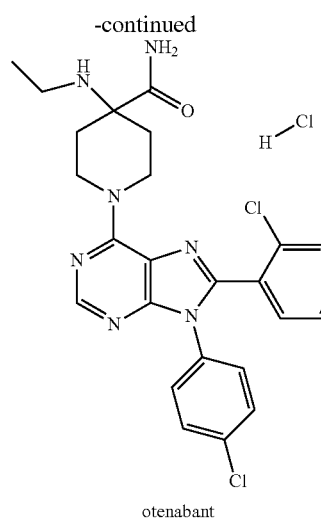
otenabant
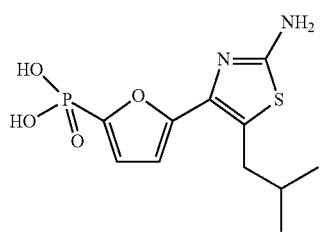
MB-07229
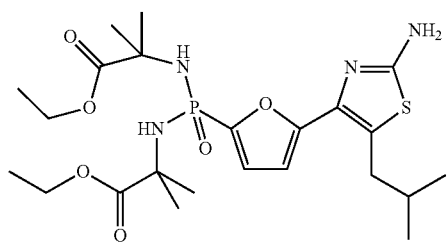
MB-07803
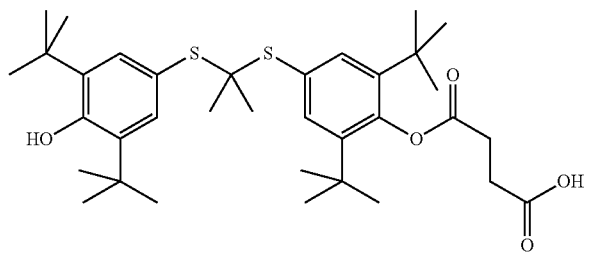
succinobucol
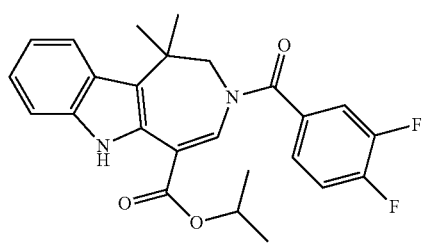
WAY-362450
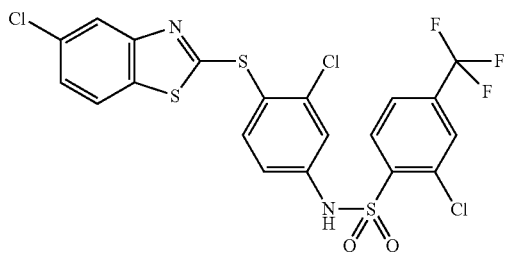
T-2384
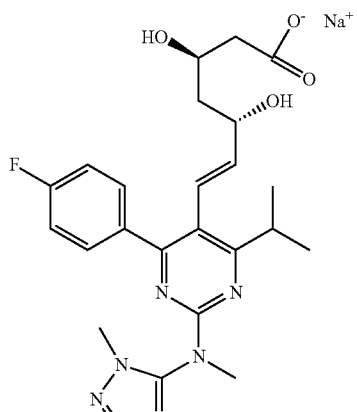
BMS-644950
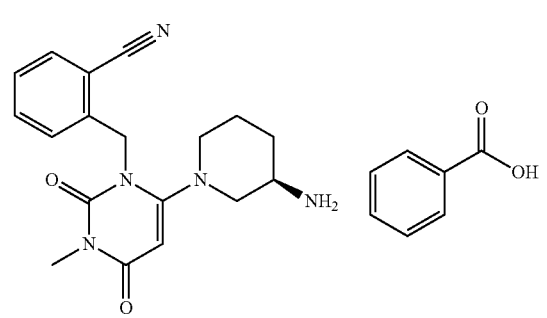
alogliptin benzoate

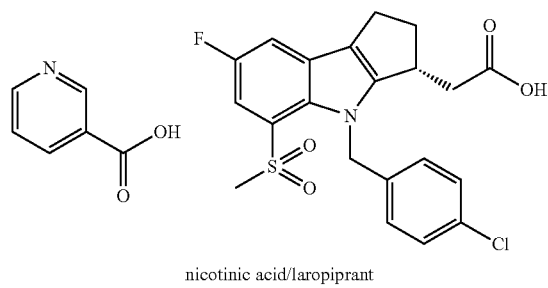
nicotinic acid/laropiprant
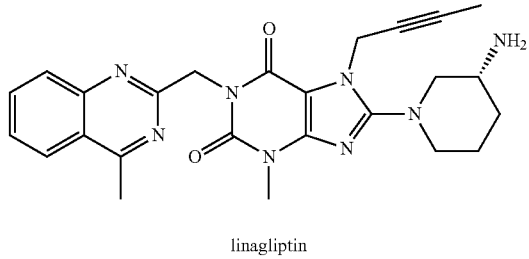
linagliptin
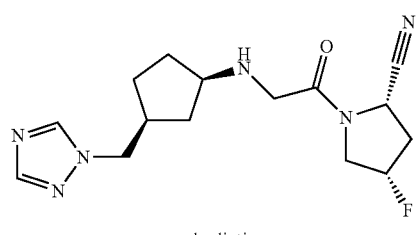
melogliptin
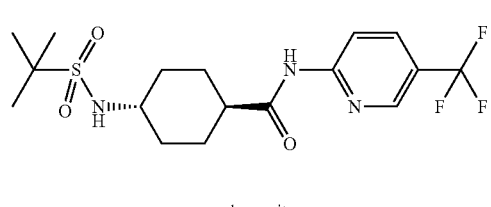
velneperit
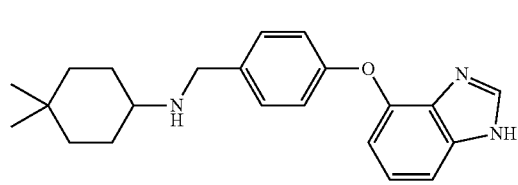
GSK-982
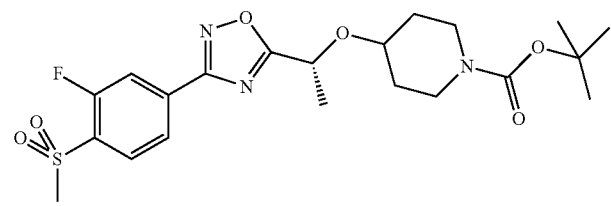
PSN-119-2
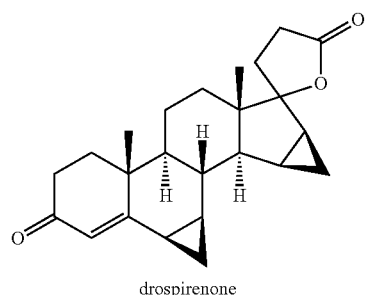
drospirenone
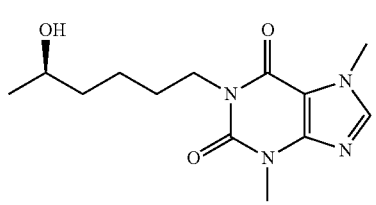
lisofylline
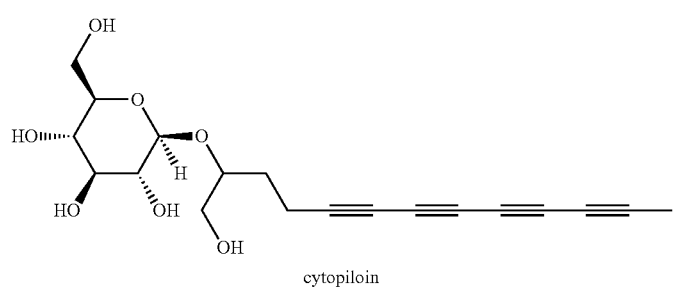
cytopiloin
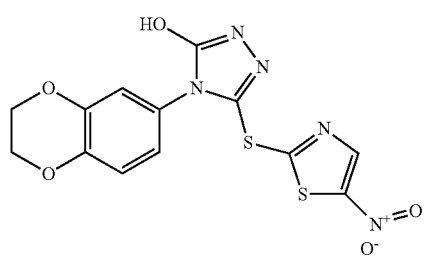
BI-78D3

-continued
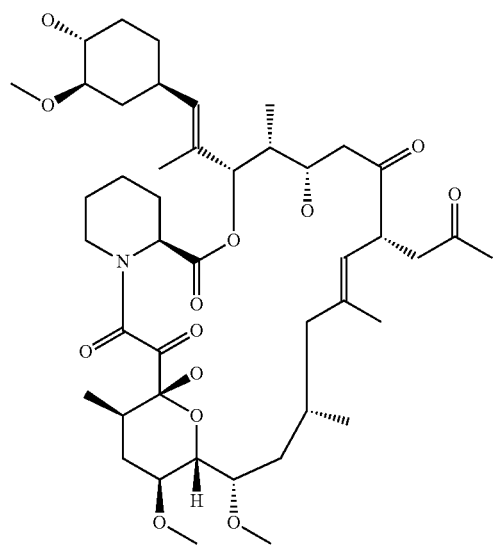
FK-1709
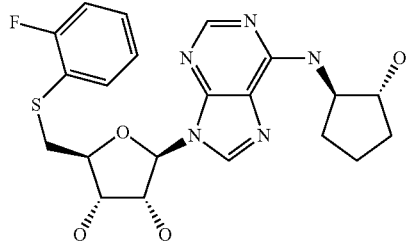
CVT-3619
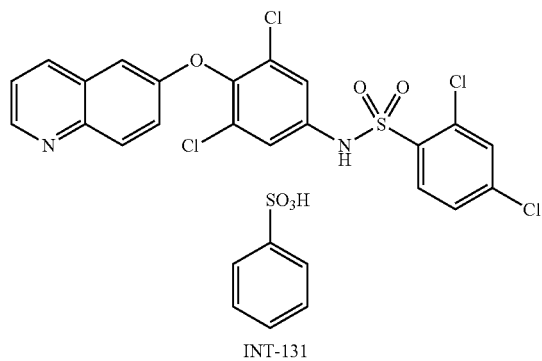
INT-131
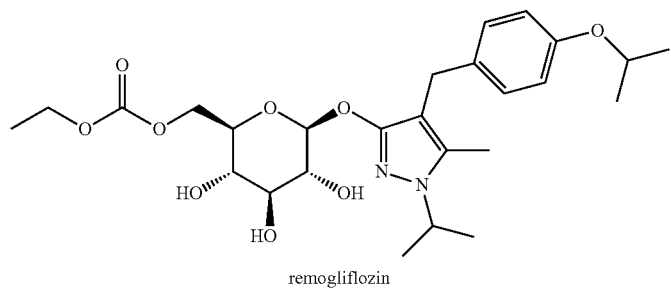
remogliflozin
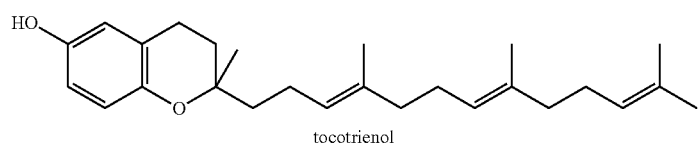
tocotrienol
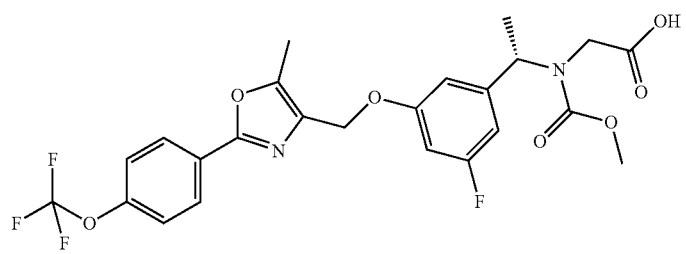
BMS-759509

-continued

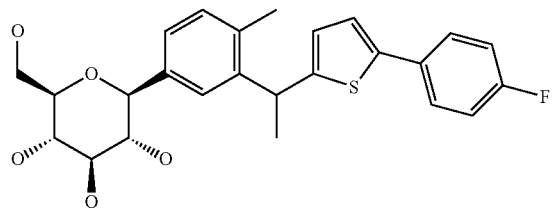

canagliflozin

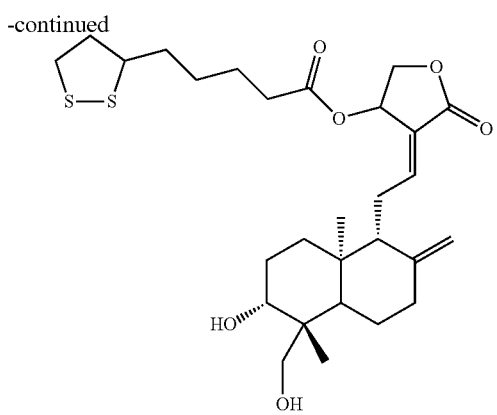

14-alpha-lipolyl-andrographolide (AL-1)

fatostatin

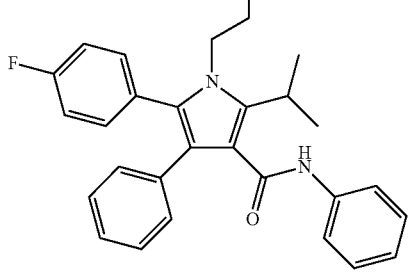

NCX-6560

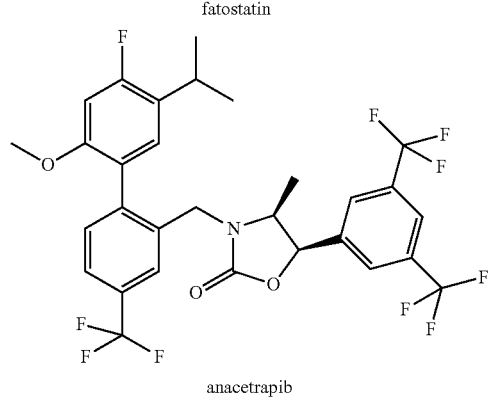

anacetrapib

Also suitable are the following active ingredients for combination preparations:
all antiepileptics specified in the Rote Liste 2007, chapter 15;
all antihypertensives specified in the Rote Liste 2007, chapter 17;
all hypotonics specified in the Rote Liste 2007, chapter 19;
all anticoagulants specified in the Rote Liste 2007, chapter 20;
all arteriosclerosis drugs specified in the Rote Liste 2007, chapter 25;
all beta receptors, calcium channel blockers and inhibitors of the renin angiotensin
system specified in the Rote Liste 2007, chapter 27;
all diuretics and perfusion-promoting drugs specified in the Rote Liste 2007, chapter 36 and 37;
all withdrawal drugs/drugs for the treatment of addictive disorders specified in the Rote Liste 2007, chapter 39;
all coronary drugs and gastrointestinal drugs specified in the Rote LiSte 2007, chapter 55 and 60;
all migraine drugs, neuropathy preparations and Parkinson's drugs specified in the Rote Liste 2007, chapter 61, 66 and 70.

Test Models

Suitability of the compounds of the invention as active pharmaceutical ingredients can be tested by means of various test models. Descriptions are given of such test models by way of example below.

Influence on the MCH Receptor in vitro; Determination of Functional IC50 Values of MCH1R Antagonists Cloning of the cDNA for the human MCH receptor, preparation of a recombinant HEK293 cell line which expresses the human MCH receptor, and functional measurements with the recombinant cell line took place in analogy to the description by Audinot et al. (J. Biol. Chem. 2001, 276, 13554-13562). A difference from the reference was, however, the use of the plasmid pEAK8 from EDGE Biosystems (USA) for the construction of the expression vector. The host used for the transfection was a transformed HEK cell line named "PEAK Stable Cells" (likewise from EDGE Biosystems). Functional measurements of the cellular calcium flux after addition of agonist (MCH) in the presence of ligand of the invention took place with the aid of the FLIPR apparatus from Molecular Devices (USA), using protocols of the apparatus manufacturer. The compounds of the invention show a significant inhibition (>30%) of the signal induced by the agonist at a concentration of 100 µM, preferably at 10 µM, particularly preferably at 1 µM, very particularly preferably at 100 nM and very very particularly preferably at 10 nM.

Besides the functional activity it is also possible to determine the affinity for the MCH1R according to Audinot et al. (Br. J. Pharmacol, 2001, 133, 371-378). Preferred compounds of the invention show an IC50 of less than 1 µM, particularly preferably of less than 100 nM, very particularly preferably of less than 10 nM and very very particularly preferably of less than 1 nM.

Milk Intake by Female NMRI Mice

The anorectic effect is tested on female NMRI mice. After withdrawal of feed for 24 hours, the test substance is administered intraperitoneally or preferably orally by gavage. The animals are housed singly with free access to drinking water and, 30 minutes after administration of product, are offered condensed milk. The condensed milk consumption is determined every half hour for 7 hours, and the general condition of the animals is observed. The measured milk consumption is compared with the vehicle-treated control animals.

The vehicle itself has no influence on feed intake. Preferred tolerated vehicles for the administration are, for example, hydroxyethylcellulose (0.5% in water) or Solutol HS15 (5% in hydroxyethylcellulose (0.5% in water)).

Feed and Water Intake of Female Wistar Rats

As alternative to testing the anorectic effect on NMRI mice, it is also possible analogously to use female Wistar rats weighing about 220-250 g. The animals are accustomed to the experimental environment before the start of the study. In one embodiment, the animals have free access to feed and water up to the start of the experiment. In another embodiment, access of the animals to feed is withdrawn 24 hours before the administration. For the investigation of the test substance, the animals are housed singly with free access to feed and water. Feed intake and water intake are measured continuously every 30 minutes over a period of 22 hours using a computer-assisted system (TSE Drinking & Feeding Monitor). The measured feed and water consumption is compared with the vehicle-treated control animals.

Body Weight Gain of Diet-induced Obese and Standard-fed Mice

For these investigations, male C57BL6J mice 5 weeks old (weaning age) are accustomed either to a standard maintenance diet or to a high-fat and thus high-energy diet. After 12 weeks, the normally fed, slim mice have typically reached a body weight of about 25 g, and the fat-fed mice have reached one of about 35 g. The animals are housed singly, and the feed intake and water intake are determined individually. There is free access to feed and water during the experiment.

The test substances are administered orally in a vehicle and always tested by comparison with the vehicle control which is run in parallel. The vehicle itself has no influence on the feed intake, and is normally hydroxyethylcellulose (0.5% in water) or Solutol HS15 (5% in hydroxyethylcellulose (0.5% in water)). A corresponding group of slim mice is kept for each group of diet-induced obese mice.

Feed consumption and water consumption are determined each day in the first week and then once per week by reweighing the offered feed and water, respectively. The body weight is measured each day.

Blood samples are taken before and at the end of the treatment in order to determine serum parameters which provide information about changes in intermediary metabolism. It is additionally possible to determine the body fat content on the living animal by means of an impedance measurement (TOBEC method).

For the intended effects on parameters such as food uptake and body weight development, it is desirable that an antagonist of MCH1R has sufficient brain penetration (for example determined as the ratio of the compound level in the brain tissue and in the blood serum attained at one time) (on this subject, see, for example, J. Pharmacol, Exp. Thera. 2008, 324, 206-213). Preferred compounds of the invention have a ratio of brain to serum levels of at least 0.3. Further preferred compounds have a ratio of at least 0.6. Particularly preferred compounds exhibit a ratio of at least 1.0.

Micronucleus Test (in vitro)

The aim of the micronucleus test (in vitro) is to examine whether a test compound has the potential to elicit the formation of micronuclei (small membrane-bound DNA fragments) in various cell lines or primary cultures, with or without metabolic activation by S9 liver homogenate. The test system allows differentiation between the clastogenic and aneugenic potential of a test compound by an immunochemical labeling of the kinetochores or by staining the DNA fragments by the FISH (fluorescence in situ hybridization) method.

Brief description: The cells are treated in a 96-well microtiter plate with the test compound. The treatment time is typically 3 hours with metabolic activation or 24 hours without metabolic activation. Twenty-four hours after the end of the treatment, the cells are isolated, fixed and stained. The cytotoxicity of the test compound is assessed according to the relative cell growth expressed as percentage growth or taking account of the doubling time as population doubling compared with the negative control. The highest test concentration should show not less than 30% surviving cells, or should be the concentration at which a precipitate of the test compound is observed. Duplicate determinations should be carried out with each test concentration. An accurate detailed description of the experiment is to be found in Kirsch-Volders et al. (Mutation Res. 2003, 540, 153-163).

Evaluation: The structural or numerical chromosomal damage is reported as the increase in the number of cells with micronuclei in an ensemble of 1000 cells at three analyzable test concentrations. The test is regarded as positive in the following cases:
 a) the increase in the number of cells with micronuclei is significant by comparison with the negative control (solvent or untreated), or
 b) the number of micronuclei is increased to a biologically relevant extent, concentration-dependently by comparison with the negative control.

A positive control must show a clear statistically significant effect by comparison with the negative control.

Preferred compounds of the invention are negative in the micronucleus test.

AMES II Test

The aim of the AMES II test is to examine whether a test compound has mutagenic potential.

Brief description: A mixed bacterial strain (mixed strains, 6 different *Salmonella typhimurium* strains with in each case a missence point mutation in the histidine operon) and the *Salmonella typhimurium* strain TA98 for detecting frame shift mutations is treated in a 384-well microtiter plate with various concentrations of the test substance with or without metabolic activation through addition of S9 liver homogenate (accurate descriptions of the experiment are to be found in the literature: P. Gee, D. M. Maron, B. N. Ames; Proc. Natl. Acad. Sci. USA 1994, 91, 11606 and Flückiger-Isler et al.; Mutation Res. 2004, 558, 181 and cit. lit.).

Mutagenic test compounds cause back-mutations and thus restore the functionality of endogenous histidine biosynthesis. Mutated bacteria are thus able to divide and expand to bacterial colonies.

Evaluation: If there is enhanced bacterial growth owing to mutations of the bacteria, then enzymes are digested in the growth medium. As a result, the pH in the medium falls and the color of the added indicator (bromocresol purple) changes from pale violet to yellow. The test is regarded as positive if the number of wells in which a color change is observed per concentration increases significantly by comparison with the control.

Preferred compounds of the invention are negative in the AMES II test.

Cytotoxicity Tests a) LDH Release

The aim of the test for LDH (lactate dehydrogenase) release is to examine whether a compound damages the integrity of the cell wall and may thus cause cell death.

Brief description: The LDH activity which enters the cell supernatant from the cytosol due to cell damage is measured by colorimetry. The cells are treated with the test compound. Fifty microliters of the culture supernatant are removed and mixed with the reaction solution (LDH kit, Roche, Mannheim) in accordance with the manufacturer's information. LDH catalyzes the conversion of lactate into pyruvate. During this, NAD+ is reduced to NADH/H+. The latter in turn reduces, under the influence of the added diaphorase, a likewise added yellow tetrazolium salt to the red formazan.

Evaluation: The formazan is quantified by measuring the absorption at 492 nM (e.g. with TECAN SPECTRAFluor Plus).

Preferred compounds of the invention show no significant increase in LDH activity at concentrations below 10 µM. Particularly preferred compounds show no increase below a concentration of 50 µM. Even further preferred compounds show no increase below a concentration of 250 µM.

b) Intracellular ATP Content

The aim of the test is to determine the total intracellular ATP content, which is a measure of the energy level and thus the vitality of a cell.

Brief description: 100 µl of cell culture medium are mixed in a well of a microtiter plate with 100 µl of the CellTiter-Glo reagent (following the manufacturer's instructions: Promega Technical Bulletin No. 228, CellTiter-Glo Luminescent Cell Viability Assay), The cultures are shaken at room temperature for 2 minutes and then incubated for 10 minutes until the luminescence signal has stabilized.

Evaluation: The luminescence is recorded, integrating over one second (e.g. with TECAN SPECTRAFluor Plus).

Preferred compounds of the invention show no significant reduction in the ATP levels at concentrations below 10 µM. Particularly preferred compounds show no reduction below a concentration of 50 µM. Even further preferred compounds show no reduction below a concentration of 250 µM.

c) Neutral Red Uptake

The aim of the test is to measure the uptake of neutral red (NR) into the lysosomes/endosomes and vacuoles of living cells, which is a quantitative measure of the number and vitality of the cells.

Brief description: The cells are washed with 150 µl of a preheated phosphate buffer solution (PBS) and incubated with 100 µl of the NR medium at 37° C. in a humidified atmosphere with 7.5% carbon dioxide for 3 hours. After the incubation, the NR medium is removed and the cells are washed with 150 µl of PBS. Removal of the PBS is followed by addition of exactly 150 µl of an ethanol/glacial acetic acid solution. After shaking for 10 minutes, the dye is extracted from the cells to give a homogeneous dye solution. An exact description of the test is to be found in the literature (E. Borenfreund, J. A. Puerner, Toxicol. Lett. 1985, 24(2-3), 119-124).

Evaluation: The absorption of the dye solution is determined at 540 nM using a microtiter plate reader as difference from the absorption of the ethanol/glacial acetic acid solution.

HERG Channel Blockade

The aim of the test is to determine the concentration range in which the test compound blocks the cardiac hERG channel. Blockade of the hERG channel, which is responsible for the Ikr current in the human heart, is associated with potentially fatal arrhythmias.

For expression of the cDNA encoding the hERG channel it was cloned into the pcDNA3 vector (Invitrogen). Chinese hamster oocytes (CHO, American Type Culture Collection, Rockville, Md.) were transfected using lipofectamine (GIBCO/BRL, Grand Island, N.Y.) with the hERG cDNA and selected using G418 (GIBCO/BRL, Grand Island, N.Y.; 500 µg/ml). CHO cells with stable expression of the hERG channel were cultured on a HAM F-12 medium which was supplemented with 10% native bovine serum, 1× penicillin/streptomycin and 500 µg/ml G418 in an atmosphere of 95% air/5% carbon dioxide.

The cells selected for the patch clamp experiment are seeded on a plastic support 18-24 hours before the experiment. HERG channel currents are recorded at room temperature by the whole-cell variant of the patch clamp technique using an Axopatch 200B amplifier (Axon Instruments, Foster City, Calif.). The electrodes (3-6 megaohms resistance) are prepared from TW150F glass capillaries (World Precision Instruments, Sarasota, Fla.) and filled with the pipette solution (120 mM potassium aspartate, 20 mM KCl, 4 mM Na2ATP, 5 mM HEPES, 1 mM MgCl2; adjusted to pH 7.2 with KOH). The hERG channel currents are induced by a positive voltage pulse (20 mV) followed by a negative pulse (−40 mV) and are recorded for later analysis. As soon as the hERG channel current of the cell flushed with the control solution (130 mM NaCl, 5 mM KCl, 2.8 mM NaOAc, 1 mM MgCl2, 10 mM HEPES; 10 mM glucose, 1 mM CaCl2; adjusted to pH 7.4 with NaOH) is stable, the cell is perfused with the test compound dissolved in the above control solution (by dilution of a 10 or 100 mM DMSO solution of the test compound so that the DMSO content is no more than 0.1%). The current is followed continuously until no further changes occur. The same procedure is repeated with increasing concentrations of the test compound. The maximum amplitude of the hERG current is measured in picoAmperes (pA) for each concentration and for each cell. The maximum amplitude in pA for each concentration of the test compound is compared with that of the pure control solution in the same cell and calculated as % of the control value.

Evaluation: The test compound is tested at various concentrations in 3-5 CHO cells which express the hERG channel. The IC50 is obtained by use of nonlinear least squares regression (GraphPAD Software, San Diego, Calif.).

General Selectivity

In order to minimize the risk of unwanted side effects, it is desirable to keep the nonselective effect of biologically important functional units (e.g. receptors, ion channels and enzymes; for lists, see, for example, Whitebread, S. et al.; Drug Discovery Today 2005, 10, 1421-33 and Rolland, C. et al., J. Med. Chem. 2005, 48, 6563-6574) by an active pharmaceutical ingredient as small as possible. General selectivity tests in a large number of in vitro test systems can be carried out by various specialized services (e.g. Cerep, Panlabs).

The compounds of the invention of the formula I exhibit, as selective MCH1R antagonists, selectivity factors of at least 30, preferably of 100, more preferably of 300 and even more preferably of 1000 vis à vis the affinity to other proteins. Examples of such proteins are serotonin receptor subtypes (e.g. the 5-HT2a receptor), muscarine receptor subtypes (e.g. the M1 receptor), adrenergic receptor subtypes (e.g. AR alpha1a), sodium and calcium channels (e.g. the L-type calcium channel).

Solubilities in Aqueous Systems

Adequate solubility of a substance in aqueous solvent systems is an important prerequisite for a (reproducible) pharmacological effect. Solubilities in aqueous systems can be determined by various methods. Suitable examples are solution precipitation methods ("kinetic solubility") and methods which investigate the dissolution of a solid sample until an equilibrium is set up ("thermodynamic solubility").

a) Kinetic Solubility

A DMSO solution of the test compound (2.5 mM; 0.5 µl) is pipetted into 200 µl of an aqueous test solution (e.g. phosphate-buffered saline, 10×, 1M, Sigma, adjusted to 10 mM, pH 7.4) in a 96-well microtiter plate, and the turbidity is measured at the resulting theoretical concentration for the test compound of 6.25 µM using a nephelometer (e.g. Nephelostar Galaxy, BMG Labtech). The concentration of the test compound in the aqueous test solution is then raised to a theoretical 12.5 µM by adding further DMSO solution (2.5 mM; 0.5 µl), and the turbidity measurement is repeated. Further additions of DMSO solutions (1 µl, 2.5 mM; 0.5 µl, 10 mM; then 9×1 µl, 10 mM resulting in theoretical concentrations of 25 µM, 50 µM, 100 µM, 150 µM, 200 µM, 250 µM, 300 µM, 350 µM, 400 µM, 450 µM and 500 µM) with turbidity measurement in between complete the measurement process.

Evaluation: The turbidity values from the nephelometer are plotted against the theoretical concentration of the test compound in the aqueous test solution. As soon as a significant turbidity is detected (e.g. 5 times above the control value of the aqueous test solution) at a theoretical concentration, the level of concentration below this is stated to be the solubility limit of the test compound in the test solution. Thus, the maximum possible measurement range emerges as values<6.25 µM, 6.25-500 µM and >500 µM.

Preferred compounds of the invention show a kinetic solubility in phosphate buffer (pH 7.4) of at least 12.5 µM; more preferably of at least 50 µM and even more preferably of at least 250 µM.

b) Thermodynamic Solubility

The integrated UV absorption from HPLC UV measurement of serial dilutions of the test compound in DMSO (500 µM, 100 µM, 50 µM, 10 µM and 1 µM) shows a linear correlation with the concentration in a calibration line. The test compound (500 µg) is shaken together with the aqueous test solution (250 µl) in a closed vessel (capacity: 1.5 ml) for 16 hours (Eppendorf thermoshaker, 1400 rpm, 25° C., covering to protect from light). The sample is then centrifuged at maximum rotational speed, and the supernatant is finally filtered. A sample of the filtered supernatant is analyzed directly by HPLC UV measurement (see above). A further sample is analyzed after dilution (1 part by volume of supernatant, 39 parts by volume of test solution).

Evaluation: The concentration of the test compound in the undiluted supernatant is calculated from the resulting integrated UV absorptions of the supernatant samples on the basis of the constructed calibration line and stated as solubility of the test compound in the respective aqueous test solution.

Examples of aqueous test solutions are deionized water or aqueous phosphate buffers with various pH values (e.g. pH 1.2; pH 4.0; pH 6.8; pH 7.4; pH 9.0) which can be prepared from the commercial solution (phosphate buffered saline, 10×, Sigma) by dilution and adjustment with phosphoric acid or sodium hydroxide solution by standard methods.

Preferred compounds of the invention show a solubility in phosphate buffer (pH 7.4) of at least 12.5 µM; more preferably of at least 50 µM and even more preferably of at least 250 µM.

Permeability

The test for permeability is carried out in CACO-2/TC7 cells which have been cultured (DMEM/Glutamax 1/Gibco with high glucose content, HEPES 25 mM, 1% NEAA, 10% FBS, 40 µg/ml gentamycin; 37° C. surrounding temperature; 95% humidity and 10% CO2 content) on Becton Dickinson filters (24-well, uncoated) for 21 days. The permeability is tested at a concentration of 20 µM for the test compound (1% DMSO in HBSS) with a pH gradient (apical: pH 6.5 and 0.5% BSA; basolateral: pH 7.4 and 5% BSA). Analysis takes place by means of LCMS/MS. Further descriptions of the test system and references for the experimental procedure are to be found in Balimane, P.V.; Drug Discovery Today 2005, 10(5), 335-343.

Inhibition of CYP Enzymes

The inhibition of CYP enzymes is determined on recombinant enzymes (obtained from Becton Dickinson) and fluorescent substrates (BD/Gentest) as recommended by the manufacturer (see website http://www.bdbiosciences.com). Further descriptions of the test system and references for the experimental procedure are to be found in Zlokarnik, G.; Drug Discovery Today 2005, 10(21), 1443-1450.

Metabolic Stability

The metabolic stability is determined by incubating the test compound (5 µM) with microsomal liver fractions (1 mg/ml protein with 0.1% w/v BSA; 1 mM NADPH, 0.5% DMSO) at 37° C. Analysis at an incubation time of 0 and 20 minutes takes place by means of LCMS/MS. Further descriptions of the test system and references for the experimental procedure are to be found in Plant, N.; Drug Discovery Today 2004, 9(7), 328-336 and Lau, Y.Y. et al.; Pharmaceutical Res. 2002, 19(11), 1606-1610.

EXAMPLES

The examples and preparation methods adduced below serve to illustrate the invention, but without limiting it.

The inventive compounds of the formula I can be prepared with the aid of reactions known in principle. For example, an amino acid of the structure Z1 can first be protected selectively (for example with Boc2O). The subsequent reaction with an amine (HNR1R2; R1, R2 both not H) can advantageously be carried out using a commonly known coupling reagent (for example with HATU or by method C with EDC/HOBt). Removal of the Boc protecting group (for example with hydrochloric acid) and subsequent reduction (for example by method I with lithium aluminum hydride) gives rise to an amine of structure Z2 (where R8=H). When one carbamate protecting group is not removed before the reduction, Z2 is obtained with R8=methyl. In a last step, the inventive compounds of the formula Ia can be obtained by reacting the amine Z2 with an acid of the structure B-L2-A-CO2H (for example by method C) (scheme 1).

Scheme 1

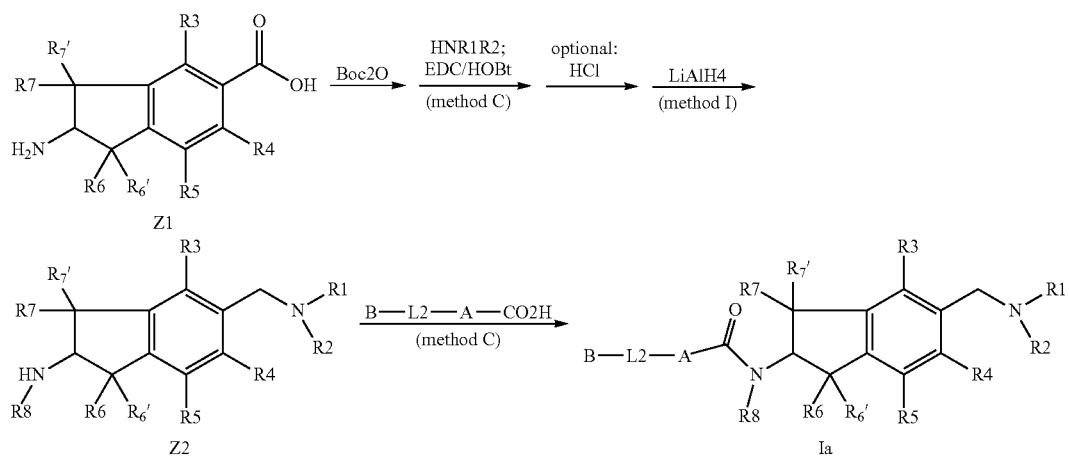

Further compounds of the Ia type can be obtained by reacting the intermediates Z2 with carboxylic acids of the structure HO-A-COOH (for example by method C) and subsequent alkylation with appropriate alkylating agents (for example by method G with alkyl bromides, alkyl iodides or alkylsulfonic esters). Secondary amines of the Ia type (R2=H) are obtained when, for example, an amine of the HNR1 (PMB) structure is used in the first amide coupling step, and the para-methoxybenzyl (PMB) group is eliminated in the last step, for example by treatment with trifluoroacetic acid at elevated temperature.

Alternatively, compounds of the formula I can be obtained from 5-bromoindan-2-ylamines (Z3). The latter are either commercially available in enantiomerically enriched form or can be obtained in such a form from racemates by generally customary methods (for example by chromatography on a chiral phase). Reaction with acids of the B-L2-A-CO2H structure (for example by method C) gives rise to the intermediates Z4. These can be converted by literature methods to the arylcarbonyl compounds Z5 (see, for example, J. Am. Chem. Soc. 2000, 122, 6935; J. Med. Chem. 2005, 48, 1948; Angew. Chem. Int. Ed. 2006, 45, 154). Final reductive amination leads to the compounds Ib (scheme 2).

Scheme 2

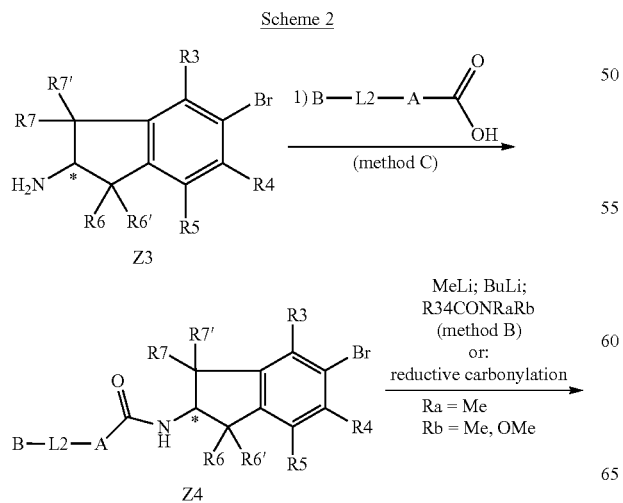

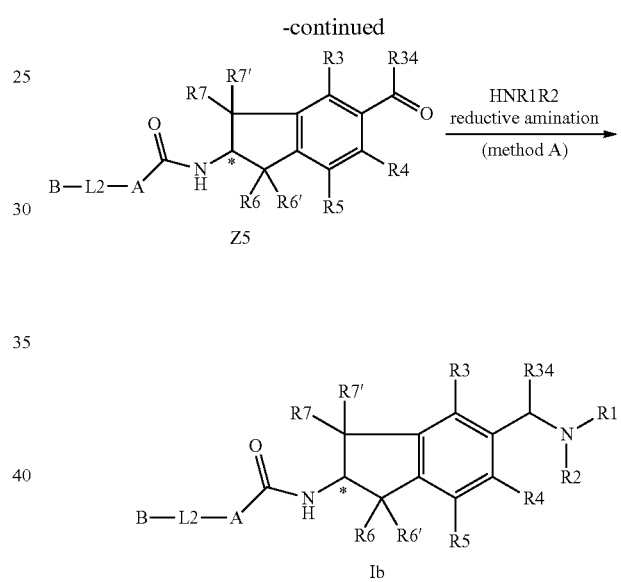

Stereochemically defined compounds of type Ib* can be formed, for example, by condensation of the intermediates Z5' with chiral sulfinylamides, addition of Grignard reagents, hydrolysis and optional reductive alkylation, for example by method A (scheme 2-1).

Scheme 2-1

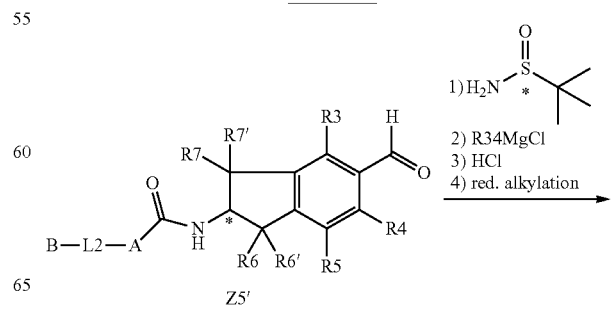

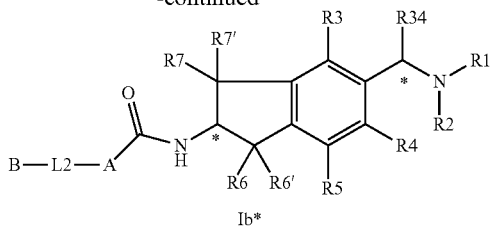

Further intermediates of the Z4 or Z4' type can be obtained by subsequent modification of substituents. For example, methoxy groups (B-L2=MeO) can be cleaved by reagents such as hydrogen bromide or boron tribromide, and the resulting aromatic hydroxyl compounds can be reacted with appropriate alkylating agents (for example by method G with alkyl bromides, alkyl iodides or alkyl sulfonates). Alkylation on the amide nitrogen atom (for example by method D) gives rise to intermediates Z4' where R8=alkyl.

The intermediates Z4' can also be used to synthesize other compounds of the formula I. For this purpose, for example, the dianions obtained by sequential treatment of Z4' (R8=H) with MeLi and then n-BuLi can be reacted with ketones (R34COR35). The resulting tertiary alcohols can be converted under the conditions of the Ritter reaction (e.g. TMSCN, H2SO4/HOAc) to amides which then, after hydrolysis and optional reductive amination, give rise to compounds of the structure Ib-1 (scheme 2-2).

Alternatively, the intermediates Z4' can also be reacted by means of transition metal complexes (for example those of Pd and Ni) catalyzed with pyridyl compounds (e.g. pyridyltrialkyltin compounds, pyridylboronic acid (derivatives) or pyridine N-oxides). Subsequent hydrogenation with suitable catalysts and optional reductive alkylation gives rise to the structures Ib-2 (scheme 2-2).

In one variant, the coupling partners for the intermediates Z4' are stereoselectively metalated pyrrolidines (method J). After elimination of the Boc protecting group and reductive amination (for example by method A), the isomerically enriched structures Ib-3 are obtained.

In another variant, the intermediates Z4' are reacted with allyl-metal compounds (e.g. allyltributyltin or vinyltributyltin) under palladium catalysis (Stille conditions; e.g. method F), then the double bond is cleaved oxidatively (for example with OsO4/NaIO4 by method E), and the aldehydes thus obtained are reacted with amines HNR1R2 in the sense of a reductive amination (scheme 2-2).

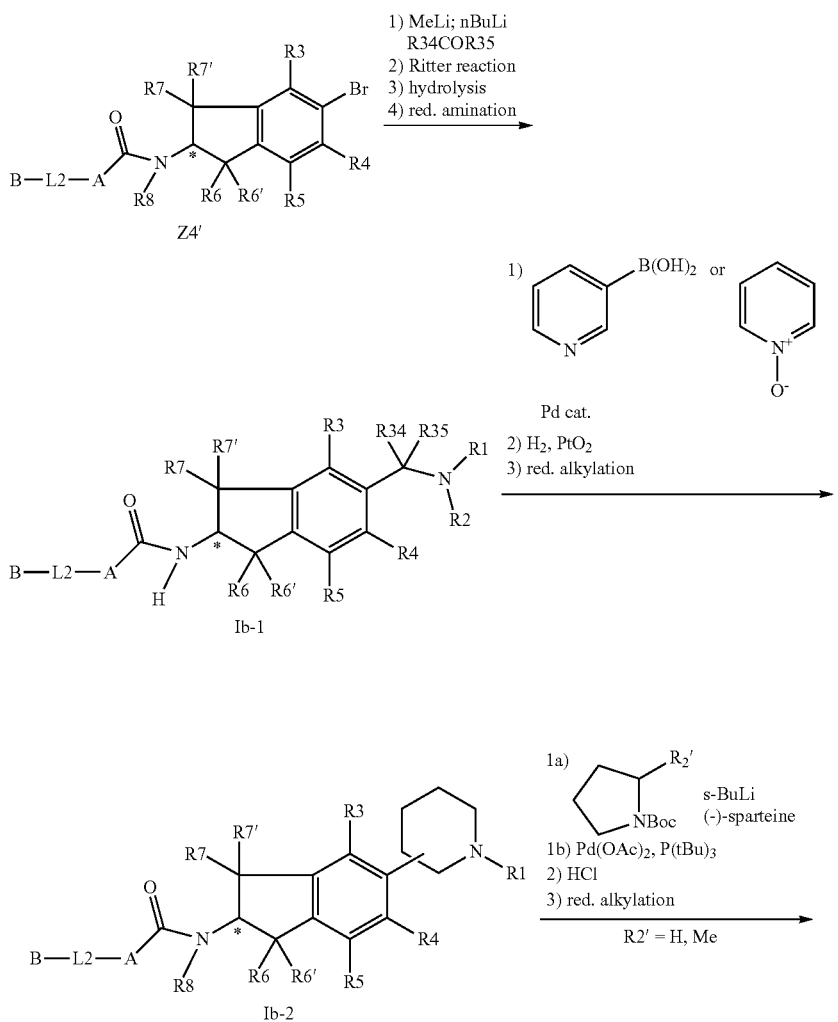

Scheme 2-2

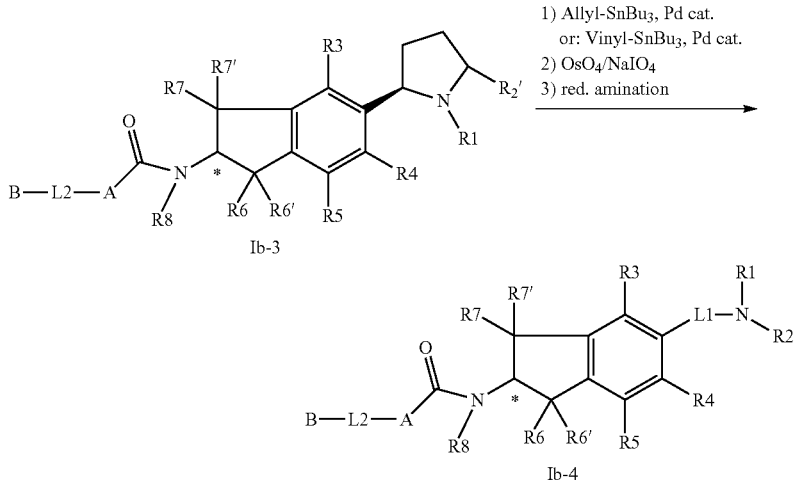

Alkylation (for example with NaH, MeI by method D) on the amide function of the intermediates Z4. Z5 and Z5' and further synthesis along the pathways specified above, and also analogous alkylation of the structures Ib, Ib-1, Ib-2 (R8=H) and Ib-4 (R8=H), give rise to further routes to compounds of the formula I (variation of the substituent R8).

A further preparation process for other compounds of the formula I again consists in reacting dichlorides of the Z6 type or isochromenones of the Z7 type with amines Z8 by processes known in principle (scheme 3). The dichlorides Z6 required can be obtained from ortho-methylbenzoic acids by double metalation, for example with lithium diisopropylamide (LDA), scavenging of the dianion with formaldehyde (for example in the form of paraformaldehyde) and final dichlorination. The amines Z8 can be obtained, for example, according to scheme 1 (Z2 with R8=H) or according to scheme 2 by hydrolysis of the structures Ib.

Scheme 3

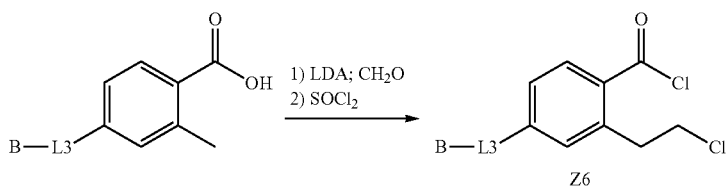

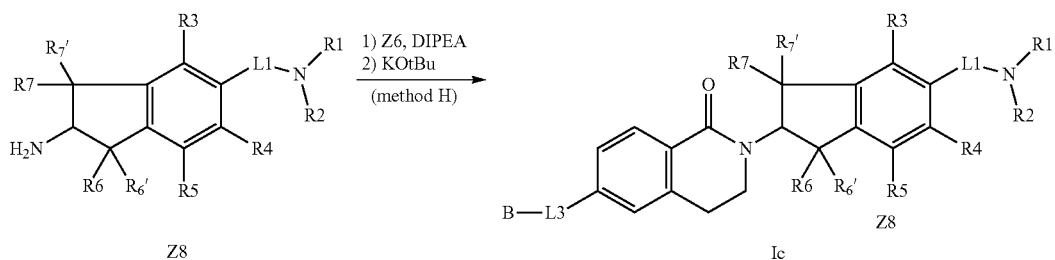

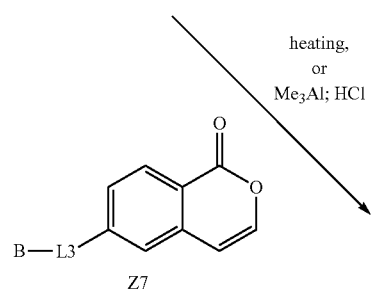

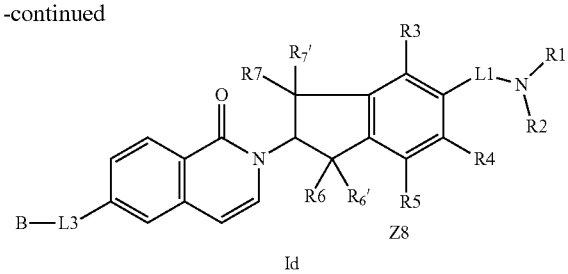

Id

Alternatively, for the synthesis of (dihydro)isoquinolinones of the formula I, it is also possible again to proceed from 5-bromoindan-2-ylamines (Z3). The amines 23 can be reacted with the dichlorides Z6 (or the isochromenones Z7). The bromides Z9 thus prepared can then be converted further to inventive compounds analogously to the intermediates Z4' (preferably by means of the transition metal-catalyzed reactions specified there). For example, the bromides Z9 can be reacted with vinyltributyltin by means of a Stille reaction, the resulting vinyl-aryl compounds can be cleaved oxidatively by method E, and the aldehydes thus obtained can be converted to compounds of the Ie type by means of a reductive amination (scheme 3-1).

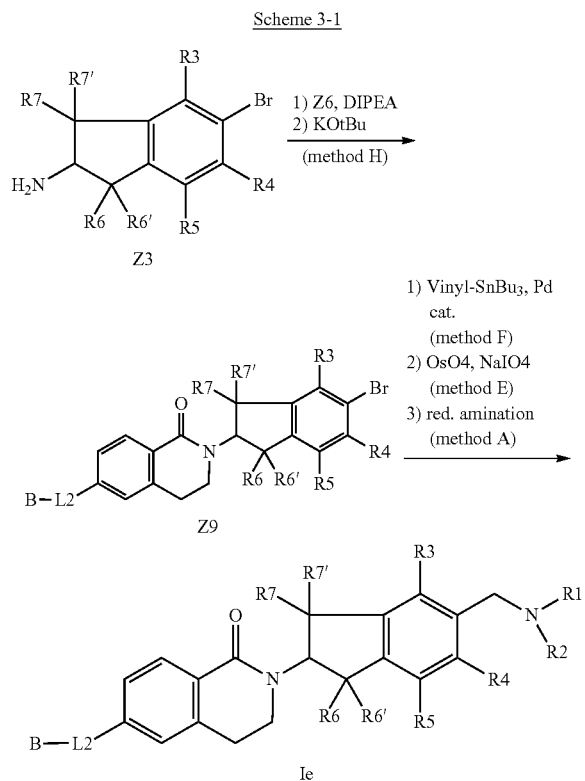

Descriptions of the general methods used can be found, by way of example, at the following points:
methods A, B, C, D, E, F, G, H, I in example 1;
method J in example 2.
General Explanations
a) Salt Forms
Many of the inventive compounds are bases and can form salts with correspondingly strong acids. In particular, the compounds, after HPLC purification using an eluent comprising trifluoroacetic acid, may be present in the form of hydrotrifluoroacetates. These can be converted to the free bases shown by simple treatment of a solution of the salts, for example with sodium carbonate solution.
b) Units of the Characterization Data
The unit of the isotope-averaged molecular weights reported for starting materials/intermediates is "g/mol". For examples, the monoisotopic molecular weight is reported as a multiple of the atomic unit mass.

Example 1-1

Table 1

4-Cyclopropylmethoxy-N-((R)-5-{[(tetrahydropyran-4-ylmethyl)amino]methyl}indan-2-yl)-benzamide

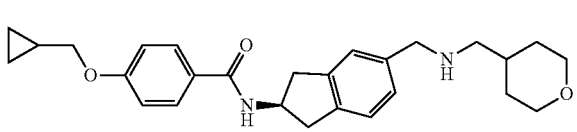 [SMILES: O=C(N[C@@H]1Cc2ccc(CNCC3CCOCC3)cc2C1)c1ccc(OCC2CC2)cc1]

Method A
To a mixture of 4-cyclopropylmethoxy-N-((R)-5-formylindan-2-yl)benzamide (0.10 g), THF (1 ml), methanol (0.5 ml), C-(tetrahydropyran-4-yl)methylamine (51 mg) and acetic acid (36 mg) was added polymer-bound sodium cyanoborohydride (0.60 mmol), and the suspension was shaken at room temperature for 12 hours. The polymer was filtered off with suction, and the filtrate was concentrated. The residue was purified by preparative HPLC. The product was thus obtained with the monoisotopic molecular weight of 434.26 (C27H34N2O3); MS (ESI): 435.2 (M+H+).

4-Cyclopropylmethoxy-N-((R)-5-formylindan-2-yl)benzamide

Method B
A mixture of N-((R)-5-bromoindan-2-yl)-4-cyclopropylmethoxybenzamide (6.70 g) and THF (67 ml) was cooled to −78° C. (dry ice bath), and a solution of methyllithium (7.5 ml; 3 M) was added dropwise. One minute after the addition had ended, a solution of butyllithium (10 ml; 2.5 M in toluene) was added dropwise. One minute after the addition had ended, DMF (3.8 g) and, after a further 30 seconds, acetic acid (1.5 ml) were added. After warming to room temperature, the reaction mixture was diluted with water and extracted with ethyl acetate. The organic phases were dried over magnesium sulfate and concentrated. This afforded the product with the molecular weight of 335.41 (C21H21NO3); MS (ESI): 336 (M+H+).

N-((R)-5-Bromoindan-2-yl)-4-cyclopropylmethoxybenzamide

Method C

A mixture of 4-cyclopropylmethoxybenzoic acid (4.06 g), DMF (100 ml), 1-ethyl-3-(3-dimethylaminopropyl)carbodiimide (hydrochloride, 4.09 g) and 1-hydroxybenzotriazole (2.88 g) was admixed after 5 minutes with diisopropylethylamine (7.1 ml) and (R)-5-bromo-indan-2-ylamine (hydrochloride, 5.00 g). After 4 hours, the reaction mixture was poured into water and the precipitate which formed was filtered off with suction. This afforded the product with the molecular weight of 386.29 (C20H20BrNO2); MS (ESI): 386 (M+H+).

Table 1 lists compounds which were obtained from the corresponding aromatic aldehydes and amines by method A.

TABLE 1

| Structure | Ex. No. | Empirical formula | Molecular weight | [M + H] + ESI-MS |
|---|---|---|---|---|
| 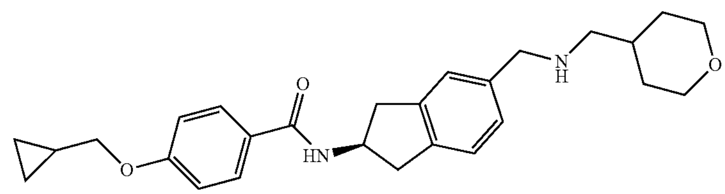 [SMILES: O=C(N[C@@H]1Cc2ccc(CNCC3CCOCC3)cc2C1)c1ccc(OCC2CC2)cc1] | 1-01 | C27H34N2O3 | 434.26 | 435.2 |
| 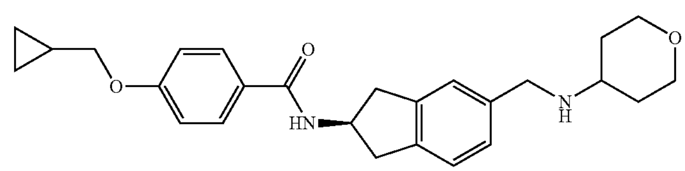 [SMILES: O=C(N[C@@H]1Cc2ccc(CNC3CCOCC3)cc2C1)c1ccc(OCC2CC2)cc1] | 1-02 | C26H32N2O3 | 420.24 | 421.2 |
| 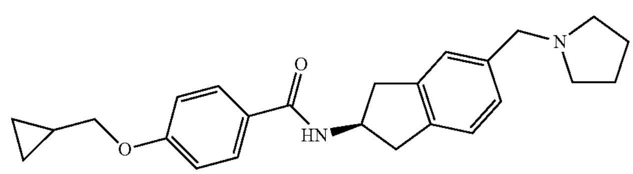 [SMILES: O=C(N[C@@H]1Cc2ccc(CN3CCCC3)cc2C1)c1ccc(OCC2CC2)cc1] | 1-03 | C25H30N2O2 | 390.23 | 391.2 |
| 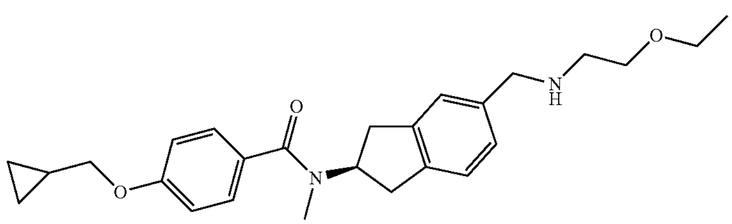 [SMILES: CCOCCNCc1ccc2c(c1)C[C@H](N(C)C(=O)c1ccc(OCC3CC3)cc1)C2] | 1-04 | C26H34N2O3 | 422.26 | 423.3 |
| 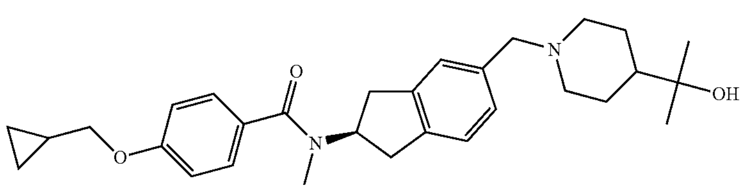 [SMILES: CN(C(=O)c1ccc(OCC2CC2)cc1)[C@@H]1Cc2ccc(CN3CCC(C(C)(C)O)CC3)cc2C1] | 1-05 | C30H40N2O3 | 476.3 | 477.3 |
| 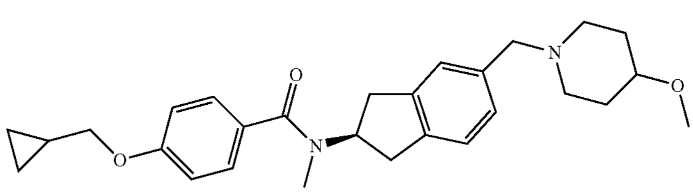 [SMILES: COC1CCN(Cc2ccc3c(c2)C[C@H](N(C)C(=O)c2ccc(OCC4CC4)cc2)C3)CC1] | 1-06 | C28H36N2O3 | 448.27 | 449.3 |

TABLE 1-continued
| Structure | Ex. No. | Empirical formula | Molecular weight | [M + H]+ ESI-MS |
|---|---|---|---|---|
| 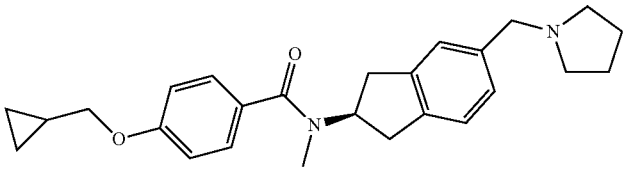 [SMILES: CN(C(=O)c1ccc(OCC2CC2)cc1)[C@@H]1Cc2ccc(CN3CCCC3)cc2C1] | 1-07 | C26H32N2O2 | 404.25 | 405.2 |
| 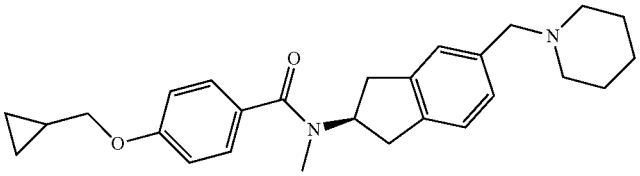 | 1-08 | C27H34N2O2 | 418.26 | 419.2 |
| 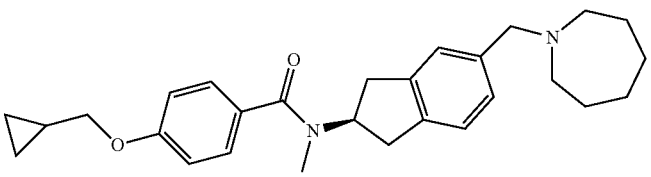 [SMILES: CN(C(=O)c1ccc(OCC2CC2)cc1)[C@@H]1Cc2ccc(CN3CCCCCC3)cc2C1] | 1-09 | C28H36N2O2 | 432.28 | 433.2 |
| 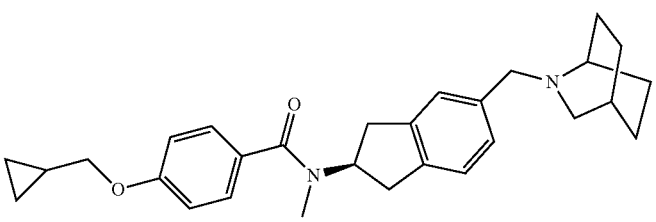 [SMILES: CN(C(=O)c1ccc(OCC2CC2)cc1)[C@@H]1Cc2ccc(CN3CC4CCC3CC4)cc2C1] | 1-10 | C29H36N2O2 | 444.28 | 445.2 |
| 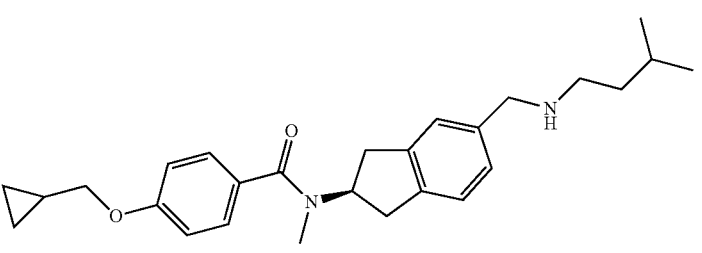 [SMILES: CC(C)CCNCc1ccc2c(c1)C[C@H](N(C)C(=O)c1ccc(OCC3CC3)cc1)C2] | 1-11 | C27H36N2O2 | 420.28 | 421.2 |
| 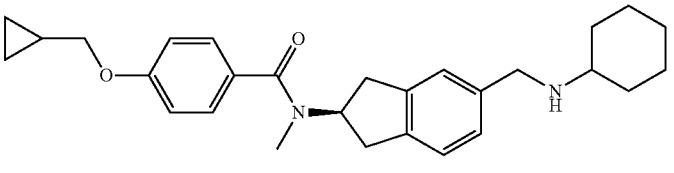 [SMILES: CN(C(=O)c1ccc(OCC2CC2)cc1)[C@@H]1Cc2ccc(CNC3CCCCC3)cc2C1] | 1-12 | C28H36N2O2 | 432.28 | 433.2 |
| 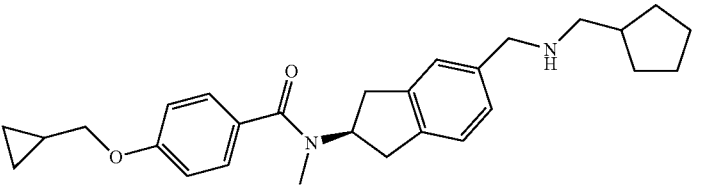 | 1-13 | C28H36N2O2 | 432.28 | 433.2 |
| 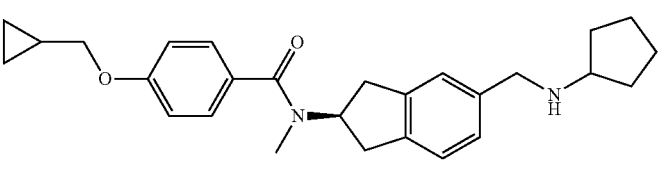 [SMILES: CN(C(=O)c1ccc(OCC2CC2)cc1)[C@@H]1Cc2ccc(CNC3CCCC3)cc2C1] | 1-14 | C27H34N2O2 | 418.26 | 419.2 |

TABLE 1-continued

| Structure | Ex. No. | Empirical formula | Molecular weight | [M + H]+ ESI-MS |
|---|---|---|---|---|
| 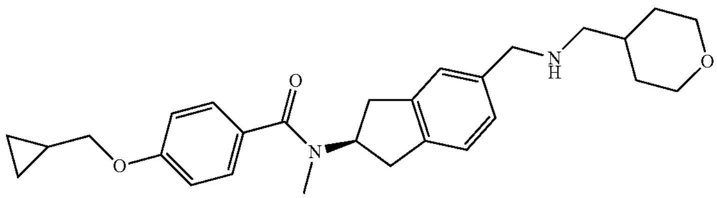 [SMILES: CN(C(=O)c1ccc(OCC2CC2)cc1)[C@@H]1Cc2ccc(CNCC3CCOCC3)cc2C1] | 1-15 | C28H36N2O3 | 448.27 | 449.2 |
| 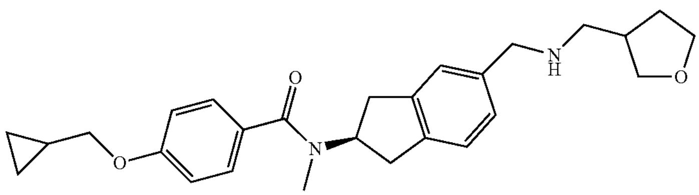 [SMILES: CN(C(=O)c1ccc(OCC2CC2)cc1)[C@@H]1Cc2ccc(CNCC3CCOC3)cc2C1] | 1-16 | C27H34N2O3 | 434.26 | 435.2 |
| 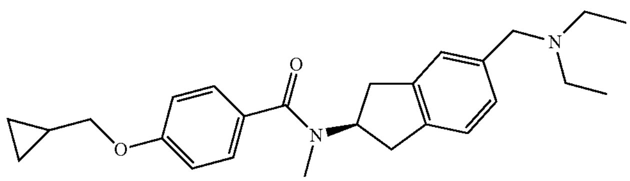 [SMILES: CCN(CC)Cc1ccc2c(c1)C[C@H](N(C)C(=O)c1ccc(OCC3CC3)cc1)C2] | 1-17 | C26H34N2O2 | 406.26 | 407.2 |
| 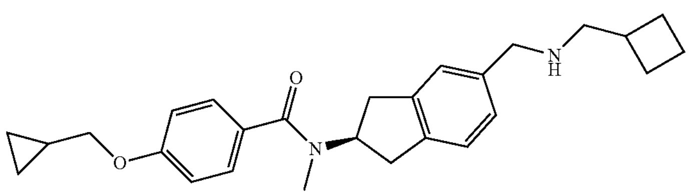 [SMILES: CN(C(=O)c1ccc(OCC2CC2)cc1)[C@@H]1Cc2ccc(CNCC3CCC3)cc2C1] | 1-18 | C27H34N2O2 | 418.26 | 419.2 |
| 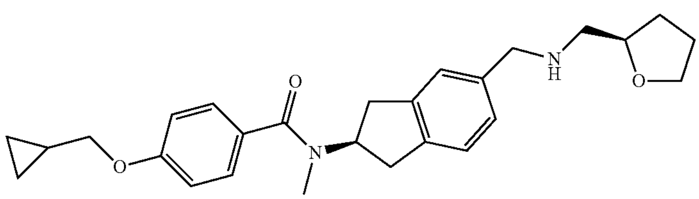 [SMILES: CN(C(=O)c1ccc(OCC2CC2)cc1)[C@@H]1Cc2ccc(CNC[C@H]3CCCO3)cc2C1] | 1-19 | C27H34N2O3 | 434.26 | 435.2 |
| 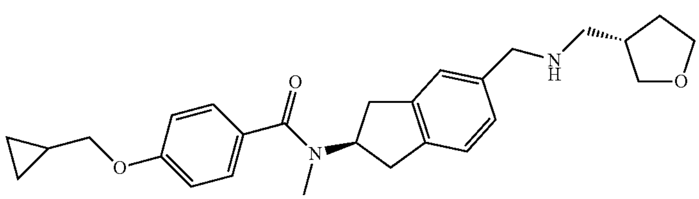 | 1-20 | C27H34N2O3 | 434.26 | 435.2 |
| 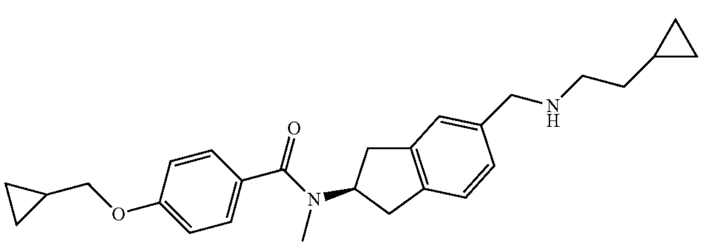 [SMILES: CN(C(=O)c1ccc(OCC2CC2)cc1)[C@@H]1Cc2ccc(CNCCC3CC3)cc2C1] | 1-21 | C27H34N2O2 | 418.26 | 419.3 |

TABLE 1-continued
| Structure | Ex. No. | Empirical formula | Molecular weight | [M + H]+ ESI-MS |
|---|---|---|---|---|
| 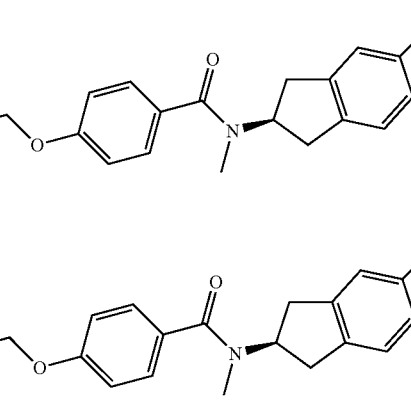 | 1-22 | C28H34N2O2 | 430.26 | 431.2 |
| 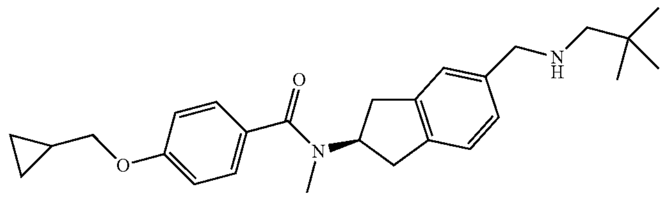 [SMILES: CN(C(=O)c1ccc(OCC2CC2)cc1)[C@@H]1Cc2ccc(CNCC(C)(C)C)cc2C1] | 1-23 | C27H36N2O2 | 420.28 | 421.2 |
| 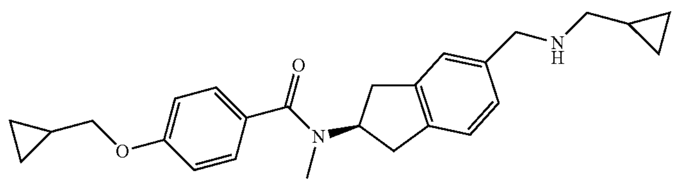 [SMILES: CN(C(=O)c1ccc(OCC2CC2)cc1)[C@@H]1Cc2ccc(CNCC3CC3)cc2C1] | 1-24 | C26H32N2O2 | 404.25 | 405.3 |
| 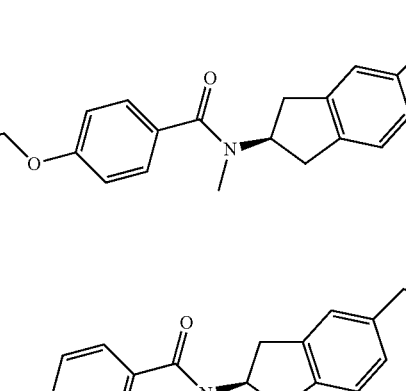 | 1-25 | C29H38N2O3 | 462.29 | 463.3 |
| 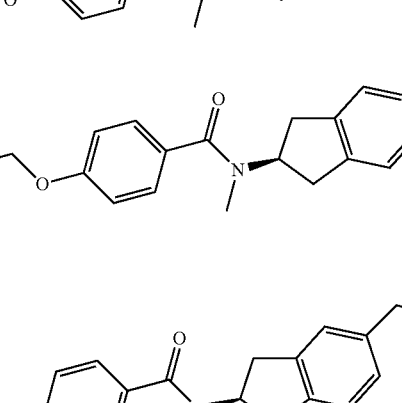 | 1-26 | C28H34N2O2 | 430.26 | 431.3 |
| 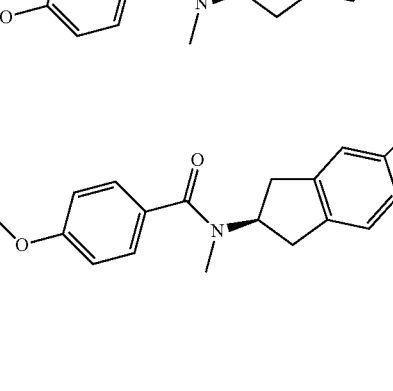 | 1-27 | C26H34N2O3 | 422.26 | 423.3 |
| 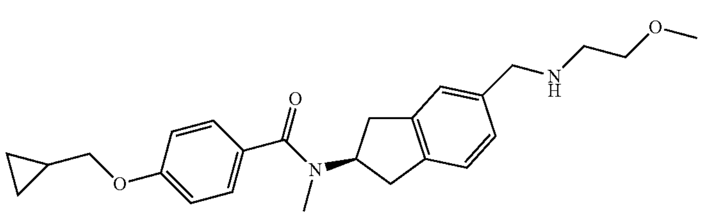 [SMILES: COCCNCc1ccc2c(c1)C[C@H](N(C)C(=O)c1ccc(OCC3CC3)cc1)C2] | 1-28 | C25H32N2O3 | 408.24 | 409.3 |

TABLE 1-continued

| Structure | Ex. No. | Empirical formula | Molecular weight | [M + H] + ESI-MS |
|---|---|---|---|---|
| 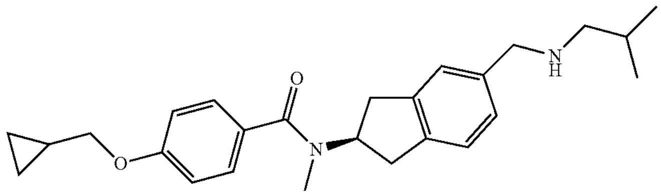 [SMILES: CC(C)CNCc1ccc2c(c1)C[C@H](N(C)C(=O)c1ccc(OCC3CC3)cc1)C2] | 1-29 | C26H34N2O2 | 406.26 | 407.3 |
| 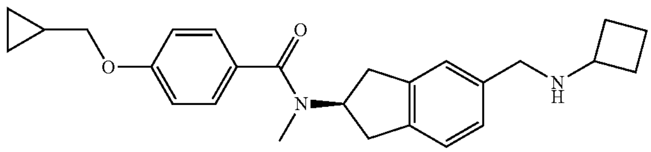 [SMILES: CN(C(=O)c1ccc(OCC2CC2)cc1)[C@@H]1Cc2ccc(CNC3CCC3)cc2C1] | 1-30 | C26H32N2O2 | 404.25 | 405.3 |
| 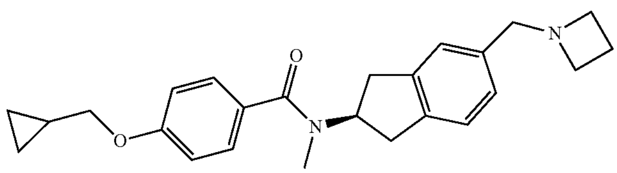 [SMILES: CN(C(=O)c1ccc(OCC2CC2)cc1)[C@@H]1Cc2ccc(CN3CCC3)cc2C1] | 1-31 | C25H30N2O2 | 390.23 | 391.3 |
| 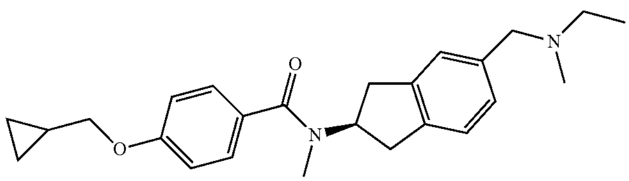 [SMILES: CCN(C)Cc1ccc2c(c1)C[C@H](N(C)C(=O)c1ccc(OCC3CC3)cc1)C2] | 1-32 | C25H32N2O2 | 392.25 | 393.3 |
| 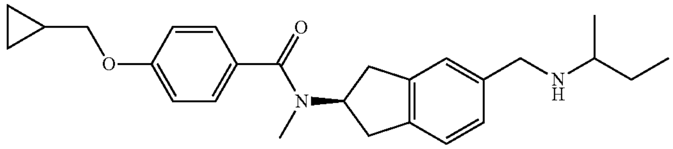 | 1-33 | C26H34N2O2 | 406.26 | 407.3 |
| 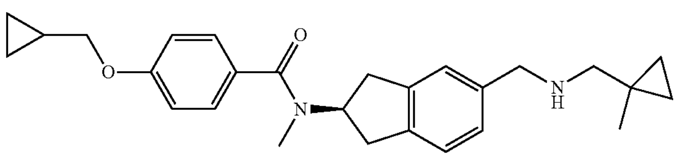 [SMILES: CN(C(=O)c1ccc(OCC2CC2)cc1)[C@@H]1Cc2ccc(CNCC3(C)CC3)cc2C1] | 1-34 | C27H34N2O2 | 418.26 | 419.3 |
| 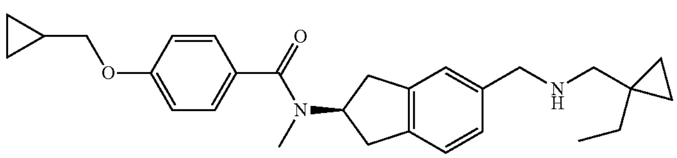 [SMILES: CCC1(CNCc2ccc3c(c2)C[C@H](N(C)C(=O)c2ccc(OCC4CC4)cc2)C3)CC1] | 1-35 | C28H36N2O2 | 432.28 | 433.3 |
| 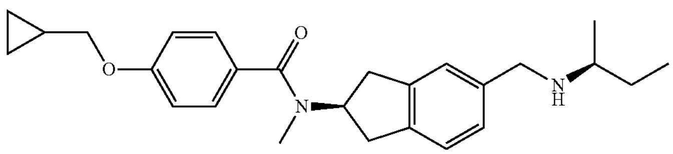 [SMILES: CC[C@H](C)NCc1ccc2c(c1)C[C@H](N(C)C(=O)c1ccc(OCC3CC3)cc1)C2] | 1-36 | C26H34N2O2 | 406.26 | 407.3 |
| 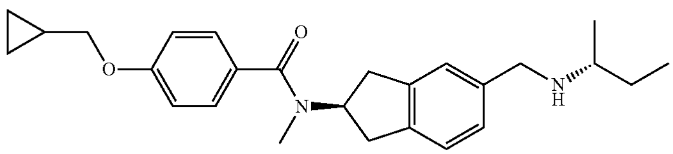 | 1-37 | C26H34N2O2 | 406.26 | 407.3 |

TABLE 1-continued

| Structure | Ex. No. | Empirical formula | Molecular weight | [M + H] + ESI-MS |
|---|---|---|---|---|
| 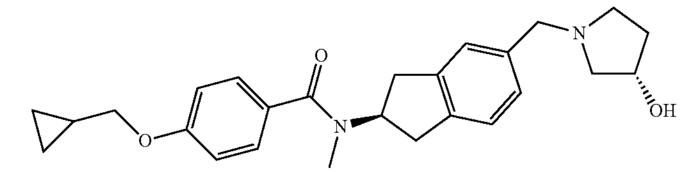 [SMILES: CN(C(=O)c1ccc(OCC2CC2)cc1)[C@@H]1Cc2ccc(CN3CC[C@H](O)C3)cc2C1] | 1-38 | C26H32N2O3 | 420.24 | 421.2 |
| 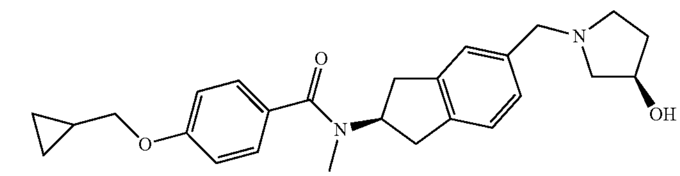 [SMILES: CN(C(=O)c1ccc(OCC2CC2)cc1)[C@@H]1Cc2ccc(CN3CC[C@@H](O)C3)cc2C1] | 1-39 | C26H32N2O3 | 420.24 | 421.2 |
| 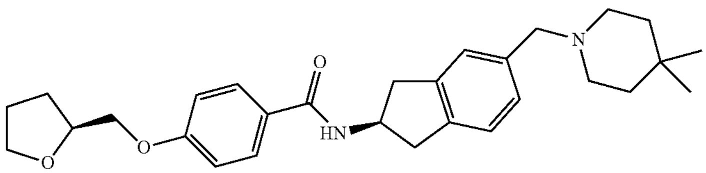 [SMILES: CC1(C)CCN(Cc2ccc3c(c2)C[C@H](NC(=O)c2ccc(OC[C@@H]4CCCO4)cc2)C3)CC1] | 1-40 | C29H38N2O3 | 462.29 | 463.3 |
| 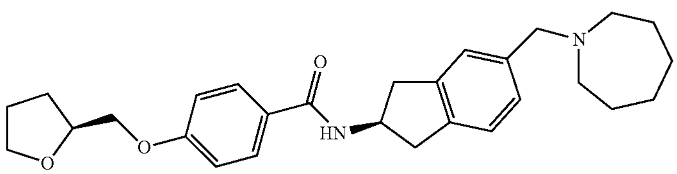 [SMILES: O=C(N[C@@H]1Cc2ccc(CN3CCCCCC3)cc2C1)c1ccc(OC[C@@H]2CCCO2)cc1] | 1-41 | C28H36N2O3 | 448.27 | 449.3 |
| 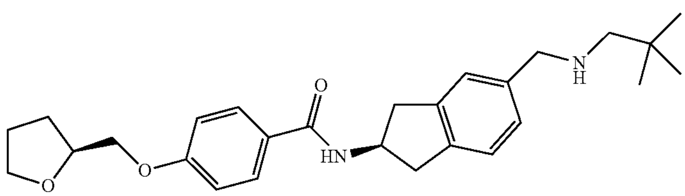 [SMILES: CC(C)(C)CNCc1ccc2c(c1)C[C@H](NC(=O)c1ccc(OC[C@@H]3CCCO3)cc1)C2] | 1-42 | C27H36N2O3 | 436.27 | 437.3 |
| 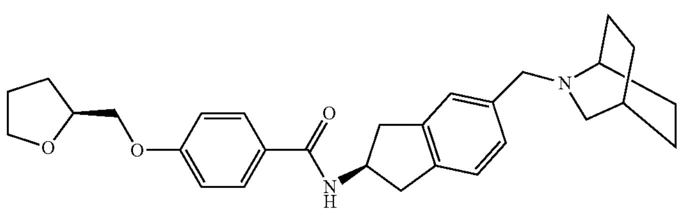 [SMILES: O=C(N[C@@H]1Cc2ccc(CN3CC4CCC3CC4)cc2C1)c1ccc(OC[C@@H]2CCCO2)cc1] | 1-43 | C29H36N2O3 | 460.27 | 461.3 |
| 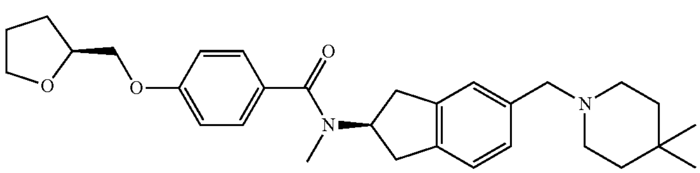 [SMILES: CN(C(=O)c1ccc(OC[C@@H]2CCCO2)cc1)[C@@H]1Cc2ccc(CN3CCC(C)(C)CC3)cc2C1] | 1-44 | C30H40N2O3 | 476.3 | 477.3 |
| 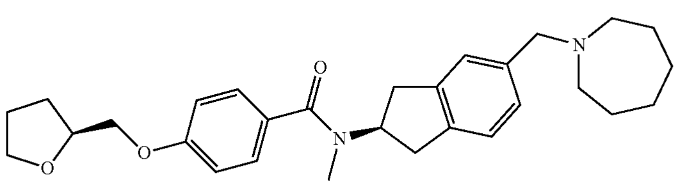 [SMILES: CN(C(=O)c1ccc(OC[C@@H]2CCCO2)cc1)[C@@H]1Cc2ccc(CN3CCCCCC3)cc2C1] | 1-45 | C29H38N2O3 | 462.29 | 463.3 |

TABLE 1-continued
| Structure | Ex. No. | Empirical formula | Molecular weight | [M + H]+ ESI-MS |
|---|---|---|---|---|
| 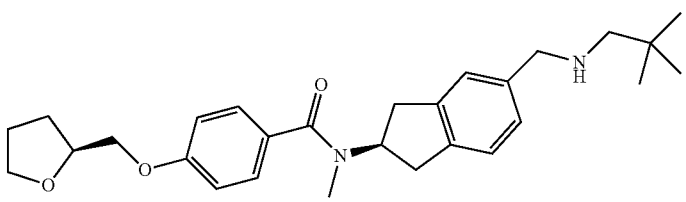 [SMILES: CN(C(=O)c1ccc(OC[C@@H]2CCCO2)cc1)[C@@H]1Cc2ccc(CNCC(C)(C)C)cc2C1] | 1-46 | C28H38N2O3 | 450.29 | 451.3 |
| 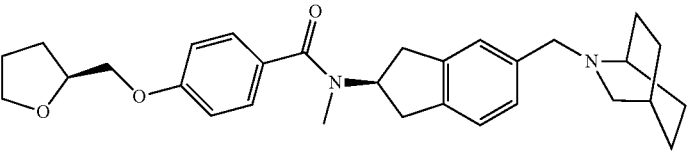 [SMILES: CN(C(=O)c1ccc(OC[C@@H]2CCCO2)cc1)[C@@H]1Cc2ccc(CN3CC4CCC3CC4)cc2C1] | 1-47 | C30H38N2O3 | 474.29 | 475.3 |
| 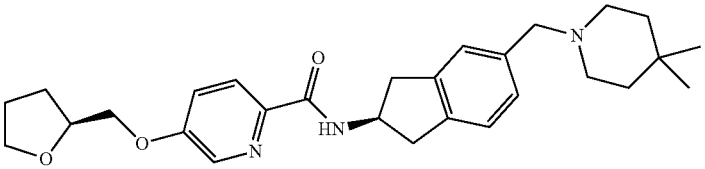 [SMILES: CC1(C)CCN(Cc2ccc3c(c2)C[C@H](NC(=O)c2ccc(OC[C@@H]4CCCO4)cn2)C3)CC1] | 1-48 | C28H37N3O3 | 463.28 | 464.2 |
| 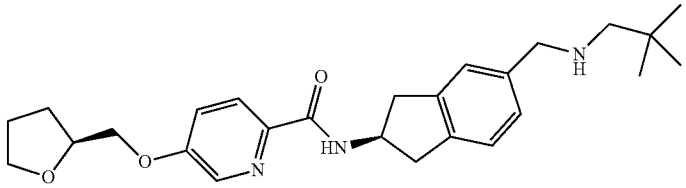 [SMILES: CC(C)(C)CNCc1ccc2c(c1)C[C@H](NC(=O)c1ccc(OC[C@@H]3CCCO3)cn1)C2] | 1-49 | C26H35N3O3 | 437.27 | 438.2 |
| 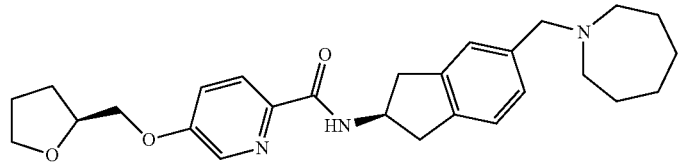 | 1-50 | C27H35N3O3 | 449.27 | 450.2 |
| 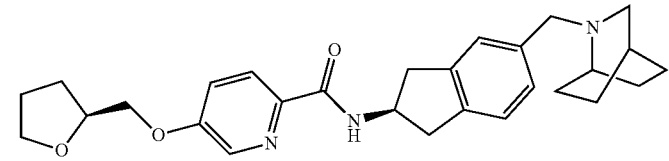 [SMILES: O=C(N[C@@H]1Cc2ccc(CN3CC4CCC3CC4)cc2C1)c1ccc(OC[C@@H]2CCCO2)cn1] | 1-51 | C28H35N3O3 | 461.27 | 462.2 |
| 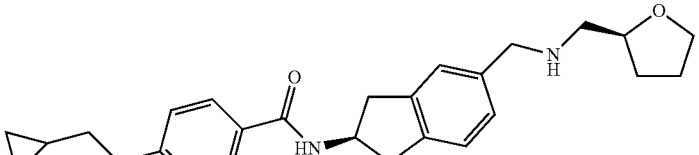 | 1-52 | C25H31N3O3 | 421.24 | 422.3 |
| 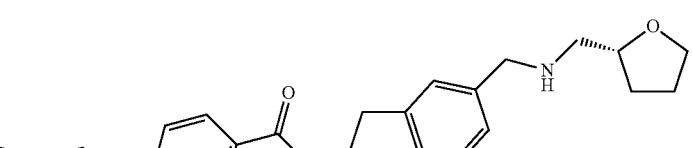 | 1-53 | C25H31N3O3 | 421.24 | 422.3 |

TABLE 1-continued
| Structure | Ex. No. | Empirical formula | Molecular weight | [M + H]+ ESI-MS |
|---|---|---|---|---|
| 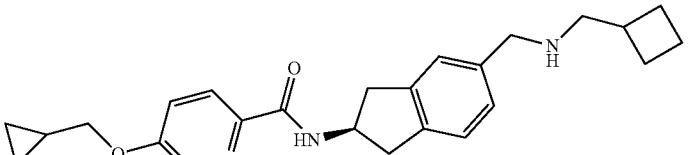 | 1-54 | C25H31N3O2 | 405.24 | 406.3 |
| 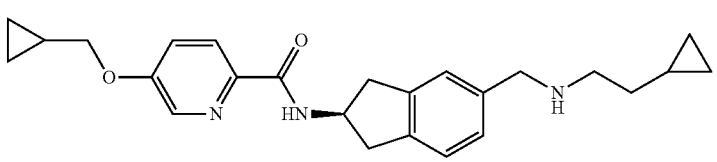 [SMILES: O=C(N[C@@H]1Cc2ccc(CNCCC3CC3)cc2C1)c1ccc(OCC2CC2)cn1] | 1-55 | C25H31N3O2 | 405.24 | 406.3 |
| 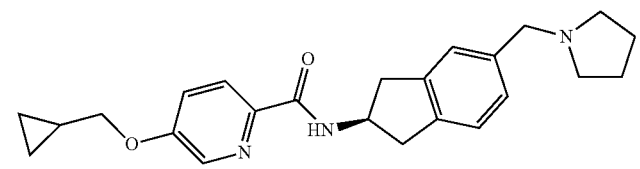 | 1-56 | C24H29N3O2 | 391.23 | 392.3 |
| 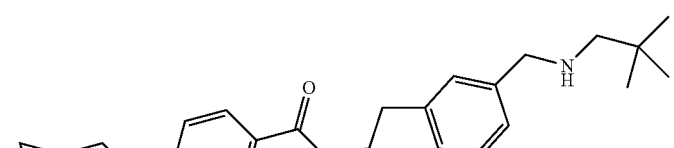 | 1-57 | C25H33N3O2 | 407.26 | 408.3 |
| 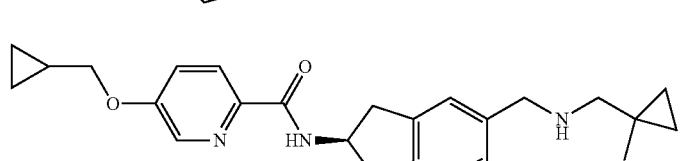 | 1-58 | C25H31N3O2 | 405.24 | 406.3 |
| 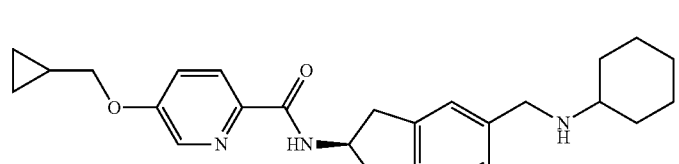 | 1-59 | C26H33N3O2 | 419.26 | 420.3 |
| 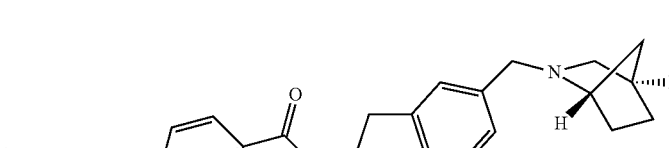 | 1-60 | C26H31N3O2 | 417.24 | 418.3 |
| 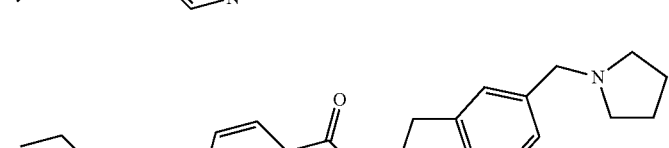 | 1-61 | C25H33N3O2 | 407.26 | 408.3 |

TABLE 1-continued

| Structure | Ex. No. | Empirical formula | Molecular weight | [M + H] + ESI-MS |
|---|---|---|---|---|
| 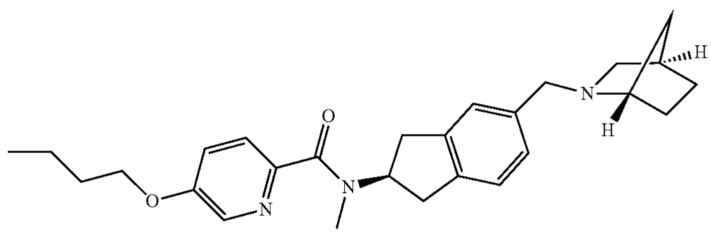 [SMILES: CCCCOc1ccc(C(=O)N(C)[C@@H]2Cc3ccc(CN4C[C@@H]5CC[C@H]4C5)cc3C2)nc1] | 1-62 | C27H35N3O2 | 433.27 | 434.3 |
| 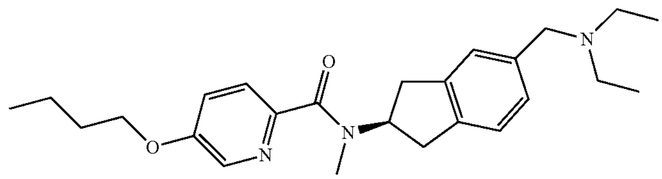 [SMILES: CCCCOc1ccc(C(=O)N(C)[C@@H]2Cc3ccc(CN(CC)CC)cc3C2)nc1] | 1-63 | C25H35N3O2 | 409.27 | 410.3 |
| 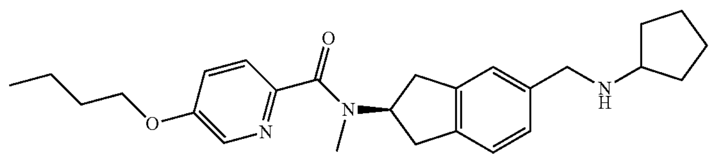 [SMILES: CCCCOc1ccc(C(=O)N(C)[C@@H]2Cc3ccc(CNC4CCCC4)cc3C2)nc1] | 1-64 | C26H35N3O2 | 421.27 | 422.3 |
| 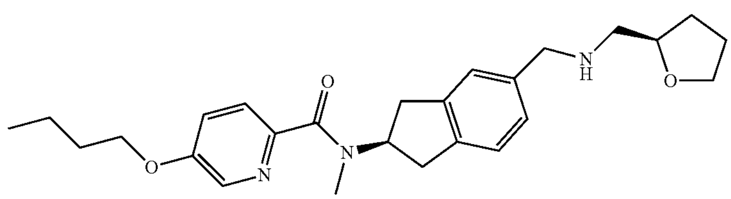 [SMILES: CCCCOc1ccc(C(=O)N(C)[C@@H]2Cc3ccc(CNC[C@H]4CCCO4)cc3C2)nc1] | 1-65 | C26H35N3O3 | 437.27 | 438.3 |
| 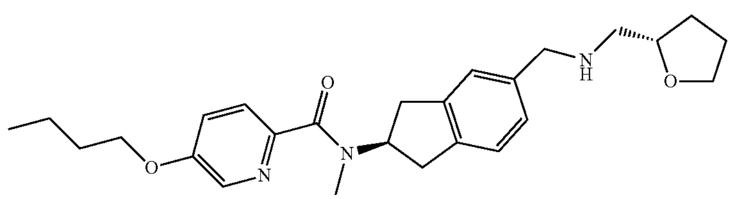 [SMILES: CCCCOc1ccc(C(=O)N(C)[C@@H]2Cc3ccc(CNC[C@@H]4CCCO4)cc3C2)nc1] | 1-66 | C26H35N3O3 | 437.27 | 438.2 |
| 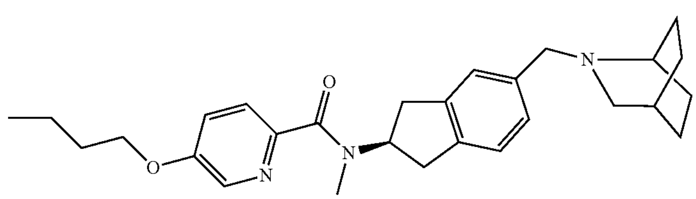 [SMILES: CCCCOc1ccc(C(=O)N(C)[C@@H]2Cc3ccc(CN4CC5CCC4CC5)cc3C2)nc1] | 1-67 | C28H37N3O2 | 447.29 | 448.3 |
| 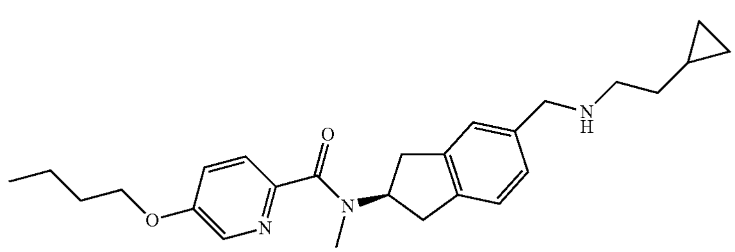 [SMILES: CCCCOc1ccc(C(=O)N(C)[C@@H]2Cc3ccc(CNCCC4CC4)cc3C2)nc1] | 1-68 | C26H35N3O2 | 421.27 | 422.3 |

TABLE 1-continued

| Structure | Ex. No. | Empirical formula | Molecular weight | [M + H]+ ESI-MS |
|---|---|---|---|---|
| 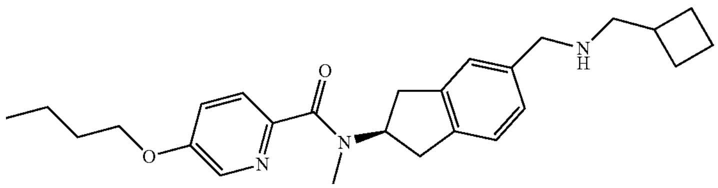 [SMILES: CCCCOc1ccc(C(=O)N(C)[C@@H]2Cc3ccc(CNCC4CCC4)cc3C2)nc1] | 1-69 | C26H35N3O2 | 421.27 | 422.3 |
| 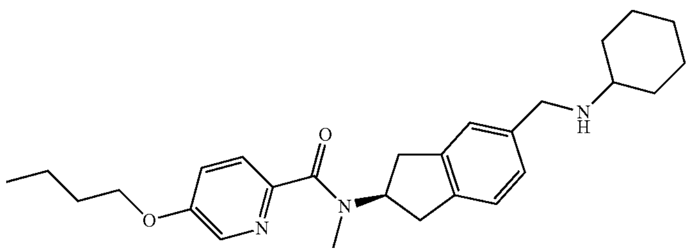 [SMILES: CCCCOc1ccc(C(=O)N(C)[C@@H]2Cc3ccc(CNC4CCCCC4)cc3C2)nc1] | 1-70 | C27H37N3O2 | 435.29 | 436.3 |
| 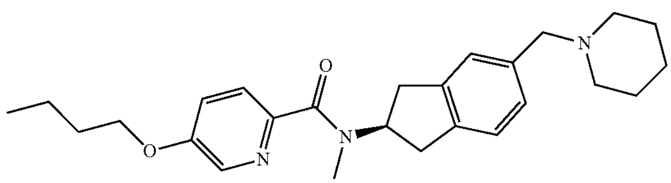 [SMILES: CCCCOc1ccc(C(=O)N(C)[C@@H]2Cc3ccc(CN4CCCCC4)cc3C2)nc1] | 1-71 | C26H35N3O2 | 421.27 | 422.3 |
| 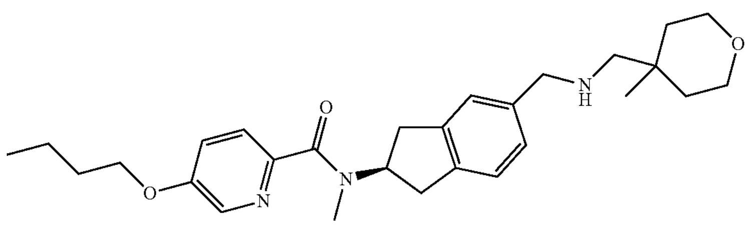 [SMILES: CCCCOc1ccc(C(=O)N(C)[C@@H]2Cc3ccc(CNCC4(C)CCOCC4)cc3C2)nc1] | 1-72 | C28H39N3O3 | 465.3 | 466.3 |
| 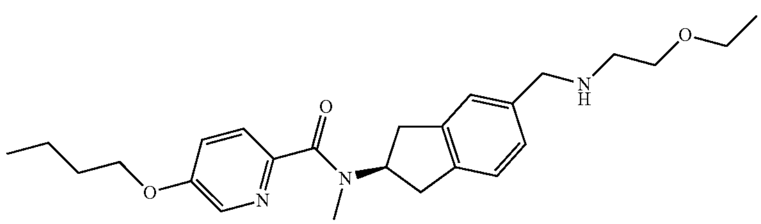 [SMILES: CCCCOc1ccc(C(=O)N(C)[C@@H]2Cc3ccc(CNCCOCC)cc3C2)nc1] | 1-73 | C25H35N3O3 | 425.27 | 426.3 |
| 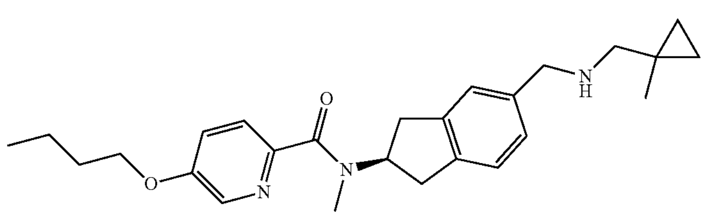 [SMILES: CCCCOc1ccc(C(=O)N(C)[C@@H]2Cc3ccc(CNCC4(C)CC4)cc3C2)nc1] | 1-74 | C26H35N3O2 | 421.27 | 422.3 |
| 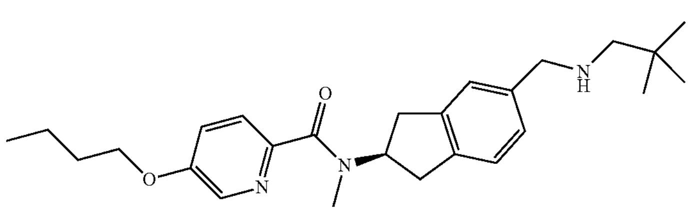 [SMILES: CCCCOc1ccc(C(=O)N(C)[C@@H]2Cc3ccc(CNCC(C)(C)C)cc3C2)nc1] | 1-75 | C26H37N3O2 | 423.29 | 424.3 |

TABLE 1-continued

| Structure | Ex. No. | Empirical formula | Molecular weight | [M + H]+ ESI-MS |
|---|---|---|---|---|
| 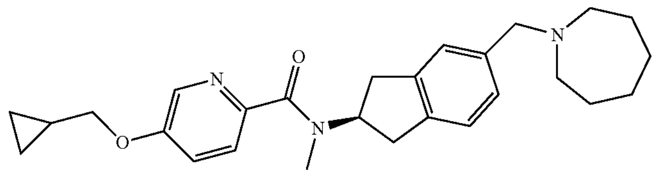 [SMILES: CN(C(=O)c1ccc(OCC2CC2)cn1)[C@@H]1Cc2ccc(CN3CCCCCC3)cc2C1] | 1-76 | C27H35N3O2 | 433.27 | 434.3 |
| 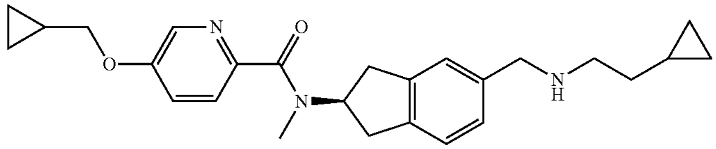 [SMILES: CN(C(=O)c1ccc(OCC2CC2)cn1)[C@@H]1Cc2ccc(CNCCC3CC3)cc2C1] | 1-77 | C26H33N3O2 | 419.26 | 420.4 |
| 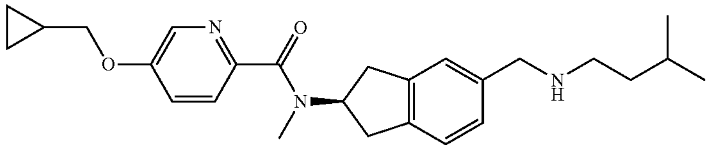 [SMILES: CC(C)CCNCc1ccc2c(c1)C[C@H](N(C)C(=O)c1ccc(OCC3CC3)cn1)C2] | 1-78 | C26H35N3O2 | 421.27 | 422.2 |
| 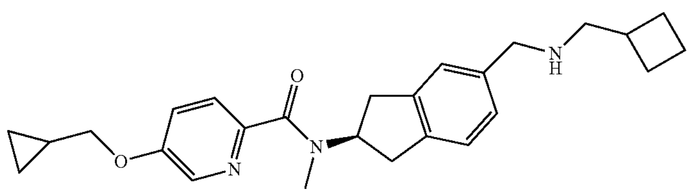 | 1-79 | C26H33N3O2 | 419.26 | 420.3 |
| 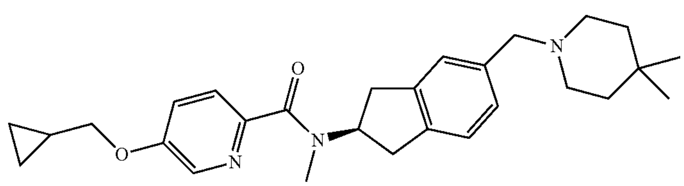 [SMILES: CN(C(=O)c1ccc(OCC2CC2)cn1)[C@@H]1Cc2ccc(CN3CCC(C)(C)CC3)cc2C1] | 1-80 | C28H37N3O2 | 447.29 | 448.4 |
| 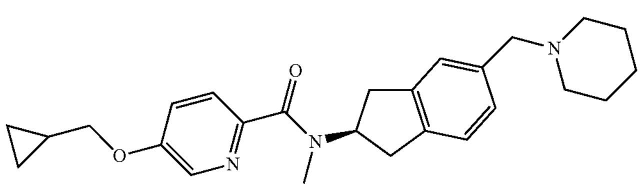 [SMILES: CN(C(=O)c1ccc(OCC2CC2)cn1)[C@@H]1Cc2ccc(CN3CCCCC3)cc2C1] | 1-81 | C26H33N3O2 | 419.26 | 420.2 |
| 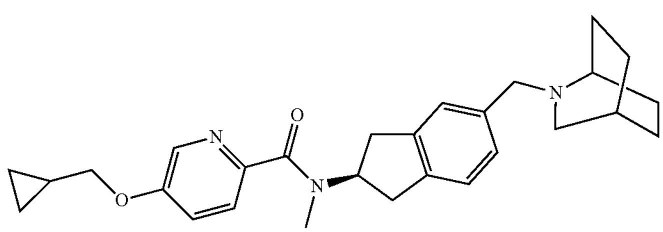 [SMILES: CN(C(=O)c1ccc(OCC2CC2)cn1)[C@@H]1Cc2ccc(CN3CC4CCC3CC4)cc2C1] | 1-82 | C28H35N3O2 | 445.27 | 446.4 |
| 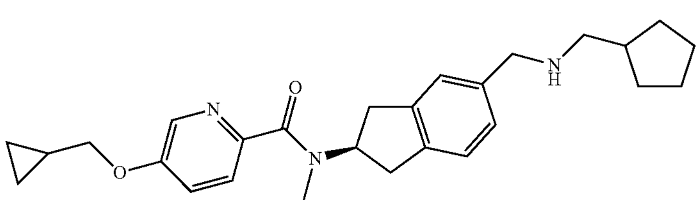 [SMILES: CN(C(=O)c1ccc(OCC2CC2)cn1)[C@@H]1Cc2ccc(CNCC3CCCC3)cc2C1] | 1-83 | C27H35N3O2 | 433.27 | 434.4 |

TABLE 1-continued
| Structure | Ex. No. | Empirical formula | Molecular weight | [M + H] + ESI-MS |
|---|---|---|---|---|
| 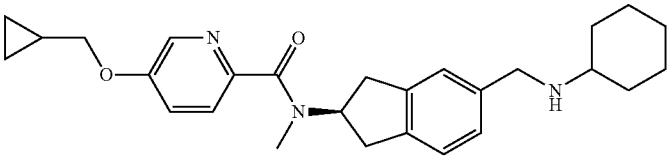 [SMILES: CN(C(=O)c1ccc(OCC2CC2)cn1)[C@@H]1Cc2ccc(CNC3CCCCC3)cc2C1] | 1-84 | C27H35N3O2 | 433.27 | 434.4 |
| 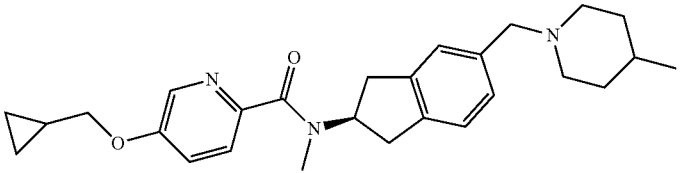 [SMILES: CC1CCN(Cc2ccc3c(c2)C[C@H](N(C)C(=O)c2ccc(OCC4CC4)cn2)C3)CC1] | 1-85 | C27H35N3O2 | 433.27 | 434.3 |
| 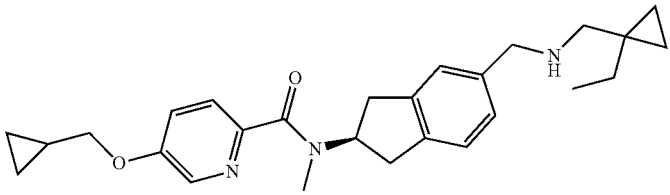 [SMILES: CCC1(CNCc2ccc3c(c2)C[C@H](N(C)C(=O)c2ccc(OCC4CC4)cn2)C3)CC1] | 1-86 | C27H35N3O2 | 433.27 | 434.4 |
| 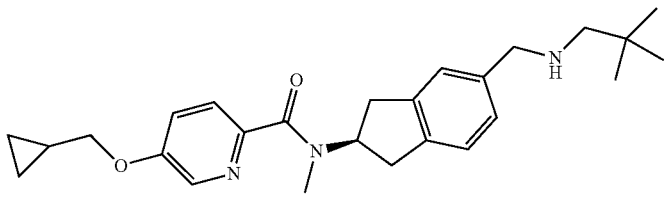 [SMILES: CN(C(=O)c1ccc(OCC2CC2)cn1)[C@@H]1Cc2ccc(CNCC(C)(C)C)cc2C1] | 1-87 | C26H35N3O2 | 421.27 | 422.4 |
| 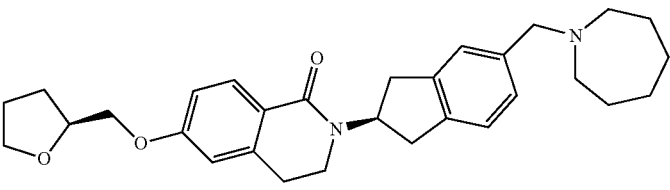 [SMILES: O=C1c2ccc(OC[C@@H]3CCCO3)cc2CCN1[C@@H]1Cc2ccc(CN3CCCCCC3)cc2C1] | 1-88 | C30H38N2O3 | 474.29 | 475.3 |
| 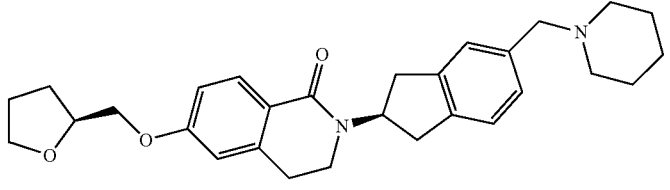 [SMILES: O=C1c2ccc(OC[C@@H]3CCCO3)cc2CCN1[C@@H]1Cc2ccc(CN3CCCCC3)cc2C1] | 1-89 | C29H36N2O3 | 460.27 | 461.3 |
| 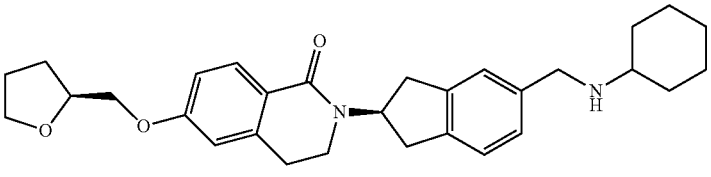 [SMILES: O=C1c2ccc(OC[C@@H]3CCCO3)cc2CCN1[C@@H]1Cc2ccc(CNC3CCCCC3)cc2C1] | 1-90 | C30H38N2O3 | 474.29 | 475.3 |
| 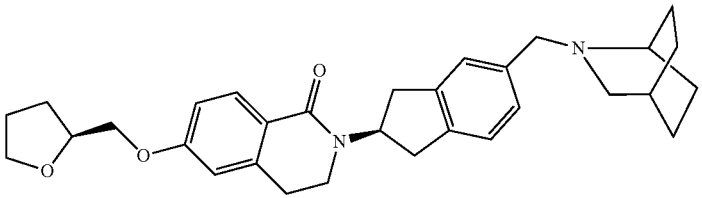 [SMILES: O=C1c2ccc(OC[C@@H]3CCCO3)cc2CCN1[C@@H]1Cc2ccc(CN3CC4CCC3CC4)cc2C1] | 1-91 | C31H38N2O3 | 486.29 | 487.3 |

TABLE 1-continued

| Structure | Ex. No. | Empirical formula | Molecular weight | [M + H] + ESI-MS |
|---|---|---|---|---|
| 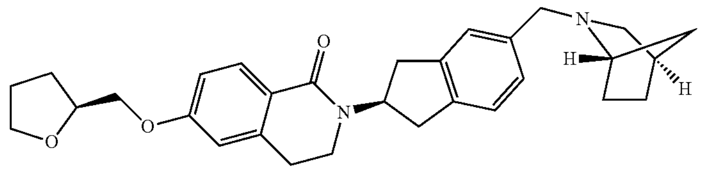 [SMILES: O=C1c2ccc(OC[C@@H]3CCCO3)cc2CCN1[C@@H]1Cc2ccc(CN3C[C@@H]4CC[C@H]3C4)cc2C1] | 1-92 | C30H36N2O3 | 472.27 | 473.3 |

Preparation of Starting Materials Required (Aromatic Aldehydes)

4-Cyclopropylmethoxy-N-((R)-5-formylindan-2-yl)-N-methylbenzamide

Method D

A mixture of 4-cyclopropylmethoxy-N-((R)-5-formylindan-2-yl)benzamide (5.6 g), methyl iodide (2.6 g) and DMF (100 ml) was admixed at 0° C. with portions of sodium hydride (60% in paraffin oil; 0.48 g). After 15 minutes, the reaction mixture was poured into saturated ammonium chloride solution and extracted with ethyl acetate. The organic phase was dried over sodium sulfate and concentrated. The residue was chromatographed on silica gel This afforded the product with the molecular weight of 349.43 (C22H23NO3); MS (ESI): 350 (M+H+).

N-((R)-5-Formylindan-2-yl)-4-[(S)-1-(tetrahydrofuran-2-yl)methoxy]benzamide

According to method C, 4-[(S)-1-(tetrahydrofuran-2-yl)methoxy]benzoic acid was reacted with (R)-5-bromoindan-2-ylamine, and the resulting amide (N-((R)-5-bromoindan-2-yl)-4-[(S)-1-(tetrahydrofuran-2-yl)methoxy]benzamide) was then formylated according to method B. This afforded the product with the molecular weight of 365.43 (C22H23NO4); MS (ESI): 366 (M+H+).

N-((R)-5-Formylindan-2-yl)-N-methyl-4-[(S)-1-(tetrahydrofuran-2-yl)methoxy]benzamide According to method D, N-((R)-5-formylindan-2-yl)-4-[(S)-1-(tetrahydrofuran-2-yl)-methoxy]benzamide was methylated. This afforded the product with the molecular weight of 379.46 (C23H25NO4); MS (ESI): 380 (M+H+).

N-((R)-5-Formylindan-2-yl)-5-[(S)-1-(tetrahydrofuran-2-yl)methoxy]pyridine-2-carboxamide Method E A mixture of N-((R)-5-vinylindan-2-yl)-5-[(S)-1-(tetrahydrofuran-2-yl)methoxy]pyridine-2-carboxamide (0.60 g) and 2-propanol (5 ml) was admixed with a mixture of sodium periodate (0.775 g) and water (3 ml). Osmium(VIII) oxide (solution in tert-butanol; 16.7 mg) was added and the mixture was stirred vigorously for 3 hours. The reaction mixture was partitioned between water and ethyl acetate. The organic phase was dried over sodium sulfate and concentrated. This afforded the product with the molecular weight of 366.42 (C21H22N2O4); MS (ESI): 367 (M+H+).

N-((R)-5-Vinylindan-2-yl)-5-[(S)-1-(tetrahydrofuran-2-yl)methoxy]pyridine-2-carboxamide Method F A mixture of N-((R)-5-bromoindan-2-yl)-5-[(S)-1-(tetrahydrofuran-2-yl)methoxy]pyridine-2-carboxamide (1.70 g), tributylvinyltin (1.55 g), triphenylphosphine (85.5 mg), palladium(II) acetate (18.3 mg) and DMF (20 ml) was admixed under argon with triethylamine (7.4 ml) and heated to reflux for 4 hours. After cooling, the reaction mixture was partitioned between water and ethyl acetate. The organic phase was dried over sodium sulfate and concentrated. The residue was filtered through silica gel. This afforded the product with the molecular weight of 364.45 (C22H24N2O3); MS (ESI): 365 (M+H+).

N-((R)-5-Bromoindan-2-yl)-5-[(S)-1-(tetrahydrofuran-2-yl)methoxy]pyridine-2-carboxamide Method G A mixture of N-((R)-5-bromoindan-2-yl)-5-hydroxypyridine-2-carboxamide (1.50 g), (S)-1-(tetrahydrofuran-2-yl)methyl methanesulfonate (0.81 g), cesium carbonate (1.46 g) and DMF (20 ml) was heated to 60° C. for 4 hours. The cooled reaction mixture was admixed with water and extracted with ethyl acetate. The organic phase was washed three times with water, dried over magnesium sulfate and concentrated. This afforded the product with the molecular weight of 417.31 (C20H21BrN2O3); MS (ESI): 417 (M+H+).

N-((R)-5-Bromoindan-2-yl)-5-hydroxypyridine-2-carboxamide

According to method C, 5-hydroxypyridine-2-carboxylic acid was reacted with (R)-5-bromo-indan-2-ylamine. This afforded the product with the molecular weight of 333.19 (C15H13BrN2O2); MS (ESI); 333 (M+H+).

N-((R)-5-Formylindan-2-yl)-5-cyclopropylmethoxypyridine-2-carboxamide

Analogously to the preparation of N-((R)-5-formylindan-2-yl)-5-[(S)-1-(tetrahydrofuran-2-yl)methoxy]pyridine-2-carboxamide, N-((R)-5-bromoindan-2-yl)-5-hydroxypyridine-2-carboxamide was first alkylated with cyclopropylmethyl bromide according to method G, then the resulting amide was vinylated according to method E and finally cleaved oxidatively to the aldehyde according to method E. This afforded the product with the molecular weight of 336.39 (C20H20N2O3); MS (ESI): 337 (M+H+).

N-((R)-5-Formylindan-2-yl)methyl-5-butoxypyridine-2-carboxamide

According to method G, N-((R)-5-bromoindan-2-yl)-5-hydroxypyridine-2-carboxamide was alkylated with butyl bromide, and then the resulting amide was methylated on the amide nitrogen according to method D. Vinylation according to method F and final oxidative cleavage according to method E gives rise to the aldehyde. This afforded the product with the molecular weight of 352.44 (C21H24N2O3); MS (ESI): 353 (M+H+).

N-(R)-5-Formylindan-2-yl-N-methyl-5-cyclopropylmethoxypyridine-2-carboxamide According to method G, N-(R)-5-bromoindan-2-yl-5-hydroxypyridine-2-carboxamide was alkylated with cyclopropylmethyl bromide and then the amide obtained was methylated on the amide nitrogen according to method D. Vinylation of the N-(R)-5-bromoindan-2-yl-N-methyl-5-cyclopropylmethoxypyridine-2-carboxamide thus obtained according to method F and final oxidative cleavage according to method E gives rise to the aldehyde. This afforded the product with the molecular weight of 350.42 (C21H22N2O3); MS (ESI): 351 (M+H+).

(R)-2-{1-Oxo-6-[(S)-1-(tetrahydrofuran-2-yl)methoxy]-3,4-dihydro-1H-isoquinolin-2-yl}-indane-5-carbaldehyde According to method F and method E, 2-((R)-5-bromoindan-2-yl)-6-[(S)-1-(tetrahydrofuran-2-yl)methoxy]-3,4-dihydro-2H-isoquinolin-1-one was first vinylated and then cleaved oxidatively. This afforded the product with the molecular weight of 391.47 (C24H25NO4); MS (ESI): 392 (M+H+).

2-((R)-5-Bromoindan-2-yl)-6-[(S)-1-(tetrahydrofuran-2-yl)methoxy]-3,4-dihydro-2H-isoquinolin-1-one Method H
A mixture of (R)-5-bromoindan-2-ylamine (hydrochloride, 1.05 g), THF (20 ml) and diisopropylethylamine (1.0 g) was admixed with 2-(2-chloroethyl)-4-[(S)-1-(tetrahydrofuran-2-yl)methoxy]benzoyl chloride (1.28 g; from 6-[(S)-1-(tetrahydrofuran-2-yl)methoxy]-isochroman-1-one by boiling with thionyl chloride). After 5 minutes, potassium tert-butoxide (1.42 g) was added. After 12 hours, the reaction mixture was partitioned between water and ethyl acetate. The organic phase was dried over sodium sulfate and concentrated. The residue was chromatographed on silica gel (eluent: 1:1 ethyl acetate/heptane). This afforded the product with the molecular weight of 442.36 (C23H24BrNO3); MS (ESI): 442 (M+H+).

Preparation of Starting Materials Required (Amines)

C-(4-Methyltetrahydropyran-4-yl)methylamine

A mixture of tetrahydropyran-4-carbonitrile (5.00 g) and THF (50 ml) was admixed at 0° C. with lithium hexamethyldisilazide (1 M, 63 ml) and, after 90 minutes, methyl iodide (4.26 ml) was added dropwise with good cooling. After 2 hours, the reaction mixture was partitioned between water and ethyl acetate. The organic phase was dried over sodium sulfate and concentrated. The residue was dissolved in THF (200 ml), and lithium aluminum hydride (3.79 g) was added. The mixture was boiled at reflux for 6 hours. Water (3.8 ml) and then sodium hydroxide solution (40%; 3.8 ml) were cautiously added dropwise to the cooled suspension. The precipitate was filtered off and the filtrate was concentrated. This afforded the product with the molecular weight of 129.20 (C7H15NO); MS (ESI): 130 (M+H+).

(1S,4R)-2-Azabicyclo[2.2.1]heptane

Method I
A mixture of (1S,4R)-2-azabicyclo[2.2.1]heptan-3-one (18.0 g), lithium aluminum hydride (7.4 g) and THF (350 ml) was boiled at reflux for 3 hours. Water (7.4 ml) and then sodium hydroxide solution (40%; 7.4 ml) were cautiously added dropwise to the cooled suspension. The precipitate was filtered off and the filtrate was concentrated. This afforded the product with the molecular weight of 97.16 (C6H11N); MS (ESI): 98 (M+H+). The filtrate can also be used directly in reductive aminations (method A).

(1S,4R)-2-Azabicyclo[2.2.1]heptan-3-one

A suspension of (1R,4S)-2-azabicyclo[2.2.1]hept-5-en-3-one (20.0 g), palladium (5% on activated carbon; 2.0 g) and ethyl acetate (250 ml) was stirred vigorously under an atmosphere of hydrogen for 5 hours. The catalyst was filtered off with suction and the filtrate was concentrated. This afforded the product with the molecular weight of 111.14 (C6H9NO); MS (ESI): 112 (M+H+).

C-(1-Methylcyclopropyl)methylamine

A mixture of 1-methylcyclopropanecarboxylic acid (3.0 g) was heated with thionyl chloride (3.6 g) to reflux for 3 hours. The cooled reaction mixture was poured into a concentrated aqueous ammonia solution. Extraction with diethyl ether gave an organic phase, which was dried over sodium sulfate and concentrated. The residue was treated with lithium aluminum hydride according to method I. In an analogous manner, it is also possible to prepare C-(1-ethylcyclopropyl)methylamine.

Example 2

4-Butoxy-N-methyl-N-((R)-(R)-5-pyrrolidin-2-ylindan-2-yl)benzamide

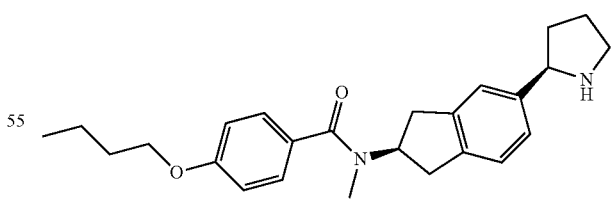

Method J
To a solution of (−)-sparteine (1.40 g) and tert-butyl pyrrolidine-1-carboxylate (1.02 g) in methyl tert-butyl ether (15 ml) was added dropwise, at −78° C., s-butyllithium (1.3 M in cyclohexane, 4.6 ml), in the course of which the temperature was kept below −73° C. After three hours at −78° C., zinc chloride (1.47 M in diethyl ether; 3.4 ml) was added dropwise. After 30 minutes, the reaction mixture was warmed to room temperature and kept at this temperature for 30 minutes. N-((R)-5-Bromoindan-2-yl)-4-butoxy-N-methylbenzamide (1.00 g), palladium(II) acetate (28 mg) and tri-tert-butylphosphine (HBF4 salt; 43 mg) were added. After very brief spontaneous heating to 35° C., the reaction mixture was kept at 20° C. for 12 hours and then partitioned between water and ethyl acetate. The organic phase was concentrated and the residue was purified by chromatography on silica gel (eluent: 1:1 ethyl acetate/n-heptane), Finally, the Boc protecting group was detached by dissolution in dichloromethane, treatment with hydrogen chloride (5-6 M in 2-propanol) and concentration. This afforded the product with the monoisotopic molecular weight of 392.25 (C25H32N2O2); MS (ESI): 393.3 (M+H+).

N-((R)-5-Bromoindan-2-yl)-4-butoxy-N-methylbenzamide

A mixture of (R)-5-bromoindan-2-ylamine (hydrochloride; 3.50 g), diisopropylethylamine (5.0 ml) and dichloromethane (20 ml) was admixed at 0° C. with 4-butoxybenzoyl chloride (3.00 g). After 30 minutes, the reaction mixture was partitioned between water and dichloromethane. The organic phase was concentrated and the residue was stirred with diethyl ether. The resulting amide was methylated on the amide nitrogen according to method D. This afforded the product with the molecular weight of 402.33 (C21H24BrNO2); MS (ESI): 402 (M+H+).

Example 3-1

N-Methyl-N-[(R)-5-(1-methylpyrrolidin-2-yl)indan-2-yl]-5-cyclopropylmethoxypyridine-2-carboxamide

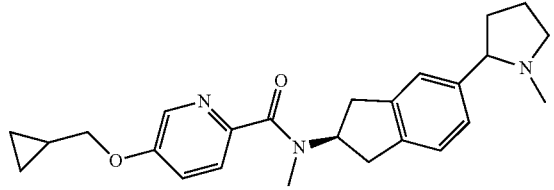 [SMILES: CN1CCCC1c1ccc2c(c1)C[C@H](N(C)C(=O)c1ccc(OCC3CC3)cn1)C2]

According to method A, N-methyl-((R)-5-pyrrolidin-2-ylindan-2-yl)-5-cyclopropylmethoxypyridine-2-carboxamide was reacted with formaldehyde (aqueous solution). This afforded the product with the monoisotopic molecular weight of 405.24 (C25H31N3O2); MS (ESI): 406.4 (M+H+).

N-Methyl-N-((R)-5-pyrrolidin-2-ylindan-2-yl)-5-cyclopropylmethoxypyridine-2-carboxamide A solution of tert-butyl 2-{(R)-2-[(5-cyclopropylmethoxypyridine-2-carbonyl)methylamino]indan-5-yl}pyrrole-1-carboxylate (0.20 g) in ethanol (3 ml) and glacial acetic acid (0.5 ml) was admixed with Pt/C (5%; 100 mg) and stirred under a hydrogen atmosphere (3 bar) for 12 hours. The catalyst was filtered off and the solution was concentrated. The residue was dissolved in dichloromethane (3 ml), and hydrogen chloride (5-6 M in 2-propanol; 3 m) was added. After one hour, volatile fractions were removed. This afforded the product with the molecular weight of 391.52 (C24H29N3O2), MS (ESI): 392 (M+H+).

tert-Butyl 2-{(R)-2-[(5-cyclopropylmethoxypyridine-2-carbonyl)methylamino]indan-5-yl}-pyrrole-1-carboxylate A mixture of N-((R)-5-bromoindan-2-yl)-N-methyl-5-cyclopropylmethoxypyridine-2-carboxamide (0.20 g), 1-(t-butoxycarbonyl)pyrrole-2-boronic acid (105 mg), tetrakis (triphenylphosphine)palladium(0) (36 mg) and dimethoxyethane (6.2 ml) was admixed under argon with sodium carbonate (53 mg as a saturated aqueous solution) and heated to 92° C. for 30 minutes. The cooled reaction mixture was partitioned between water and ethyl acetate. The organic phase was dried over sodium sulfate, filtered and concentrated. The residue was purified by chromatography (silica gel, eluent: 40% n-heptane in ethyl acetate). This afforded the product with the molecular weight of 487.60 (C29H33N3O4); MS (ESI): 488 (M+H+).

Example 3-2

N-[(R)-5-(1-Ethylpyrrolidin-2-yl)indan-2-yl]-N-methyl-5-cyclopropylmethoxypyridine-2-carboxamide

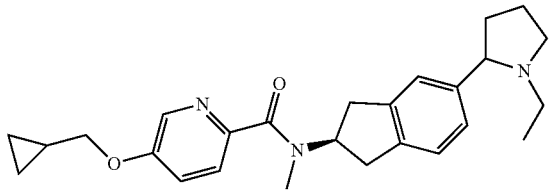 [SMILES: CCN1CCCC1c1ccc2c(c1)C[C@H](N(C)C(=O)c1ccc(OCC3CC3)cn1)C2]

According to method A, N-methyl-N-((R)-5-pyrrolidin-2-ylindan-2-yl)-5-cyclopropylmethoxypyridine-2-carboxamide was reacted with acetaldehyde. The product was thus obtained with the monoisotopic molecular weight of 419.26 (C26H33N3O2); MS (ESI): 420.4 (M+H+).

Table 2 summarizes examples of results obtained which were obtained in the above-described calcium mobilization assay.

TABLE 2

| Ex. No. | IC50 µM |
|---|---|
| 1-05 | 0.294 |
| 1-09 | 0.139 |
| 1-15 | 0.123 |
| 1-23 | 0.144 |
| 1-27 | 0.117 |
| 1-31 | 0.111 |
| 1-32 | 0.147 |
| 1-34 | 0.121 |
| 1-36 | 0.198 |
| 1-38 | 0.115 |
| 1-40 | 0.208 |
| 1-42 | 0.222 |
| 1-46 | 0.144 |
| 1-47 | 0.229 |
| 1-50 | 0.766 |
| 1-55 | 0.848 |
| 1-58 | 1.040 |
| 1-62 | 0.173 |
| 1-66 | 0.194 |
| 1-72 | 0.147 |
| 1-81 | 0.179 |
| 1-90 | 0.777 |

TABLE 2-continued

| Ex. No. | IC50 μM |
|---|---|
| 2 | 0.255 |
| 3-1 | 1.137 |

The invention claimed is:

1. A compound of the formula I

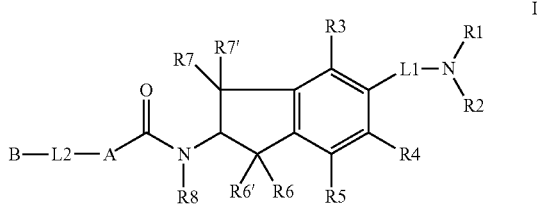

in which

R1
is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R9), (C(R10)(R11))$_q$-R12, CO(C(R13)(R14))$_r$-R15, CO—O($C_1-C_8$)-alkyl, CO(C(R13)(R14))$_r$-N(R16)(R17);

R2
is H, $(C_1-C_8)$-alkyl, $(C_1-C_4)$-alkoxy-$(C_1-C_4)$-alkyl, $(C_3-C_8)$-alkenyl, $(C_3-C_8)$-alkynyl, CO(R9), (C(R10)(R11))$_q$-R12, CO(C(R13)(R14))$_r$-R15, CO—O($C_1-C_8$)-alkyl, CO(C(R13)(R14))$_r$-N(R16)(R17);

or

R1 and R2 form, together with the nitrogen atom to which they are bonded, a 4- to 10-membered mono-, bi- or spirocyclic ring which, apart from the nitrogen atom, optionally including 0 to 3 additional heteroatoms selected from the group of oxygen, nitrogen and sulfur, where the heterocyclic ring system is optionally substituted by F, Cl, Br, $CF_3$, CN, $(C_1-C_6)$-alkyl, $(C_3-C_8)$-cycloalkyl, O—$(C_1-C_8)$-alkyl, $(C_1-C_4)$-alkoxy-$(C_1-C_4)$-alkyl, hydroxy-$(C_1-C_6)$-alkyl, oxo, CO(R18), CON(R19)(R20), hydroxyl, COO(R21), N(R22)CO($C_1-C_6$)-alkyl, N(R23)(R24) or $SO_2(C_1-C_6)$-alkyl;

R10, R11
are each independently H, $(C_1-C_6)$-alkyl, hydroxy-$(C_1-C_2)$-alkyl, F, OH;

R9, R13, R14, R16, R17, R18, R19, R20, R21, R22, R23, R24
are each independently H, $(C_1-C_6)$-alkyl;

or

R16 and R17, R23 and R24
optionally form, together with the nitrogen atom to which they are bonded, a 5-6-membered ring which, apart from the nitrogen atom, optionally including 0-1 further heteroatom from the group of NH, N—$(C_1-C_6)$-alkyl, oxygen and sulfur;

q, r are each independently 0, 1, 2, 3, 4, 5, 6;

R12, R15
are each independently H, OH, F, O—$(C_1-C_6)$-alkyl, S—$(C_1-C_6)$-alkyl, CN, COO(R25), N(R26)CO($C_1-C_6$)-alkyl, N(R27)(R28), CON(R29)(R30), $SO_2(C_1-C_6)$-alkyl, a 3-12-membered mono-, bi- or spirocyclic ring which may contain one to four heteroatoms from the group of N, O and S and the 3-12-membered ring optionally containing further substituents such as F, Cl, Br, OH, $CF_3$, $NO_2$, CN, $OCF_3$, oxo, O—$(C_1-C_6)$-alkyl, $(C_1C_4)$-alkoxy-$(C_1-C_4)$-alkyl, S—$(C_1-C_6)$-alkyl, $(C_1-C_6)$-alkyl, $(C_2-C_6)$-alkenyl, $(C_3-C_8)$-cycloalkyl, O—$(C_3-C_8)$-cycloalkyl, $(C_3-C_8)$-cycloalkenyl, O—$(C_3-C_8)$-cycloalkenyl, $(C_2-C_6)$-alkynyl, N(R31)(R32), COO(R33), $SO_2(C_1-C_6)$-alkyl and COOH;

R25, R26, R27, R28, R29, R30, R31, R32, R33
are each independently H, $(C_1-C_6)$-alkyl;

or

R27 and R28, R29 and R30, R31 and R32
each independently optionally form, together with the nitrogen atom to which they are bonded, a 5-6-membered ring which, apart from the nitrogen atom, optionally including 0-1 further heteroatom from the group of NH, N—$(C_1-C_6)$-alkyl, oxygen and sulfur;

L1 is C(R34)(R35), C(R36)(R37)C(R38)(R39), $(C_3-C_6)$-cycloalkyl;

R2 may optionally be joined to one of the R34, R35, R36, R37, R38 or R39 radicals so as to form an optionally $(C1-C6)$-alkyl-substituted 5-6-membered ring;

R34, R35, R36, R37, R38, R39
are each independently H, $(C_1-C_6)$-alkyl;

R3, R4, R5
are each independently H, F, Cl, Br, I, OH, $CF_3$, $NO_2$, CN, $OCF_3$, O—$(C_1-C_6)$-alkyl, S—$(C_1-C_6)$-alkyl, O—$(C_1-C_4)$-alkoxy-$(C_1-C_4)$-alkyl, $(C_1-C_6)$-alkyl, CON(R40)(R41), CO(R42);

R40, R41, R42
are each independently H, $(C_1-C_6)$-alkyl;

or

R40 and R41
each independently optionally form, together with the nitrogen atom to which they are bonded, a 5-6-membered ring which, apart from the nitrogen atom, optionally including 0-1 further heteroatom from the group of NH, N—$(C_1-C_6)$-alkyl, oxygen and sulfur;

R6, R6', R7, R7'
are each independently H, F, $(C_1-C_6)$-alkyl, OH, O—$(C_1-C_6)$-alkyl;

R8 is H, $(C_1-C_6)$-alkyl;

A is a 5-6-membered aromatic ring optionally including up to 2 heteroatoms selected from the group of nitrogen, oxygen and sulfur, and optionally substituted by one or more of the substituents H, F, Cl, Br, I, OH, $CF_3$, $NO_2$, CN, $OCF_3$, O—$(C_1-C_6)$-alkyl, O—$(C_1-C_4)$-alkoxy-$(C_1-C_4)$-alkyl, $(C_1-C_6)$-alkyl, N(R43)(R44), $SO_2$-$CH_3$, CON(R45)(R46), N(R47)CO(R48), CO(R49);

optionally, C(O)NR8 is joined to an ortho substituent of A via a bridge comprising one or two elements from the group of carbon and nitrogen so as to form, overall, a 9- to 10-membered bicyclic ring;

R43, R44, R45, R46, R47, R48, R49 are each independently H, $(C_1-C_6)$-alkyl;

or

R43 and R44, R45 and R46
each independently optionally form, together with the nitrogen atom to which they are bonded, a 5-6-membered ring which, apart from the nitrogen atom, optionally including 0-1 further heteroatom from the group of NH, N—$(C_1-C_6)$-alkyl, oxygen and sulfur;

L2 is a bond or a linker with 1 to 4 members, where the members are selected from the group consisting of O and C(R51)(R52), to form a chemically viable radical, and the linker has no O—CO or COO groups;

B is $(C_1-C_6)$-alkyl or a 3- to 5 membered nonaromatic ring including 0 to 3 oxygen atoms, where the ring system is optionally substituted by one or more of the following substituents: F, CF$_3$, (C$_1$-C$_6$)-alkyl, O—(C$_1$-C$_8$)-alkyl, (C$_1$-C$_4$)-alkoxy-(C$_1$-C$_4$)-alkyl, hydroxy-(C$_1$-C$_4$)-alkyl, oxo, CO(R53), hydroxyl;

R50, R51, R52, R53
are each independently H, (C$_1$-C$_6$)-alkyl;
and the physiologically compatible salts thereof.

2. The compound as claimed in claim 1, in which R1 is H, (C$_1$-C$_8$)-alkyl, (C(R10)(R11))$_q$-R12, (C$_1$-C$_4$)-alkoxy-(C$_1$-C$_4$)-alkyl;
R2 is (C$_1$-C$_8$)-alkyl, (C(R10)(R11))$_q$-R12, (C$_1$-C$_4$)-alkoxy-(C$_1$-C$_4$)-alkyl;
or
R1 and R2 form, together with the nitrogen atom to which they are bonded, a 4- to 10-membered mono-, bi- or spirocyclic ring which, apart from the nitrogen atom, including 0 to 2 additional heteroatoms selected from the group of oxygen, nitrogen and sulfur, where the heterocyclic ring system is optionally substituted by F, CF$_3$, (C$_1$-C$_6$)-alkyl, —(C$_1$-C$_8$)-alkyl, (C$_1$-C$_4$)-alkoxy-(C$_1$-C$_4$)-alkyl, hydroxy-(C$_1$-C$_6$)-alkyl, oxo, CO(R18) or hydroxyl;
R10, R11
are each independently H, (C$_1$-C$_6$)-alkyl, hydroxy-(C$_1$-C$_2$)-alkyl, F, OH;
R18 is H, (C$_1$-C$_6$)-alkyl.
q is 0, 1, 2, 3, 4;
R12
is H, OH, F, O—(C$_1$-C$_6$)-alkyl, N(R26)CO(C$_1$-C$_6$)-alkyl, SO$_2$(C$_1$-C$_6$)-alkyl, a 3-12-membered mono-, bi- or spirocyclic ring optionally containing one to three heteroatoms from the group of N, O and S and the 3-12-membered ring optionally containing further substituents such as F, Cl, Br, OH, CF$_3$, CN, OCF$_3$, oxo, O—(C$_1$-C$_6$)-alkyl, (C$_1$-C$_4$)-alkoxy-(C$_1$-C$_4$)-alkyl, (C$_1$-C$_6$)-alkyl, (C$_2$-C$_6$)-alkenyl, (C$_2$-C$_6$)-alkynyl, N(R31)(R32) and SO$_2$(C$_1$-C$_6$)-alkyl.

3. The compound as claimed in claim 1, in which
A is selected from the group consisting of

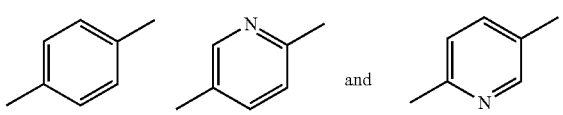

and which can be optionally substituted by one or more of the substituents H, F, Cl, Br, I, OH, CF$_3$, NO$_2$, CN, OCF$_3$, O—(C$_1$-C$_6$)-alkyl, O—(C$_1$-C$_4$)-alkoxy-(C$_1$-C$_4$)-alkyl, (C$_1$-C$_6$)-alkyl, N(R43)(R44), SO$_2$-CH$_3$, CON(R45)(R46), N(R47)CO(R48), CO(R49).

4. The compound as claimed in claim 1, in which
L2 is O or C(R51)(R52)O.

5. The compound as claimed in claim 1, in which
B is a 3- to 5-membered nonaromatic ring which includes 1 or 2 oxygen atoms, where the ring system is optionally substituted by one or more of the following substituents: F, (C$_1$-C$_6$)-alkyl, O—(C$_1$-C$_8$)-alkyl, (C$_1$-C$_4$)-alkoxy-(C$_1$-C$_4$)-alkyl, oxo, hydroxyl, preferably (C$_1$-C$_6$)-alkyl or hydroxyl.

6. The compound as claimed in claim 1, in which
the combined element B-L2 is selected from the group of

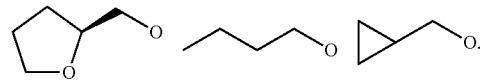

7. The compound as claimed in claim 1, in which
R3, R4, R5 are each H; and R6, R6', R7, R7'are each H.

8. The compound as claimed in claim 1, characterized by the formula II

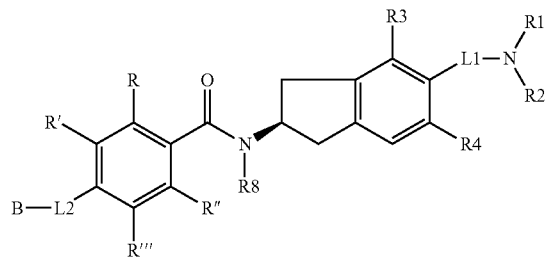

in which the variables R1, R2, L1, R3, R4 and R8 are each as defined in claim 1
and
R, R', R", R'"
are each independently H, F, Cl, Br, I, OH, CF$_3$, NO$_2$, CN, OCF$_3$, O—(C$_1$-C$_6$), alkyl, O—(C$_1$-C$_4$)-alkoxy-(C$_1$-C$_4$)-alkyl, (C$_1$-C$_6$)-alkyl, N(R43)(R44), SO$_2$-CH$_3$, CON(R45)(R46), N(R47)CO(R48), CO(R49);
L2 is CH$_2$O;
B is a 3-to 5-membered nonaromatic ring optionally including 1 or 2 oxygen atoms, where the ring system is optionally substituted by one or more of the following substituents: F, (C$_1$-C$_6$)-alkyl, O—(C$_1$-C$_8$)-alkyl, (C$_1$-C$_4$)-alkoxy-(C$_1$-C$_4$)-alkyl, oxo, hydroxyl, preferably (C$_1$-C$_6$)-alkyl or hydroxyl.

9. The compound as claimed in claim 8, characterized by the formula IIa

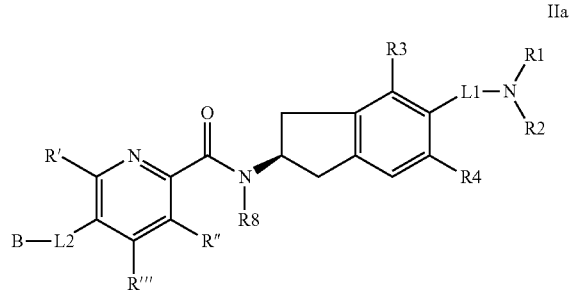

in which the variables R1, R2, L1, R3, R4, R8, R', R", R'", L2 and B are each as defined in claim 8.

10. The compound as claimed in claim 1, characterized by the formula III

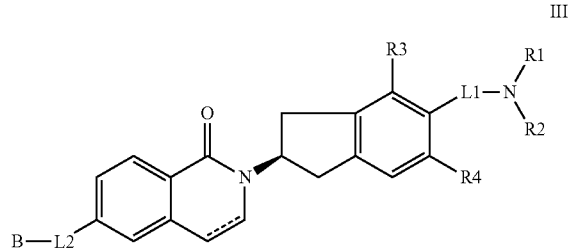

in which R1, R2, R3, R4, L1, L2 and B are each as defined in claim 1; and the broken line indicates an optional double bond, such that both dihydroisoquinolinones and isoquinolinones are embraced by the formula III.

11. The compound as claimed in claim 1, characterized by the formula IV

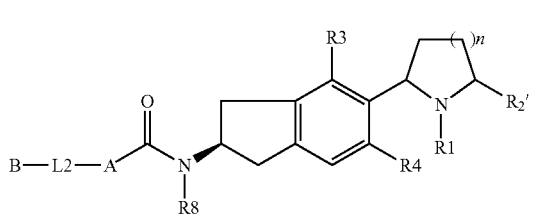

in which R1, R3, R4, R8, L2, A and B are each as defined in claim 1;

n is 1 or 2; and

R2' is H, methyl or ethyl.

12. A pharmaceutical composition comprising the compound of claim 1, and pharmaceutically acceptable salts thereof.

13. The pharmaceutical composition according to claim 12, further comprising one or more active ingredients which have favorable effects on metabolic disorders or diseases associated therewith.

14. The pharmaceutical composition according to claim 12, further comprising one or more antidiabetics.

15. The pharmaceutical composition according to claim 12, further comprising one or more lipid modulators.

16. The pharmaceutical composition according to claim 12, further comprising one or more antiobesity agents.

* * * * *

UNITED STATES PATENT AND TRADEMARK OFFICE
CERTIFICATE OF CORRECTION

PATENT NO.       : 8,552,199 B2                                                Page 1 of 1
APPLICATION NO. : 13/201410
DATED            : October 8, 2013
INVENTOR(S)      : Schwink et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 56 days.

Signed and Sealed this

Fifteenth Day of September, 2015

Michelle K. Lee
*Director of the United States Patent and Trademark Office*